United States Patent
Bentsen et al.

[11] Patent Number: 5,958,782
[45] Date of Patent: Sep. 28, 1999

[54] CATION-SENSING COMPOSITE STRUCTURE AND COMPOUNDS FOR USE THEREIN

[75] Inventors: James G. Bentsen, North St. Paul; Shih-Hung Chou, Maplewood; Elisa M. Cross, St. Paul; Kurt J. Halverson, Lake Elmo; John E. Trend, St. Paul; Cary A. Kipke, Woodbury, all of Minn.; Masao Yafuso, Lake Forest; Sanjay L. Patil, Aliso Viejo, both of Calif.

[73] Assignee: Minnesota Mining and Manufacturing Company, St. Paul, Minn.

[21] Appl. No.: 08/810,969

[22] Filed: Feb. 27, 1997

Related U.S. Application Data

[60] Continuation-in-part of application No. 08/521,869, Aug. 31, 1995, abandoned, which is a division of application No. 08/140,257, Oct. 21, 1993, Pat. No. 5,474,743.

[51] Int. Cl.$^6$ .................................................. G01N 33/20
[52] U.S. Cl. .............................. 436/79; 422/58; 422/68.1; 422/82.05; 422/82.06; 422/82.07; 422/82.08; 422/82.09; 436/73; 436/74; 436/79; 436/163; 436/166; 436/172; 540/468; 540/469; 558/44
[58] Field of Search ............. 422/58, 68.1, 82.05–82.07, 422/82.11; 436/73, 74, 79, 163, 164, 166, 172; 540/468–469; 558/44

[56] References Cited

U.S. PATENT DOCUMENTS

| | | | |
|---|---|---|---|
| 4,008,717 | 2/1977 | Kowarski | 128/214 R |
| 4,504,368 | 3/1985 | Delton et al. | 204/1 |
| 4,577,109 | 3/1986 | Hirschfeld | 250/461.1 |
| 4,640,820 | 2/1987 | Cooper | 422/82.05 X |

(List continued on next page.)

FOREIGN PATENT DOCUMENTS

| | | |
|---|---|---|
| 0 178 775 | 4/1986 | European Pat. Off. . |
| 0 369 733 | 5/1990 | European Pat. Off. . |
| 0 376 168 | 7/1990 | European Pat. Off. . |
| 0 380 664 | 8/1990 | European Pat. Off. . |
| 0 568 380 A1 | 11/1993 | European Pat. Off. . |
| 0 575 712 A2 | 12/1993 | European Pat. Off. . |
| 3 202 779 A1 | 9/1992 | Germany . |
| WO 81/02218 | 8/1981 | WIPO . |
| WO 87/04914 | 8/1987 | WIPO . |
| WO 92/07899 | 5/1992 | WIPO . |
| WO 92/21281 | 12/1992 | WIPO . |
| WO 93/06775 | 4/1993 | WIPO . |
| WO 96/22730 | 8/1996 | WIPO . |

OTHER PUBLICATIONS

"Cation–Responsive Fluorescent Sensors", *Chemosensors of Ion and Molecule Recognition*, B. Valeur, F. Badaoui, E. Bardez, J. Bourson, P. Boutin, A. Chatelain, I. Devol, B. Larrey, J.P. Lefevre, A. Soulet, pp. 195–220.

J.M. Lehn and J.P. Sauvage, "[2]–Cryptates: Stability and Selectivity of Alkali and Alkaline–Earth Macrobicyclic Complexes", *J. Am. Chem. Soc.*, 97, 6700–07 (Nov. 1975).

D. Landini, F. Montanari and F. Rolla, "Phase–Transfer Catalysts: Synthesis and Catalytic Activity of a Tricyclobexyl[2.2.2]cryptand (Perhydrotribenzohexaoxadiaza [8.8.8]eicosane)", *Synthesis*, 223–25 (Mar. 1978).

(List continued on next page.)

*Primary Examiner*—Arlen Soderquist
*Attorney, Agent, or Firm*—F. Andrew Ubel

[57] ABSTRACT

A fluorescent ionophoric compound is disclosed that includes a complexing moiety, such as a cryptand or crown-ether portion, and a fluorescing moiety such as a coumarin portion. The coumarin portion may be substituted at the 3-position with an electron withdrawing or polarizable group such as a substituted aromatic group or a substituted heterocyclic group having a heteroatom in at least one of its alpha positions. The compound, which exhibits good photostability, can be incorporated into cation-sensing composite structures by means of convenient points of covalent attachment.

29 Claims, 12 Drawing Sheets

U.S. PATENT DOCUMENTS

| | | | |
|---|---|---|---|
| 4,762,799 | 8/1988 | Seitz et al. | 436/79 |
| 4,808,539 | 2/1989 | Chapoteau et al. | 436/74 |
| 4,822,746 | 4/1989 | Walt | 436/528 |
| 4,830,013 | 5/1989 | Maxwell | 128/637 |
| 4,859,606 | 8/1989 | Cram et al. | 436/79 |
| 4,929,561 | 5/1990 | Hirschfeld | 436/116 |
| 5,019,350 | 5/1991 | Rhum et al. | 422/82.07 |
| 5,037,615 | 8/1991 | Kane | 422/82.08 |
| 5,045,475 | 9/1991 | Chapoteau et al. | 436/74 |
| 5,081,041 | 1/1992 | Yafuso et al. | 422/82.07 |
| 5,096,831 | 3/1992 | Chapoteau et al. | 436/74 |
| 5,104,623 | 4/1992 | Miller | 422/82.06 |
| 5,136,033 | 8/1992 | Masilamani et al. | 540/468 |
| 5,154,890 | 10/1992 | Mauze et al. | 422/82.07 |
| 5,162,525 | 11/1992 | Masilamani et al. | 540/468 |
| 5,176,882 | 1/1993 | Gray et al. | 422/82.07 |
| 5,187,103 | 2/1993 | Czech et al. | 436/79 |
| 5,439,828 | 8/1995 | Masilamani et al. | 436/74 |
| 5,459,276 | 10/1995 | Kuhn et al. | 436/74 X |
| 5,474,743 | 12/1995 | Tend et al. | 422/85.07 |
| 5,501,980 | 3/1996 | Katerinopoulos et al. | 436/74 |

OTHER PUBLICATIONS

*Organic Syntheses, Collective vol. 5*, 49–51 (1973).

H. Gross, A. Rieche and G. Matthey, *Chem. Ber.*, 96, 308–13 (1963) (translation).

V. Balaiah, T.R. Seshadri and V. Venkateswarlu, "Visible Fluorescence and Chemical Constitution of Compounds of the Benzopyrone Group. Part III. Further Study of Structural Influences in Coumarins", *Proc. Ind. Acad. Sci.*, 16A, 68–82 (Apr. 1942).

W. Borsche and P. Hahn–Weinheimer, *Chem. Ber.*, 85, 198–202 (1952) (translation).

K. Fukui and M. Nakayama, "Synthetic Studies of Sesamol Derivatives. I. A New Synthesis of Ayapin", *Bull. Chem. Soc. Japan*, 35, 1321–23 (Aug. 1962).

E. Bissell, "An Improved Synthesis of Certain 3–Ethoxycarbonylcoumarins", *Synthesis*, 846–48 (Oct. 1982).

E. Kaiser, R. Colescott, C. Bossinger, and P. Cook, "Color Test for Detection of Free Terminal Amino Groups in the Solid–Phase Synthesis of Peptides", *Anal. Biochem.*, 34, 595–98 (1970).

V. Sarin, S. Kent, J. Tam and R. Merrifield, "Quantitative Monitoring of Solid–Phase Peptide Synthesis by the Ninhydrin Reaction", *Anal. Biochem.*, 117, 147–57 (1981).

H. He, H. Li, G. Mohr, B. Kovacs, T. Werner and O. Wolfbeis, "Novel Type of Ion–Selective Fluorosensor Based on the Inner Filter Effect: An Optrode for Potassium", *Anal. Chem.*, 65, 123–127 (Jan. 1993).

Y. Kawabata, T. Imasama and N. Ishibashi, "Fluorimetric Determination of Potassium Ion Using Hexadecyl–acridine Orange Immobilized on a Poly(vinyl chloride) Membrane Attached to a Flow–through Cell", *Anal. Chim. Acta*, 255, 97–101 (1991).

Golchini et al., "Synthesis and Characterization of a New Fluorescent Probe for Measuring Potassium", *Am. Phys. Soc.*, vol. 258, F438–43 (Feb. 1990).

W.R. Sherman et al., *Anal. Chem.*, 1968, 40, 803–805.

M.A. Salam et al. *Anal. Chim. Acta*, 1970, 49, 255–260.

D.P. Specht et al., *Tetrahedron*, 1982, 38, 1203–1211.

A. Göcmen et al., *Pure & Appl. Chem.*, 1993, 447–450.

A. Takadate et al., *Chem. Lett.*, 1993, 811–814.

M.T. Alonso et al., *Tetrahedron Lett.*, 1993, 34, 7465–7468.

W.E. Ohnesurge *Fluoresc. Phosphoresc. Anal.* 1966, 151–167.

E.C. Lim et al. *Chem. Phys. Lett. 1969*, 4, 68–70.

C.–N. Ou et al. *Photochem. Photobiol. 1976*, 24, 487–490.

D. Singh et al. *J. Inst. Chem. (India) 1977*, 49, 191–196.

L.R. Sousa et al. *J. Am. Chem. Soc. 1977*, 99, 307–310.

N. Shimidzu et al. *Chem. Pharm. Bull. 1978*, 26, 191–198.

V. Mikes *Collect. Czech. Chem. Commun. 1979*.

S.L. Shapiro et al. *Springer Ser. Chem. Phys. 1980*.

P.J. Chappell et al. *J. Molec. Spectrosc. 1981*, 87, 316–330.

T. Hirohara et al. *Nippon Kagaku Kaishi 1981*, 477–480.

M. Tada et al. Bull Chem. Soc. Jpn. 1982, 55, 3865–3869.

L.A. DeLisser–Matthews et al. *Analyst 1984*, 109, 1009–1011.

F. Fages et al. *J. Am. Chem. Soc. 1989*, 111 96–102.

M.S.A. Abdel–Mottaleb et al. *J. Photochem. Photobiol. A 1989*, 46, 379–390.

G.M.M. Medeiros et al. *J. Photochem. Photobiol. A. 1993*, 72, 225–233.

I. Leoff et al. *J. Am. Chem. Soc. 1993*, 115, 8933–8942.

L.–D. Li et al. *Anal. Chim. Acta 1994*, 296, 99–105.

D. Marquis et al. *Chem. Phys. Lett. 1994*, 230, 131–136.

R. Crossley et al. *J. Chem. Soc. Perkin Trans. 2 1994*, 513–520.

R. Crossley et al *J. Chem. Soc., Perkin Trans. 2 1994*, 1615–1623.

C. Blackburn et al. *Tetrahedron Lett. 1994*, 35, 7915–7918.

S. Das et al. *J. Phys. Chem. 1994*, 98, 9291–9296.

J. Lu et al. *Analyst 1995*, 120, 453–455.

A. Takadate et al. *Bull. Chem. Soc. Jpn. 1995*, 68, 3105–3110.

CATION-SENSING COMPOSITE STRUCTURE AND COMPOUNDS FOR USE THEREIN

This application is a continuation-in-part of U.S. application Ser. No. 08/521,869 filed Aug. 31, 1995, now abandoned, which is a divisional of U.S. application Ser. No. 08/140,257 filed Oct. 21, 1993, now U.S. Pat. No. 5,474,743.

FIELD OF THE INVENTION

This invention describes fluorescent ionophoric compounds, as well as methods for use thereof, that can be used in the detection of cations, particularly alkali metal cations. This invention also describes cation sensing composite structures that incorporate these compounds and that are useful in continuous sensing applications.

BACKGROUND

Measuring the concentrations of ionic components in various fluids is an increasingly common procedure. Environmental testing procedures can involve frequent, and sometimes continuous, determinations of the concentrations of one or more metal ions, especially ions of heavy metals. Similarly, medical diagnostic and treatment procedures can involve frequent or continuous determinations of the concentrations of one or more ions in one or more bodily fluids of a patient.

The desire for better continuous testing methods continues to grow. With respect to medical procedures in particular, continuous, real time monitoring of serum potassium ion levels in blood and other bodily fluids is highly desirable, especially during heart bypass surgical procedures.

Several methods have been reported for the measurement of metal cation concentrations. Examples include detection based on ion exchange membranes; spectrophotometric and fluorometric techniques involving the presence of reagents; wet electrodes; and ionophore-based detection.

Some of the above methods are not effective in determining alkali metal ion concentrations, however. Among methods commonly used to determine alkali metal ion concentrations are those which monitor various optical properties of solutions containing such ions (or complexes thereof). Of these, techniques measuring fluorescence are preferred over those based on other spectroscopic observations because they enjoy sensitivity and operational advantages based on the intrinsic separation of the excitation (probe) and emission (signal) wavelengths. Compounds useful for in vitro cation concentration determinations have been described in, for example, U.S. Pat. No. 4,808,539, and in *Fluorescent Chemosensors for Ion and Molecule Recognition,* Edited by Anthony Czarnick. These cations include not only alkali metals but also $Ag^+$, $Pb^{2+}$, $Mn^{2+}$, $Zn^{2+}$, $Hg^{2+}$, $Ti^+$, and $Cd^{2+}$.

The use of fiber optic chemical sensors to create in vivo systems has also been described. Examples include incorporation of a chemical sensor into a fiber optic waveguide such that the sensor can interact with the analyte and detect optical changes; use of a tethered pair of fluorescence energy transfer indicators as a chemical sensor in a fiber optic waveguide; use of fiber optics to monitor the signal generated by a substrate-immobilized fluorescer that is sufficiently close to an absorber substance to allow resonant energy transfer to occur; use, of fiber optics to detect fluorescence in a system that includes fluorogenic substances in combination with light-absorbing ligands and light-absorbing complexes; and detection of fluorescence by fiber optics in a system including a solution containing a polymeric cationic material and a fluorescent anionic material in contact, through a semipermeable membrane, with a mobile ionophore selective toward a particular alkali metal ion.

Several fluorimetric methods that potentially can be adapted for in vivo/ex vivo use have been described. For instance, fluorescent probes consisting of rhodamine ester and merocyanine 540 as fluorophores and valinomycin as an ionophore are known. More recently, a fiber optic sensor employing 2,2-bis[3,4-(15-crown-5)-2-nitrophenylcarbamoxymethyl]tetradecanol-14, with Rhodamine-B attached as a fluorophore, to selectively complex potassium ions has been described. This latter device is specifically designed for in vivo use.

Several of the foregoing methods have been beset by deficiencies in sensitivity and selectivity toward alkali metal ions at physiological concentrations, particularly in aqueous media at physiological pH. A method that overcomes some of the selectivity problems, wherein cryptands selectively complex with potassium has been described. The sensitivity of that method is limited. Also, the process must be carried out in an organic solvent in the presence of an organic base, thus not lending itself to continuous blood or fluid determinations.

A family of fluorogenic ionophores based on a 4-methylcoumarin moiety united with various cryptands has also described (U.S. Pat. No. 5,162,525, Masilamani et al.). The [2.2.2] cryptand derivative,

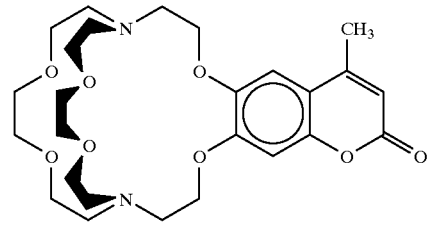

which is selective for the potassium ion, does not suffer from the aforementioned selectivity limitations and allows for potassium ion concentration determination by fluorescence. However, its excitation maximum is near 330 nm, making its use with conventional glass optics components problematical.

RELATED APPLICATION

This is a continuation-in-part of U.S. Ser. No. 08/521,869, which is a division of U.S. Ser. No. 08/140,257 (now U.S. Pat. No. 5,474,743), which are herein incorporated by reference.

SUMMARY OF THE INVENTION

The present invention provides a fluorescent ionophoric compound ("the ionophore") that contains a complexing moiety for binding an ion and a fluorescing moiety. The compound has a wavelength of maximum absorbance of at least about 350 nm. Sensors incorporating these compounds are also described.

Suitable fluorescing moieties preferably contain close-lying $n\pi^*$ and $\pi\pi^*$ excited states. Suitable fluorescing moieties, when coupled to an appropriate complexing moiety, preferably are capable of ion dependent out-of-plane puckering. Also, the $\pi\pi^*$ state of suitable fluorescing moieties preferably is sufficiently high in energy that ion dependent mixing dominates non-radiative coupling to the ground state. Particularly preferred fluorescing moieties include coumarin moieties, although other aromatic carbonyls or nitroaromatics or N-heterocyclic moieties may be employed.

Suitable ion complexing moieties include cyclic "cage" moieties capable of binding an ion. Preferably the cage is capable of selective binding of an ion. Preferred ion complexing moieties include cryptand and crown ether moieties, with cryptand moieties being particularly preferred.

Ions which may be sensed using the compounds of the present invention include, for example, $Ag^+$, $Ba^{+2}$, $Ca^{+2}$, $Ce^+$, $Cd^{2+}$, $Fr^+$, $Hg^{2+}$, $K^+$, $Li^+$, $Mg^{+2}$, $Mn^{2+}$, $Na^+$, $Pb^{+2}$, $Ru^+$, $Sr^{+2}$, $Ti^+$, and $Zn^{2+}$. If desired the compound may be used in conjunction with an ion selective membrane.

In one embodiment, the present invention provides a fluorescent ionophoric compound having the following general formula (Formula "A"):

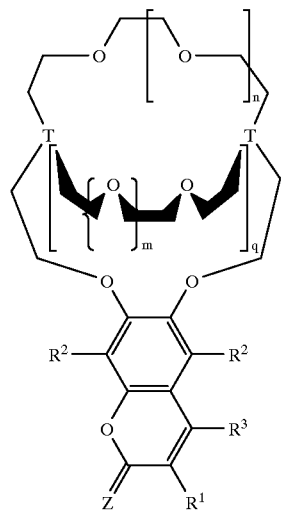

wherein

T is O or N, with the proviso that when T is O, q is 0 and n is 0 to 2, and when T is N, q is 1 and m and n are independently 0 or 1;

each $R^2$ independently is a sterically non-interferring group, including moieties such as hydrogen, halogen, a hydrocarbyl-containing group, a hetero-acyclic group, or a group having the formula $(CH_2X)_aE$ in which X is O, NH, or a single bond, E is a functional group that includes active hydrogen, and a is a whole number from 1 to 100; preferably each $R^2$ group is independently selected from the group consisting of: hydrogen, halogen, a $C_1$–$C_{20}$ alkyl, a $C_1$–$C_{20}$ alkoxy, a $C_2$–$C_{18}$ alkenyl, a $C_1$–$C_{20}$ hydrocarbylamino, a $C_2$–$C_{20}$ di(hydrocarbyl)amino, and a group having the formula $(CH_2X)_aE$ in which X and E are defined as above and a is a whole number from 1 to 25; more preferably each $R^2$ group is independently selected from the group consisting of: hydrogen, halogen, a $C_1$–$C_{10}$ alkyl, a $C_1$–$C_{10}$ alkoxy, a $C_2$–$C_{10}$ alkenyl, a $C_1$–$C_{10}$ alkylamino, a $C_1$–$C_{10}$ dialkylamino, and a group having the formula $(CH_2X)_aE$ in which X and E are defined as above and a is a whole number from 1 to 10; and most preferably each $R^2$ group is independently selected from the group consisting of hydrogen, methyl, ethyl, propyl, butyl, methoxy, ethoxy, propoxy, a $C_2$–$C_{10}$ alkenyl, a $C_1$–$C_{10}$ diaklamino, chlorine, bromine, or a group having the formula $(CH_2X)_aE$ in which X and E are defined as above and a is a whole number from 1 to 3;

$R^3$ is selected from suitable electron-withdrawing and non-electron withdrawing groups. Suitable $R^3$ groups include electron-withdrawing and non-electron withdrawing moieties such as hydrogen, a hydrocarbyl-containing group, a hetero-acyclic group, a heterocyclic group, or a group having the formula $(CH_2X)_bE$ in which X and E are defined as above and b is a whole number from 0 to 100; preferably each $R^3$ group is a non-electron withdrawing group independently selected from the group consisting of: hydrogen, a $C_1$–$C_{20}$ alkyl, a $C_3$–$C_{18}$ cycloalkyl, a $C_6$–$C_{18}$ aryl, a $C_6$–$C_{18}$ aryloxy, a $C_6$–$C_{18}$ hydroxyaryl, a $C_6$–$C_{18}$ arylcarboxy, a $C_6$–$C_{18}$ carboxyaryl, a $C_2$–$C_{18}$ alkenyl, and a group having the formula $(CH_2X)_bE$ in which X and E are defined as above and b is a whole number from 0 to 25; more preferably each $R^3$ group is independently selected from the group consisting of:

hydrogen, a $C_1$–$C_{10}$ alkyl, a $C_5$–$C_8$ cycloalkyl, a $C_6$–$C_{10}$ aryl, a heterocyclic group comprising at least one O, N, or S atom, a $C_2$–$C_{10}$ alkenyl, and a group having the formula $(CH_2X)_bE$ in which X and E are defined as above and b is a whole number from 0 to 10; and most preferably each $R^3$ group is independently selected from the group consisting of: hydrogen, methyl, ethyl, propyl, butyl, a $C_5$–$C_8$ cycloalkyl, a $C_6$–$C_{10}$ aryl, a $C_2$–$C_{10}$ alkenyl, a $C_1$–$C_{10}$ dialkylamino, or a group having the formula $(CH_2X)_bE$ in which X and E are defined as above and b is a whole number from 0 to 3;

$R^1$ is selected from suitable electron withdrawing and polarizable groups, including moieties such as carboxyl, carboxamide, sulfonylaryl, ester, keto-alkyl ester, heterocyclic moieties and aromatic groups (preferably substituted at one or more positions); preferred $R^1$ groups include esters (more preferably ethyl esters), keto-alkyl esters (more preferably —$(CO)CH_2CH_2CH_2(CO)OCH_2CH_3$), and substituted aromatic groups such as substituted phenyls, benzimidazolyls, benzoxazolyls, and benzthiazolyls, and most preferred $R^1$ groups include substituted heterocyclic moieties having the general formula (Formula "C"):

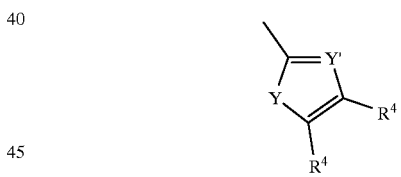

wherein Y and Y' independently are O, S, $NH_x$, or $CH_y$ where x is 0 or 1 and y is 1 or 2, with the proviso that at least one of Y and Y' must be O, S, or $NH_x$, each $R^4$ group is independently selected from the group consisting of hydrogen, halogen, a hydrocarbyl-containing group, a hetero-acyclic group, a heterocyclic group, or a group having the formula $(CH_2X)_cE$ in which X and E are defined as above and c is a whole number from 0 to 100, or both $R^4$ groups together with the carbon atoms to which they are attached form a 5- or 6-membered ring which optionally can have one or more further $R^4$ groups attached; preferably each $R^4$ group is independently selected from the group consisting of: hydrogen, halogen, a $C_1$–$C_{20}$ alkyl, a $C_1$–$C_{20}$ alkoxy, a $C_3$–$C_{18}$ cycloalkyl, a $C_6$–$C_{18}$ aryl, a $C_6$–$C_{18}$ aryloxy, a $C_6$–$C_{18}$ hydroxyaryl, a $C_6$–$C_{18}$ arylcarboxy, a $C_6$–$C_{18}$ carboxyaryl, a $C_2$–$C_{18}$ alkenyl, a $C_1$–$C_{20}$ hydrocarbylamino, a $C_6$–$C_{18}$ arylamino, a $C_6$–$C_{18}$ aminoaryl, a $C_2$–$C_{20}$ di(hydrocarbyl)amino, a heterocyclic group having at least three ring atoms, carboxamide (—C(O)$NR^1R^2$), or a group having the formula $(CH_2X)_cE$ in which X and E are defined as above and c is a whole number from 0 to 25, or both $R^4$ groups together with the carbon atoms to which they are attached form a 5- or 6-membered ring which optionally can have one or more further $R^4$ groups attached; more preferably each $R^4$ group is independently selected from the group consisting of hydrogen, halogen, a $C_1$–$C_{10}$ alkyl, a $C_1$–$C_{10}$ alkoxy, a $C_5$–$C_8$ cycloalkyl, a $C_6$–$C_{10}$ aryl, a heterocyclic group comprising at least one O, N, or S atom, a $C_2$–$C_{10}$ alkenyl, and a $C_1$–$C_{10}$ alkylamino, a $C_1$–$C_{10}$ dialkylamino, or a group having the formula $(CH_2X)_cE$ in which X and E are defined as above and c is a whole number from 0 to 10, or both $R^4$ groups together with the carbon atoms to which they are attached form a 5- or 6-membered ring which optionally can have one or more further $R^4$ groups attached; and most preferably each $R^4$ group is independently selected from the group consisting of: hydrogen, methyl, ethyl, propyl, butyl, methoxy, ethoxy, propoxy, a $C_5$–$C_8$ cycloalkyl, a 5- or 6-membered heterocyclic group comprising at least one O, N, or S atom, a $C_6$–$C_{10}$ aryl, a $C_2$–$C_{10}$ alkenyl, a $C_1$–$C_{10}$ dialkylamino, chlorine, bromine, or a group having the formula $(CH_2X)_cE$ in which X and E are defined as above and c is a whole number from 0 to 3, or both $R^4$ groups together with the carbon atoms to which they are attached form a 5- or 6-membered ring which optionally can have one or more further $R^4$ groups attached; and Z is O or $NR^5$, where $R^5$ is hydrogen or a hydrocarbyl-containing group, more preferably $R^5$ is H or a $C_1$ to $C_4$ alkyl group, and most preferably $R^5$ is H.

In a particularly preferred embodiment for use with blue light sources, the present invention provides a fluorescent ionophoric compound having the general formula (Formula "B"):

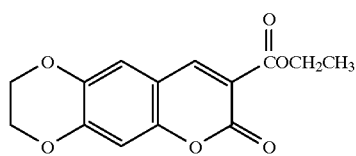

VIII

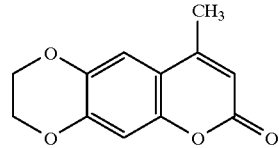

IX

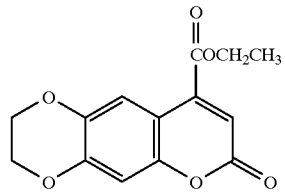

X

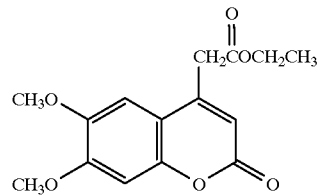

XI wherein
m and n are independently 0 or 1;

Z is O or $NR^5$, where $R^5$ is H or an alkyl group, more preferably $R^5$ is H or a C1 to C4 alkyl group, and most preferably $R^5$ is H;

Y and Y' independently are O, S, $NH_x$, or $CH_y$ where x is 0 or 1 and y is 1 or 2, with the proviso that at least one of Y and Y' must be O, S, or $NH_x$; and $R^2$, $R^3$, and $R^4$ are as defined above for Formula A.
Where this ionophore is to be covalently attached to a substrate, at least one $R^2$ or $R^3$ or $R^4$ group must be something other than H.

In general, compounds of Formula A have a wavelength of excitation of at least about 350 nm and a wavelength of emission preferably of no more than about 500 nm. Compounds of Formula B generally have a wavelength of excitation of at least about 380 nm and preferably at least about 390 nm, and a wavelength of emission of no more than about 500 nm and preferably of no more than about 480 nm. The wavelengths of excitation and emission of these compounds are preferably at least about 10 nm apart, which allow these compounds to be useful in fluoresence-based cation concentration measurement techniques.

In one embodiment, the present invention teaches a class of coumarocryptands. The coumaro[2.2.2]-cryptand ionophore is, in the absence of $Pb^{+2}$ or $Ba^{+2}$, highly selective for $K^+$, while coumarocryptands with different size cryptand cages are highly selective for other mono- and divalent cations. For example, the coumaro [2.2.1]-cryptand is highly selective for $Na^+$ in aqueous solutions having clinically relevant levels of $K^+$ and $Ca^{2+}$. Advantageously, the [2.2.2] coumarocryptands of the present invention maintain high selectivity for $K^+$ when used in aqueous media (that is, the $K^+/Na^+$ complexation ratio is at least 20:1.) When the cryptand portion of the ionophore of the present invention complexes with a cation, the optical properties of the ionophore change in such a way that the concentration of cations in a particular sample can be determined by fluorometric analysis. In a particularly preferred embodiment, substituent groups and their position on the coumarin ring have been chosen so as to ensure that the excitation (i.e., absorption) maximum of the ionophore of the present invention is centered at a wavelength greater than 380 nm. This allows the ionophore of the present invention to be used with solid state light sources such as, for example, blue LEDs and lasers. Substituent groups and their positions are also preferably chosen to keep the emission wavelength below 500 nm, thereby preserving ionophore response for this class of indicators. Finally, substituent groups and their positions are preferably chosen to provide the option for colvalent attachment to substrates. Preferably, the substrate to which the indicator is attached is chosen to support uniform and reproducible ionophore response and to minimize the effect of physiological pH changes on ionophore response.

In a further aspect, the present invention provides a cation sensing composite structure that includes a substrate and the fluorescent ionophoric compound of Formula A or B. Preferably, the ionophoric compound contains at least one E group and the ionophoric compound is covalently bound to the substrate (e.g., through one or more R group) by means of a bond (i.e., E reacts directly with a coreactive group on the substrate) or a separate "linking group" compound that is capable of reacting with both E and a functional group on the substrate to which the ionophore is to be attached. Where a linking group is used, it preferably includes functionalities at both ends with the functionality at one end of the linking group being complementary to E and the functionality at the other end being complementary to a functional group on the substrate. Suitable coupling agents for covalent attachment are described in U.S. Pat. No. 5,053,520, which is herein incorporated by reference. Homobifunctional and/or heterobifunctional coupling agents are described in World Pat. No. WO 96/07268 and WO 96/10747, which are herein incorporated by reference.

In a still further aspect, the present invention provides a method of detecting the presence of a cation comprising the steps of (a) contacting the sensing composite structure with a cation-containing medium that is capable of ion transport and allowing or providing a means for the cations to diffuse to the sensing composite structure to form an equilibrium complex with the fluorescent ionophoric compound of the sensing composite, wherein the ionophoric compound complex, when exposed to light of a wavelength range centered around $\lambda_1$, is capable of emitting light of a wavelength range centered around $\lambda_2$, wherein $\lambda_2$ is at least 10 nm greater than $\lambda_1$, $\lambda_1$ is at least about 350 nm, more preferably at least about 380 nm, and $\lambda_2$ preferably is no more than about 500 nm,; and (b) interrogating the complex with light of a wavelength range centered around $\lambda_1$ for a time sufficient for the complex to emit visible light of wavelength $\lambda_2$ which is collected and detected. By means of suitable algorithms, the amount of emitted light can be correlated with the concentration of the cations in the cation-containing medium.

Definitions

Unless a contrary indication is evident, the following definitions apply herein throughout:

"group" or "compound" or "moiety" means a chemical species that allows for substitution by conventional substituents which do not interfere with the desired product;

"LED" means light emitting diode;

"coumarocryptand" means a coumarin moiety bearing an ortho-fused cryptand moiety, typically at the 6 and 7 positions of the coumarin;

"alkyl" means a straight or branched organic group having from 1 to 30 carbon atoms in the longest chain;

"aromatic" means a ring or fused ring system, having from 5 to 15 carbon or hetero atoms in the ring or rings, the electrons of the rings being delocalized;

"carboxyl" means a carboxylic acid group or a derivative thereof and includes, for example, acid halides, azides, amides, imidazoleamides, esters, and nitrites;

"interrogate" means to expose to a source of excitation radiation and monitor changes in the emission radiation;

"non-electron withdrawing group" means any chemical group that has a Hammett $\sigma_p$ value of 0.2 or less (see, e.g., Hammett Substitution Constants in *Rates and Equilibria of Organic Reactions,* J. E. Leffler and E. Grunwald, p 172 (John Wiley and Sons, NY), the teaching of which is incorporated herein by reference);

"sterically non-interferring group" means any chemical group that does not sterically interfere with the function of the cage;

"close-lying" $n\pi^*$ and $\pi\pi^*$ excited states means an energy separation of less than 1 electron volt (eV) between the $n\pi^*$ and $\pi\pi^*$ excited states.

"high in energy" for a $\pi\pi^*$ state means that the fluorescing moiety is sufficiently high in energy that ion dependent mixing dominates non-radiative coupling to the ground state;

"out-of-plane puckering" for a 6,7-dioxo-substituted coumarin means a molecular vibration involving an unsymmetrical motion of the two exocyclic oxygen atoms (at positions 6 and 7) with respect to the two endocyclic oxygen atoms (at positions 1 and 2);

"fluorescence quantum yield" means fraction of excitation events which result in a fluorescent event;

"Stokes shift" means wavelength difference between emission and absorbance maxima for a fluorescent molecule;

"red shift" means to chemically modify an indicator such that its absorbance shifts to a longer wavelength; and "active hydrogen" means a hydrogen atom attached to a heteroatom such that it is chemically reactive under mild conditions.

DETAILED DESCRIPTION

Figure 1A:
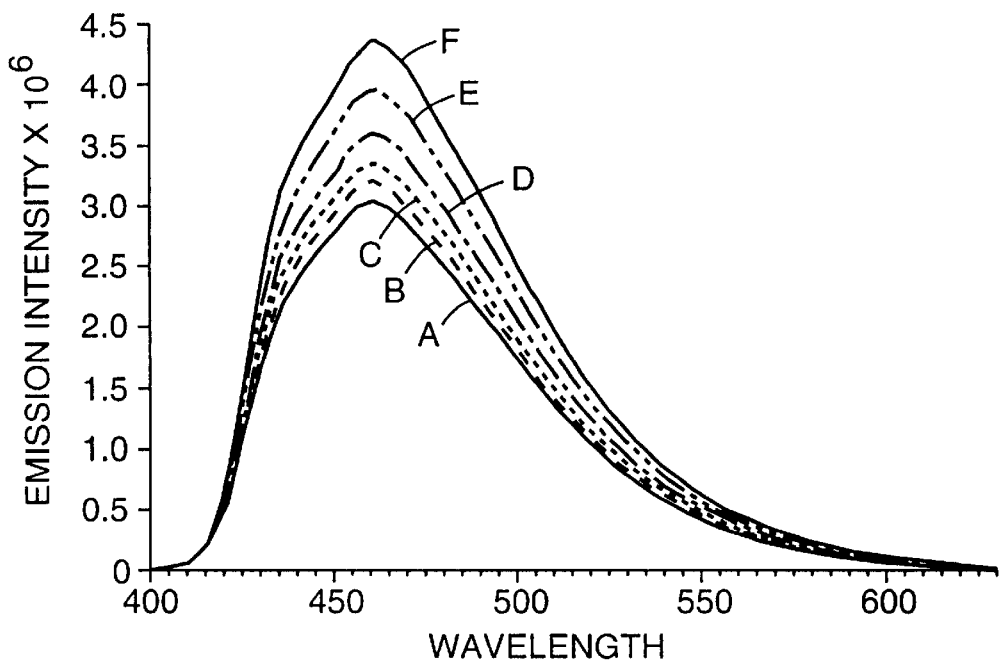
FIGS. 1a, 1b, and 1c show graphical representations of the fluorescence emission response of a coumarocryptand ionophore of the invention (FIG. 1a) and a coumarocryptand of the prior art (FIG. 1b) to increasing concentrations of $K^+$, and a comparison of the response of the coumarocryptands at 0 and 15 mM $K^+$ concentration (FIG. 1c), respectively.

The fluorescent ionophoric compound of the present invention contains (i) a complexing moiety for binding of an ion and (ii) a fluorescing moiety. The compound has a wavelength of maximum absorbance of at least about 350 nm.

In one embodiment, the fluorescent ionophore of the present invention has the general Formula A, shown above. In one presently preferrred embodiment, the fluorescent ionophore of the present invention has the general Formula B, shown above. By placing at the 3-position on the coumarin ring (i.e., $R^1$, Formula A) an electron withrawing or polarizable group, the wavelength of excitation of the ionophore of the present invention can be red-shifted to a point where it can be used in systems employing conventional glass optics.

More preferably, the ionophore is red-shifted to a point where it can be used in systems employing blue light sources. By placing at the 3-position on the coumarin ring a 5-membered heteroaromatic ring with the heteroatom(s) at one or both of the positions alpha to the point of attachment (i.e., the alpha positions), the wavelength of excitation of the ionophore of the present invention can be red-shifted to a point where it can be used in systems employing blue light sources. Preferably, the wavelength of excitation is at least 380 nm, more preferably at least about 390 nm, and most preferably at least about 400 nm.

While the wavelength of excitation preferably is significantly red shifted, the wavelength of emission is preferably no more than about 500 nm, more preferably no more than about 480 nm, and most preferably no more than about 470 nm. For this particular class of compounds the ionophore response appears to decline with increasing emission wavelength, independent of the absorbance wavelength. For emission wavelengths beyond 500 nm, ionophore response for $K^+$ appears to be insignificant. In contrast, ionophore response appears to be optimal for blood parameter monitoring where the emission wavelength is below about 470 nm.

The ionophore of the present invention includes two units (e.g., a cryptand and a coumarin, or a crown-ether and a coumarin) which together allow for the selective sensing of a particular cation.

The complexing moiety (e.g., cryptand or crown-ether moiety) interacts with the cation to be analyzed. Those skilled in the art can recognize which cryptand and crown-ether moieties are useful in complexing particular cations, although reference can be made to, for example, Lehn and Sauvage, "[2]-Cryptates: Stability and Selectivity of Alkali and Alkaline-Earth Macrobicyclic Complexes," *J Am. Chem. Soc.,* 97, 6700–07 (1975), for further information on this topic.

For cryptand cages, the size of the [2.2.2] cage defined by the oxygen and nitrogen atoms (e.g., where m and n in Formula B above both are 1) makes this unit quite selective for cations with a similar diameter (e.g., $K^+$, $Pb^{+2}$, $Sr^{+2}$ and $Ba^{+2}$); the size of the [2.2.1] cage (i.e., one of m and n is 1 while the other is 0) makes it quite selective for cations with a similar diameter (e.g., $Na^+$ and $Ca^{+2}$); and the size of the [2.1.1] cage (i.e., m and n both are 0) makes it highly selective for cations such as $Li^+$ and $Mg^{+2}$. This size selectivity is critical where, for example, physiological samples containing ions in addition to $K^+$ are to be analyzed for [$K^+$]. Advantageously, when these cryptands are to be incorporated into systems that measure physiological concentrations of $K^+$, $Na^+$, or $Li^+$, the heavier metals are unlikely to be present in concentrations which interfere with the analysis of one of these ions. The cryptand group can exist in mono- or diprotonated form depending on the pH of the analyte. Protonation, which occurs at the bridging nitrogens, does not significantly affect the selectivity of the cryptand for $K^+$ (over other metal ions) over the physiological pH range but can affect the combined fluorescence intensity of the cryptand species.

For crown-ether moieties the size of the 15 crown 5 cage defined by the oxygen atoms (e.g., where q is 0, and n is 0 in Formula A) makes this unit suitably selective for $Na^+$; the size of the 18 crown 6 cage (e.g., where q is 0, and n is 1 in Formula A) makes it suitably selective for $K^+$; the size of the 21 crown 7 cage (e.g., where q is 0, and n is 2 in Formula A) makes it quite selective for $K^+$ and nonselective for $Na^+$.

The second specialized unit of the ionophore of the present invention is a fluorescing moiety. The fluorescing moiety can be considered as the "reporting" unit. Using physiological testing as an example, the fluorescing moiety (e.g., coumarin unit) has a characteristic fluorescence intensity versus wavelength plot when a proton, $Na^+$, or some other cation is present in the complexing moiety cage. When a $K^+$ complexes with the oxygen and/or nitrogen atoms of the complexing moiety cage, an increase in fluorescence intensity is observed. In other words, the formation of a potassium complex increases the fluorescence quantum yield of the fluorescing moiety. This same mechanism holds true for other cations for which a particular complexing moiety is selective. Suitable fluorescing moieties include coumarin moieties, although other aromatic carbonyls or nitroaromatics or N-heterocyclic moieties may be employed. Preferred fluorescing moieties include coumarin substituted at the 3-position.

Although the coumarin unit preferably has a carbonyl functionality at the 2-position (i.e., Z is O), the carbonyl functionality can be replaced by an imine functionality (e.g.., Z is NH) without greatly affecting the ionophoric performance. However, if the ionophore of the present invention is to be used in an aqueous acidic environment, this imine functionality can hydrolyze into a carbonyl group.

In the fluorescent ionophore of the present invention, the 3-position of the coumarin unit is substituted with an electron withdrawing or polarizable group (e.g., $R^1$ of Formula A). By locating the substituent at the 3-position, the ionophore of the present invention has somewhat greater (e.g., up to 20% greater) quantum yields than coumarins substituted at the 4-position such as those described by Masilimani et al. This means that a decreased intensity of excitation can be used, thereby reducing the likelihood of photodegradation and allowing lower intensity light sources to be used. Useful electron withdrawing or polarizable groups include carboxyl, carboxamide, sulfonylaryl, ester, keto-alkyl ester, and aromatic groups (preferably substituted at one or more positions). Preferred $R^1$ groups include esters, keto-alkyl esters, heterocyclic moieties and substituted aromatic groups such as substituted phenyls, benzimidazolyls, benzoxazolyls, and benzthiazolyls. Of the esters, ethyl esters are particularly preferred; of the keto-alkyl esters, —(CO)$CH_2CH_2CH_2(CO)OCH_2CH_3$ is particularly preferred. Preferred aromatic group substituents include amines, carboxylic acid, and sulfonic acid. These coumarocryptands generally and preferably have a wavelength of excitation of at least 350 nm. For example, 6,7-O,O-[2.2.2]-cryptando-3-carboethoxycoumarin has a wavelength of excitation of about 354 nm.

The 3-position of the coumarin unit is more preferably substituted by a heteroaromatic group with the heteroatom(s) at one or both of the positions adjacent to the point of attachment to the coumarcocryptand (i.e., the alpha positions). Suitable heteroaromatic groups include 5-membered groups having the general formula (Formula C):

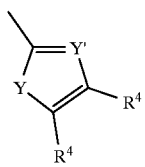

wherein: Y and Y' independently are O, S, $NH_x$, or $CH_y$ where x is 0 or 1 and y is 1 or 2, with the proviso that at least one of Y and Y' must be O, S, or $NH_x$, each $R^4$ group is independently hydrogen, halogen, a hydrocarbyl-containing group, a hetero-acyclic group, a heterocyclic group, or a group having the formula $(CH_2X)_cE$ in which X and E are defined as above and c is a whole number from 0 to 100, or both $R^4$ groups together with the carbon atoms to which they are attached form a 5- or 6-membered ring which optionally can have one or more further $R^4$ groups attached.

Preferably, each $R^4$ group is independently selected from the group consisting of: hydrogen, halogen, a $C_1$–$C_{20}$ alkyl, a $C_1$–$C_{20}$ alkoxy, a $C_3$–$C_{18}$ cycloalkyl, a $C_6$–$C_{18}$ aryl, a $C_6$–$C_{18}$ aryloxy, a $C_6$–$C_{18}$ hydroxyaryl, a $C_6$–$C_{18}$ arylcarboxy, a $C_6$–$C_{18}$ carboxyaryl, a $C_2$–$C_{18}$ alkenyl, a $C_1$–$C_{20}$ hydrocarbylamino, a $C_6$–$C_{18}$ arylamino, a $C_6$–$C_{18}$ aminoaryl, a $C_2$–$C_{20}$ di(hydrocarbyl)amino, a heterocyclic group having at least three ring atoms, carboxamide (—C(O)$NR^1R^2$), or a group having the formula $(CH_2X)_cE$ in which X and E are as above and c is a whole number from 0 to 25, or both $R^4$ groups together with the carbon atoms to which they are attached form a 5- or 6-membered ring which optionally can have one or more further $R^4$ groups attached. More preferably, each $R^4$ group is independently selected from the group consisting of: hydrogen, halogen, a $C_1$–$C_{10}$ alkyl, a $C_1$–$C_{10}$ alkoxy, a $C_5$–$C_8$ cycloalkyl, a $C_6$–$C_{10}$ aryl, a heterocyclic group comprising at least one O, N, or S atom, a $C_2$–$C_{10}$ alkenyl, and a $C_1$–$C_{10}$ alkylamino, a $C_1$–$C_{10}$ dialkylamino, or a group having the formula $(CH_2X)_cE$ in which X and E are defined as above and c is a whole number from 0 to 10, or both $R^4$ groups together with the carbon atoms to which they are attached form a 5- or 6-membered ring which optionally can have one or more further $R^4$ groups attached. Most preferably each $R^4$ group is independently selected from the group consisting of hydrogen, methyl, ethyl, propyl, butyl, methoxy, ethoxy, propoxy, a $C_5$–$C_8$ cycloalkyl, a 5- or 6-membered heterocyclic group comprising at least one O, N, or S atom, a $C_6$–$C_{10}$ aryl, a $C_2$–$C_{10}$ alkenyl, a $C_1$–$C_{10}$ dialkylamino, chlorine, bromine, or a group having the formula $(CH_2X)_cE$ in which X and E are defined as above and c is a whole number from 0 to 3, or both $R^4$ groups together with the carbon atoms to which they are attached form a 5- or 6-membered ring which optionally can have one or more further $R^4$ groups attached.

Restricting the substituent at the 3-position of the coumarin unit to particular 5-membered heteroaromatic ring groups has been found to provide ionophores with excitation maximums that are sufficiently red-shifted (i.e., above at least 380 nm) to allow them to be used with blue light sources.

Solid state light sources such as GaN LEDs mandate the use of fluorescent ionophores with a wavelength of maximum absorption of at least about 380 nm, preferably at least about 390 nm, more preferably at least about 400 nm. Red-shifting of the absorption maximum beyond that provided by prior compounds is necessary. However, not all coumarocryptands with excitation maxima red shifted beyond 350 are useful. For example, 6,7-O,O-[2.2.2]-cryptando-4-cyano-3-carboethoxycoumarin has a wavelength of maximum absorption of about 425 nm but exhibits little or no response in the presence of $K^+$.

Without wishing to be bound by a particular theory, excited state "proximity effects" now are believed to play a role in the fluorescent response of coumarocryptands to cations. Specifically, when the cryptand cage is not complexed with a cation of the appropriate size (i.e., a "target cation"), an out-of-plane puckering vibration of the molecule induces mixing of the emissive $\pi\pi^*$ state with a nearby non-emissive $n\pi^*$ state, thus dampening fluorescence of the ionophore. The puckering involves anti-phase (unsymmetrical) out-of-plane vibration of the two exocyclic oxygens at positions 6- and 7- of the coumarin moiety in concert with anti-phase out-of-plane vibration of the two exocyclic coumarin oxygen atoms. When a target cation is complexed in the cryptand cage, this puckering is inhibited and fluorescence increases. However, where the $\pi\pi^*$ state is too low in energy (i.e., the wavelength of emission is too long), an in-plane vibration can induce direct mixing of the $\pi\pi^*$ state with the ground state, and target cation response can be compromised or lost. This alternative energy dissipation route is believed to be the reason that 6,7-O,O-[2.2.2]-cryptando-4-cyano-3-carboethoxycoumarin and certain other red shifted coumarocryptands exhibit inadequate response in the presence of a target cation.

Based on the above, three guidelines for designing useful ionophores can be derived: (1) the $\pi\pi^*$ and $n\pi^*$ states preferably are close in energy so as to enable mixing thereof; (2) the $\pi\pi^*$ state preferably is sufficiently high in energy (i.e., the wavelength of emission is sufficiently short) so that non-radiative coupling to the ground state does not dominate or compete too strongly with the target cation-dependent mixing of $n\pi^*$ and $\pi\pi^*$ states; and (3) any coumarin substituent used to red shift the coumarocryptand preferably does not inhibit the out-of-plane puckering vibration of the coumarocryptand.

The first of the above guidelines indicates that, while wavelength of maximum absorption is being red shifted, the emission wavelength needs to be prevented from increasing correspondingly, i.e., the Stokes shift needs to be kept relatively low. (Of course, a certain minimum Stokes shift needs to be maintained so that fluorescent detection is possible. Typically, this shift is at least about 10 nm, preferably at least about 20 nm, more preferably at least about 25 nm, and most preferably at least about 30 nm.) The second guideline indicates that the emission wavelength be no more than about 500 nm, preferably no more than about 480 nm, more preferably no more than about 470 nm. The third guideline limits the types of substituents that can be used to red shift the wavelength of maximum absorption. Specifically, the coumarin portion of the ionophore generally cannot have a ring system fused thereto, and the coumarin substituent must red shift the wavelength of maximum absorption to at least 350 nm (more preferably to at least 380 nm) but not red shift the wavelength of maximum emission past 500 nm.

Based on these guidelines, potential coumarin and coumarocryptand candidate molecules were investigated. The study included three model compounds: 6,7-ethylenedioxycoumarin (EDO), 6,7-methylenedioxycoumarin (MDO) and 6,7-dimethoxycoumarin (DMO). The EDO-type compounds were found to be good models for uncomplexed coumarocryptands, since they were shown to support an out-of-plane puckering vibration mode similar to that required for good target ion response in coumarocryptands. The DMO and MDO-type compounds were found to be good models for the complexed coumarocryptands, since they support a planar geometry. As expected, the fluorescence quantum yields for the DMO and MDO-type compounds are greater than those for the corresponding EDO-type compounds. As shown in Table 16e, the DMO/EDO and MDO/EDO quantum yield ratios are a good predictor of the corresponding coumarocryptand ionophore response. These correlations enable one to use molecular orbital calculations for EDO-type and DMO-type compounds to predict the $K^+$ response of corresponding 1coumarocryptands for a variety of red-shifting substituents. Molecular orbital calculations on a number of EDO model compounds (see Table 16c below) indicated that coumarins substituted at the three position with a hetero aromatic ring in which at least one heteroatom is located at an alpha position had the capacity to provide red-shifted absorbances in the desired range of about 390 nm with Stokes shifts in the range of 80 nm.

Preparation of the coumarocryptand ionophore of the present invention is based on a general scheme that is described in detail in U.S. Pat. No. 5,474,743, which is incorporated herein by reference. A typical reaction scheme is presented for convenience. In the following discussion, a bis-chloroethoxy species is shown as a "key intermediate", although any leaving group-terminated bis-ethoxy 2-hydroxybenzaldehyde can be used.

To make the bis-chloroethoxy key intermediate, one can start with 1,2-bis(2'-hydroxyethoxy)benzene, which can be prepared according to the process described by Landini and Montanari in *Synthesis*, 223–25 (1978). This starting material can be converted to 1,2-bis-(2'-chloroethoxy)benzene (I) by reaction with an excess of thionyl chloride. Compound I can be allowed to react with 1,1-dichloromethyl methyl ether in the presence of titanium chloride to produce, upon hydrolysis, 1,2-bis-(2'-chloroethoxy)benzaldehyde (II). The reaction of compound II with hydrogen peroxide and sulfuric acid yields 3,4-bis-(2'-chloroethoxy)phenol (III). Compound III can be treated with 1,1-dichloromethyl methyl ether in the presence of titanium chloride to produce, upon hydrolysis, the aforementioned bischloroethoxy key intermediate species.

The key intermediate can be treated with a cyano-substituted 5-membered aromatic ring compound (wherein Y and Y' are defined as above), followed by reaction with HCl, to produce a 3-(heteroaromatic)-6,7-bis(2'-chloroethoxy)coumarin (IV). After replacement of the chlorines with iodines to provide compound V, that compound can be converted directly to 6,7-[2.2.2]cryptando-3-(heteroaromatic)-coumarin (VI) by reaction with 4,13-diaza-18-crown-6 in a solvent such as acetonitrile. If desired, the ester group can be converted to a carboxylic acid group by acid hydrolysis so as to provide compound VII.

These reactions are summarized in the Scheme shown below.

Reaction Scheme

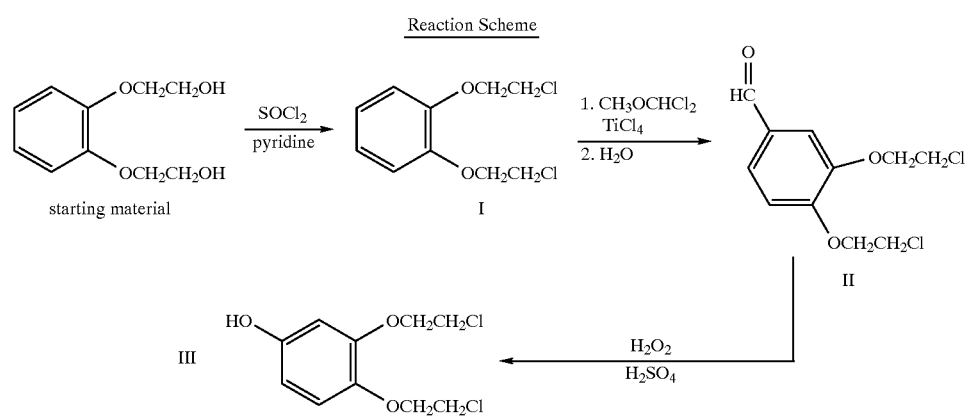

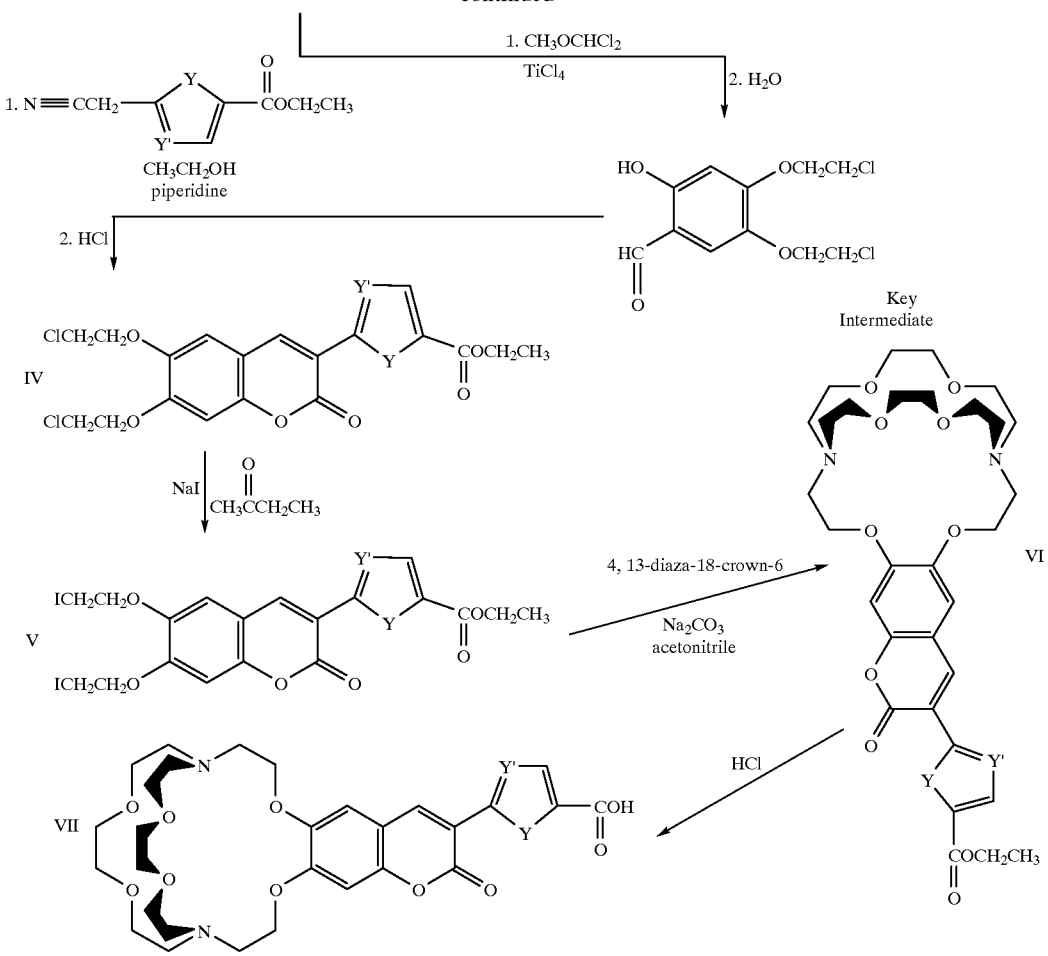

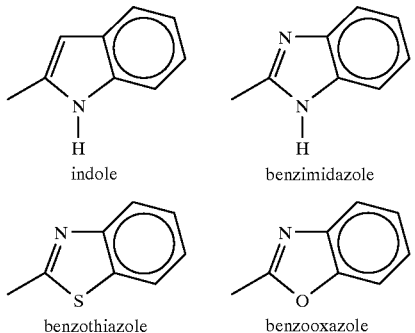

Those skilled in the art will recognize that coumarocryptands other than the [2.2.2] species can be prepared by using diaza crown ethers other than 4,13-diaza-18-crown-6. For instance, where a [2.2.1] coumarocryptand is desired, 1,4,10-trioxa-7,13-diazacyclopentadecane can be used. See Examples 18 and 20 infra for further details.

A preferred 5-membered aromatic ring having a heteroatom at least one of its alpha positions is a furan (e.g., Y is O and Y is CH). Other useful 5-membered aromatic ring groups include, but are not limited to

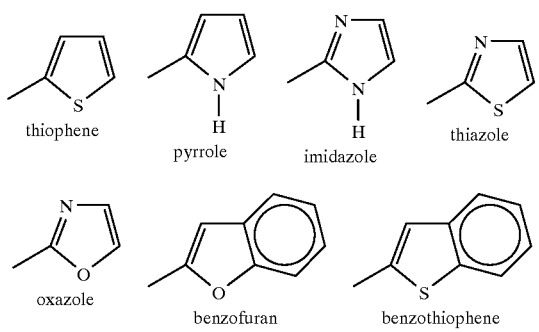

Based on the foregoing discussion of guidelines relating to electronic states, one skilled in the art can see that, with reference to the compound of Formula A, selection of $R^1$, $R^2$, and $R^3$ groups is important.

$R^1$, which is particularly important in its contribution to the red-shifting of the compound, has been previously discussed.

Suitable $R^2$ groups include any sterically non-interferring groups. Suitable groups include moieties such as hydrogen, halogen, a hydrocarbyl-containing group, a hetero-acyclic group, or a group having the formula $(CH_2X)_aE$ in which X and E are defined as above and a is a whole number from 1 to 100. Preferably each $R^2$ group is independently selected from the group consisting of: hydrogen, halogen, a $C_1$–$C_{20}$ alkyl, a $C_1$–$C_{20}$ alkoxy, a $C_2$–$C_{18}$ alkenyl, a $C_1$–$C_{20}$ hydrocarbylamino, a $C_2$–$C_{20}$ di(hydrocarbyl)amino, or a group having the formula $(CH_2X)_aE$ in which X and E are defined as above and a is a whole number from 1 to 25. More preferably each $R^2$ group is independently selected from the group consisting of: hydrogen, halogen, a $C_1$–$C_{10}$ alkyl, a $C_1$–$C_{10}$ alkoxy, a $C_2$–$C_{10}$ alkenyl, and a $C_1$–$C_{10}$ alkylamino, a $C_1$–$C_{10}$ dialkylamino, or a group having the formula $(CH_2X)_aE$ in which X and E are defined as above and a is a whole number from 1 to 10. Most preferably each $R^2$ group is independently selected from the group consisting of: hydrogen, methyl, ethyl, propyl, butyl, methoxy, ethoxy, propoxy, a $C_2$–$C_{10}$ alkenyl, a $C_1$–$C_{10}$ dialkylamino, chlorine, bromine, or a group having the formula $(CH_2X)_aE$ in which X and E are defined as above and a is a whole number from 1 to 3.

Many different groups may be selected for $R^3$. Preferred $R^3$ groups include any non-electron withdrawing groups. Suitable groups include non-electron withdrawing moieties such as hydrogen, a hydrocarbyl-containing group, a heteroacyclic group, a heterocyclic group, or a group having the formula $(CH_2X)_bE$ in which X and E are defined as above and b is a whole number from 0 to 100. Preferably each $R^3$ group is a non-electron withdrawing group independently selected from the group consisting of hydrogen, a $C_1$–$C_{20}$ alkyl, a $C_3$–$C_{18}$ cycloalkyl, a $C_6$–$C_{18}$ aryl, a $C_6$–$C_{18}$ aryloxy, a $C_6$–$C_{18}$ hydroxyaryl, a $C_6$–$C_{18}$ arylcarboxy, a $C_6$–$C_{18}$ carboxyaryl, a $C_2$–$C_{18}$ alkenyl, or a group having the formula $(CH_2X)_bE$ in which X and E are defined as above and b is a whole number from 0 to 25. More preferably each $R^3$ group is independently selected from the group consisting of:

hydrogen, a $C_1$–$C_{10}$ alkyl, a $C_5$–$C_8$ cycloalkyl, a $C_6$–$C_{10}$ aryl, a heterocyclic group comprising at least one O, N, or S atom, a $C_2$–$C_{10}$ alkenyl, or a group having the formula $(CH_2X)_bE$ in which X and E are defined as above and b is a whole number from 0 to 10. Most preferably each $R^3$ group is independently selected from the group consisting of hydrogen, methyl, ethyl, propyl, butyl, a $C_5$–$C_8$ cycloalkyl, a $C_6$–$C_{10}$ aryl, a $C_2$–$C_{10}$ alkenyl, a $C_1$–$C_{10}$ dialkylamino, or a group having the formula $(CH_2X)_bE$ in which X and E are defined as above and b is a whole number from 0 to 3.

Where the ionophoric compound of the present invention is to be attached to a substrate, at least one R group must include a functional group having an active hydrogen (i.e., an E group). Inclusion of such a group allows for reaction with a coreactive functional group so as to form a covalent bond.

Preferably, each $R^2$ and $R^3$ is hydrogen, and $R^1$ is a substituted aromatic moieties having the general formula (Formula "C"):

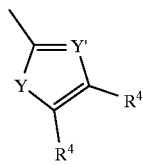

wherein Y and Y' independently are O, S, $NH_x$, or $CH_y$ where x is 0 or 1 and y is 1 or 2, with the proviso that at least one of Y and Y' must be O, S, or $NH_x$, one $R^4$ is hydrogen, and the other $R^4$ is a carboxylic acid group.

A particularly preferred ionophore of the present invention for the detection of $K^+$ has the formula

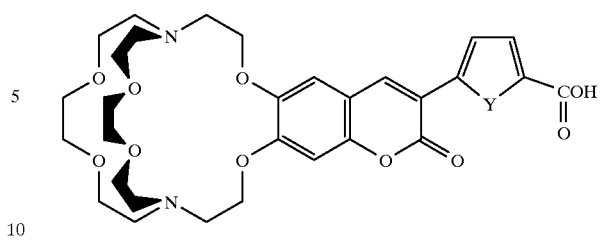

where Y is O, S, or NH, especially where Y is O.

When at least one of $R^1$, $R^2$, and $R^3$, or at least one $R^4$ group, is a group that includes an active hydrogen, the fluorescent ionophore of the present invention has a convenient means of covalent attachment to other molecules and/or substrates. The ionophore of the present invention can be attached to a substrate either directly or through a molecular tether (i.e., a linking group) to form sensing compositions, which then can be incorporated into continuous sensing or flow-through devices.

Where the ionophore of the present invention is to be attached to a substrate through such a linking group, the longest continuous chain thereof preferably includes 5 to 125 carbon and/or hetero atoms such as oxygen, nitrogen, sulfur, etc., more preferably 10 to 70 carbon and/or hetero atoms, and most preferably 5 to 15 carbon and/or hetero atoms, with a free functionality on at least one end thereof These linking groups preferably are hydrophilic so as to not interfere with the capacity of metal ions to interact with the ionophores. However, if it is desired that the linking groups contribute to a different physical property of the system (e.g., hydrophobicity, negative charge, etc.) or if the substrate is sufficiently hydrophilic, the repeating units and end group functionalities can be modified accordingly.

The functionalities of these linking groups can be chosen so as to selectively react with one of the R groups of the coumarocryptand. Possible functional groups include amines, amides, esters, oxiranes, olefins, ureas, isocyanates, thioisocyanates, carbamates, sulfonic acid, sulfonamides, sulfonyl chlorides, carboxylic acid, carboxyls, silanols, chlorotriazines, hydrazines, hydrazides, and aldehydes (or groups which, upon reaction with one of the R groups of the coumarocryptand, form amines, amides, esters, ethers, ureas, urethanes, sulfonamides, silanes, and hydrazides).

The linking groups preferably can be attached to the substrate before reaction with the ionophores. This can be done in one of two ways. First, they can be reacted with the substrate before attaching the ionophores. If this option is chosen, each linking group is preferably bireactive (i.e., have a functional group, either the same or different, on each end of each tether), and the substrate preferably has complementary functionalities that can react with one of the functional groups of the tethers. Second, the substrate can be formed with linking groups preattached, which involves, e.g., selecting a substrate polymer so that linking groups are already appended.

Where the ionophore of the present invention is to be immobilized on a substrate (i.e., either directly or through a linking group) to form a sensing composite structure, substrates of various forms can be employed. Where the sensing composite is to be included in a continuous monitoring device, a planar substrate probably will be preferred, simply because of the dimensions and geometry of the device.

Examples of planar substrates or substrates that can readily be made planar include free-standing polymers in the form of a membrane or film, and coatable polymers (i.e., polymers that can be coated on a support). Free-standing membranes be formed from various polymers including polyethylene, polypropylene, polyvinylidene chloride, polyvinylchloride (PVC), polysulfone, cellulose, functionalized cellulose, and nylon, and from silica, such as a silica xerogel or porous glass. (Some nylon membranes provide poorly reversible composites, i.e., composites that can be used for only a few cycles between high and low cation concentration before slowly ceasing to show changes in intensity with changing metal ion concentration.) Useful substrates are preferably ion permeable and optionally are finctionalized with, or have been treated (e.g., air oxidized) so as to intrinsically carry, groups that are complementary to and react with the functionality of the R group.

To achieve as high a concentration of ionophores as possible where they are to be attached to the surface of a substrate, it may be desirable to use a porous substrate or membrane, or to roughen the surface of the membrane, particularly such as those comprising silica, prior to attaching the ionophores.

Water-insoluble coatable polymers are a preferred substrate. Such polymers include polyvinylchloride (PVC), copolymers and terpolymers of vinyl chloride, copolymers of styrene and at least one of maleic acid and maleic anhydride, copolymers of alkyl vinyl ether and at least one of maleic acid and maleic anhydride, polymers and copolymers of vinyldimethyl azlactone, and copolymers of one of acrylate- and methacrylate esters (or acrylamides and methacrylamides) with one of acrylic acid and methacrylic acid. Once the ionophores of the present invention have been covalently attached to one of these polymers (either directly or through linking groups), the polymer—ionophore composite optionally can be spread on one of the membranes described above. Alternatively, a membrane can be coated with a coatable polymer (optionally reacted with linking groups) and then allowed to react in a solution of an ionophore of the present invention. When either is done, the substrate is the membrane plus the coatable polymer bearing the ionophore.

A particularly preferred composite structure is a preformed substrate, optionally coated with a polymer, that has been reacted with (either directly or through a tether) a 3-substituted coumarocryptand of the present invention. Of available preformed polymeric substrates, preferred examples include hydrophilic porous polypropylene (HPPP) overcoated with PVC, as described in PCT patent publication WO 92/07899 which is herein incorporated by reference. Also preferred is hexanediamine (HDA)-functional cellulose that has been overcoated with carbon black.

Those skilled in the art will recognize that, by selecting a substrate or membrane that is selectively permeable for protons (or the hydronium ion), a composite structure that acts as a pH sensor in the presence of varying concentrations of metal ions can be prepared. Where a constant concentration of metal ions is maintained, such a selective membrane might not be needed.

Where a flow-through device is to be employed, a solid composite structure can, for example, be ground into a powder (or the coumarocryptand compound can be attached to commercially available powders or beads) or encapsulated in an ion permeable matrix such as a hydrogel, an acrylamide, or an acrylate-type gel. If the composite structure is a powder (or is ground into a powder), it can be adhered to a planar substrate if so desired.

Where continuous sensing is desired, the substrate preferably either does not interact with or does not allow for reversible interaction with cations in its vicinity so that the ions can easily form reversible complexes with the attached ionophores, regardless of the particular substrate geometry. To minimize interference with the cation/ionophore equilibrium, the substrate material chosen preferably interacts with cations in such a way that the reversibility of this interaction is not significantly modified when the concentration of cations changes. The substrate itself preferably does not irreversibly react with or adsorb cations, has a net negative charge, and is hydrophilic. If the substrate chosen does not intrinsically possess these preferred characteristics, it can be modified so that it does. For instance, sulfonate or phosphate groups can be attached along with the aforementioned linking groups to impart to the composition an overall negative charge and to increase its hydrophilicity.

Where the sensing composition is to be used in a device where cations must diffuse through the substrate in order to reach the attached ionphores, the substrate necessarily will be at least somewhat ion permeable or microporous. Additionally, depending on whether (and how) an interrogation beam of light is to be used, it may be desirable to provide a translucent or transparent substrate and an opaque, reflecting, or light absorbing overcoat. Typical overcoats include a dispersion of carbon black or other pigment in a carrier, such as a polymer or suitable solvent. The overcoat can be coated on the substrate bearing a sensing composition of the invention.

If the concentration of cations in the analyte solution is to be quantitatively determined, an analytical technique that can measure the equilibrium ion—ionphore complex concentration is preferred. Spectroscopic methods have been found to be especially useful. Particularly preferred is fluorescence. Such a method optionally can be modified so as to employ fiber optics in the transmission of excitation and emitted light. For instance, one or more optical fibers can be used to introduce interrogating light of a wavelength range centered around an excitation wavelength $\lambda_1$, and to transport to a detector emitted light of a wavelength range centered around an emission wavelength $\lambda_2$.

While systems that employ lamp sources have proven commercial utility, solid state LED and laser diode sources are preferred. These solid state sources generally increase reliability, reduce cost and size, and improve noise/drift characteristics of the opto-electronics system. GaN blue LED's introduced by Nichia Chemical Industries of Japan has enabled the development of a practical LED-based electro-optics system for polyaromatic hydrocarbon based fluorescent indicator systems. In particular, the blue tail of the GaN LED emission (390–420 nm) can be mated to the absorbance maxima of the herein disclosed red-shifted ionophores. Furthermore, new GaN laser diodes emit at 405 nm and can be modulated at frequencies sufficient to support phase modulation based ionophore sensing.

Fluorescent ionophoric compounds of the present invention can be used in a variety of applications wherein determination of the concentration of a particular cation is desired. Ionophores selective for $K^+$ or $Na^+$ are particularly useful in the determination of concentrations of these ions, especially in biological systems. These ionophores can be incorporated into existing testing kits, coated onto various substrates, and incorporated in fiber optic-based analytical instruments. Ionophores selective for $Pb^{+2}$ can be useful in environmental and perhaps even biological testing. By confining coumarocryptand ionophores that have a $pK_a$, preferably a $pK_a$ for the diprotonated species, near the pH of interest in a suitably buffered water-filled compartment inside (or, perhaps, behind) a silicone rubber or similarly gas-permeable membrane, one can also determine $[CO_2]$ (i.e., the ionophore can interact with acidic species generated by the hydration of $CO_2$ to $H_2CO_3$). Other detection and concentration determination applications using these ionophores will be apparent to those skilled in the art.

Figure 4A:
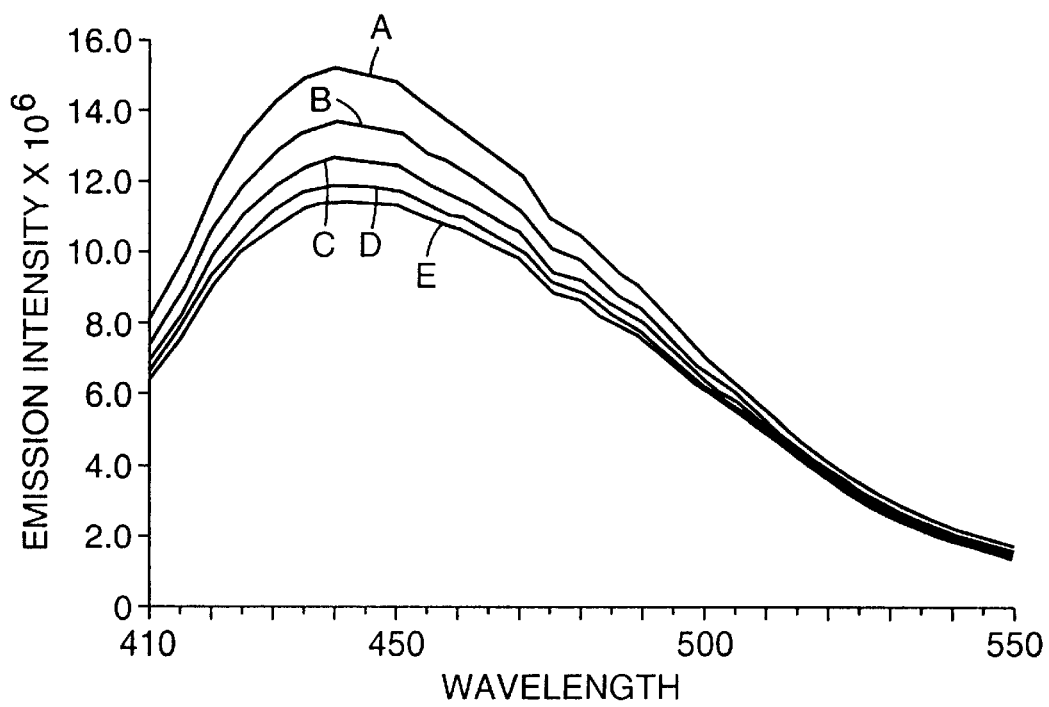
FIGS. 4a and 4b show a graphical representation of the effect of changing pH of the physiological medium in which potassium concentration is to be measured, for a coumarocryptand ionophore of the invention (FIG. 4b) and a prior-art coumarocryptand (FIG. 4a)

A particular advantage of composite structures of the present invention is the lack of influence of pH on their fluorescence intensity. For example, the change in fluorescence intensity of such a sensing composite structure over a pH range of from about 6.98 to about 7.8, which encompasses the physiological pH range (7.3 to 7.5), at a physiological $K^+$ concentration of about 4 mM, was only about 6% of the total fluorescence intensity (see FIG. 4b). In contrast, a prior-art coumarocryptand described in U.S. Pat. No. 5,474,743 exhibited a fluorescence intensity change of about 33% over the same pH range (FIG. 4a).

In a particularly preferred embodiment, the ionophore is incorporated into a cassette, including cassettes as described in U.S. Pat. Nos. 4,640,820 and 4,786,474, each of which is hereby incorporated by reference, that is part of a system for measuring one or more parameters of a fluid such as blood. Preferably, the ionophore is covalently bonded to a membrane that is further incorporated into a multi-layer assembly that can be adhesively attached to the cassette. Such a multi-layer assembly can include a pressure-sensitive adhesive layer having a release liner (e.g., poly (ethyleneterephthalate), PET, as is known in the adhesive art) attached to one side thereof and, on the side opposite the adhesive, a thin, flexible membrane such as PVC or polycarbonate. The sensing substrate, preferably comprising a carrier substrate such as HPPP or modified cellulose on which has been coated or to which has been covalently bound a sensing ionophore of the invention, is attached by adhesive or lamination to the flexible membrane. Preferably, at the outermost side of this multi-layer assembly (e.g., on the exposed surface of the sensing substrate), an opacifying coating covers the sensing substrate. The individual layers have been discussed, supra.

Cassettes useful in fluid parameter measurement systems such as previously described can be of at least two types: flow-through or shunt. Flow-through cassettes can be useful for sensing in an arterial or venous passageway, whereas shunt cassettes can be useful for sensing in a shunt passageway, for example in an open-heart surgery operation. Shunt passageways include a means for diverting some blood from a patient into a circuit that is connected to but separate from the main heart-lung circulation circuit. The one-piece cassette assembly described below preferably is used in shunt passageways, since it is typically has a smaller fluid chamber, is easily detached from the system, and can be sterilized by conventional autoclaving methods. Advantageously, multi-layer sensing assemblies incorporating coumarocryptand ionophores of the invention exhibit substantially the same ion response and spectral characteristics before and after autoclave sterilization (approximately 120° C.).

Flow-through cassettes allow passage of fluid along the arterial and venous passageways to remain uninterrupted prior to monitoring. Flow-through cassettes typically have larger-diameter inlet aned outlet passages so as not to restrict blood flow. When used, a semi-permeable membrane seals an upper, open portion of a flow-through casing that is sealably connected to a body having incorporated therein one or more calibrated sensing membranes, as described in the present invention. The sensing body preferably is connected to a measuring device such as device 200 of FIG. 11 described in detail below. Once fluid parameters have been measured, the cassette is removed from device 200 and discarded. Flow-through cassettes typically are not intended to be autoclaved.

Figure 11:
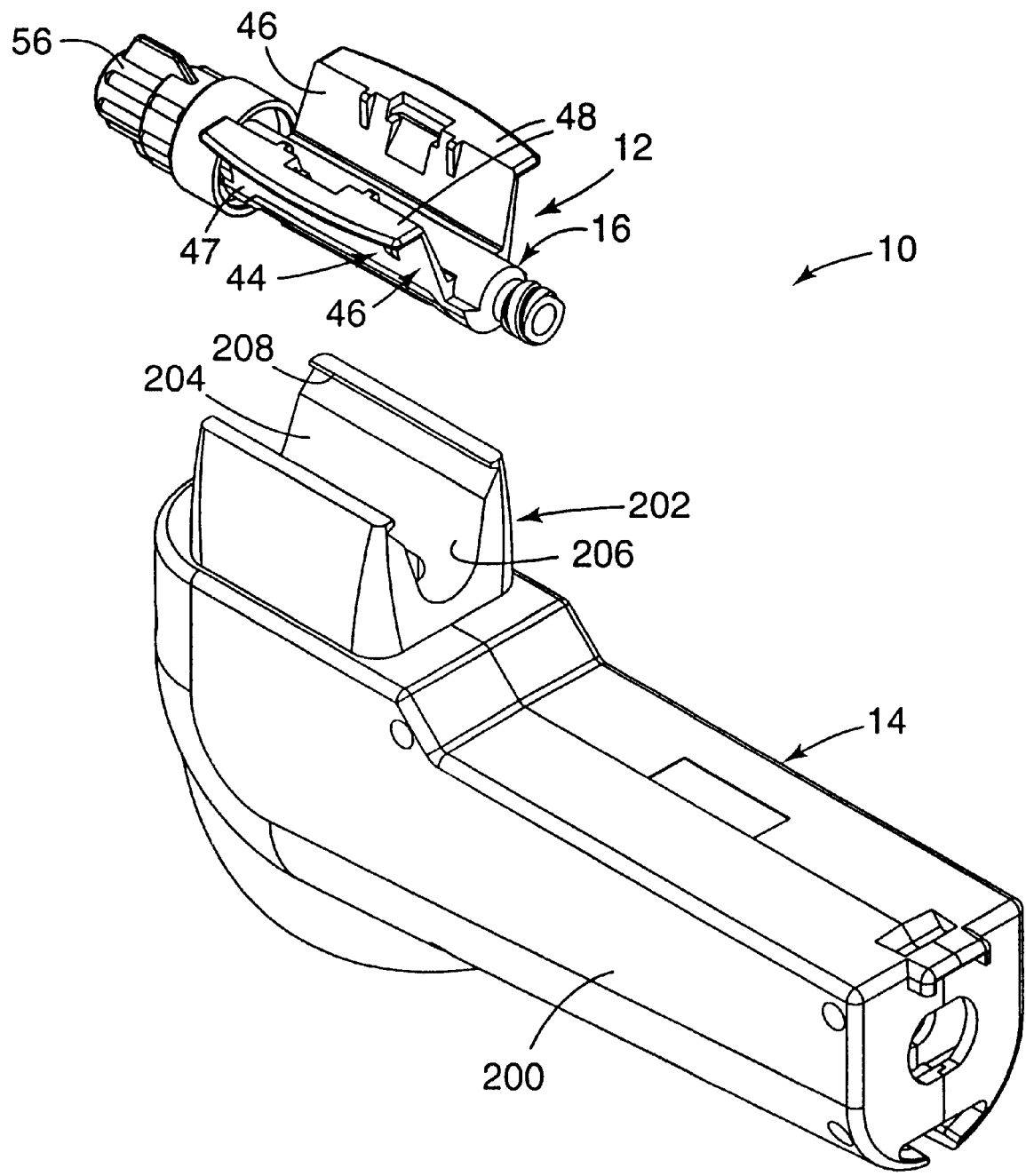
FIG. 11 is a perspective view of a calibration and fluid parameter measurement cassette along with a fluid parameter measuring device that may employ coumarocryptand ionophores of the invention.

A system 10 for measuring one or more characteristics or parameters of fluid such as blood is illustrated in FIG. 11. System 10 broadly includes a cassette 12 that receives the fluid along with a measuring device 14 for measuring parameters of fluid in cassette 12.

Figure 12:
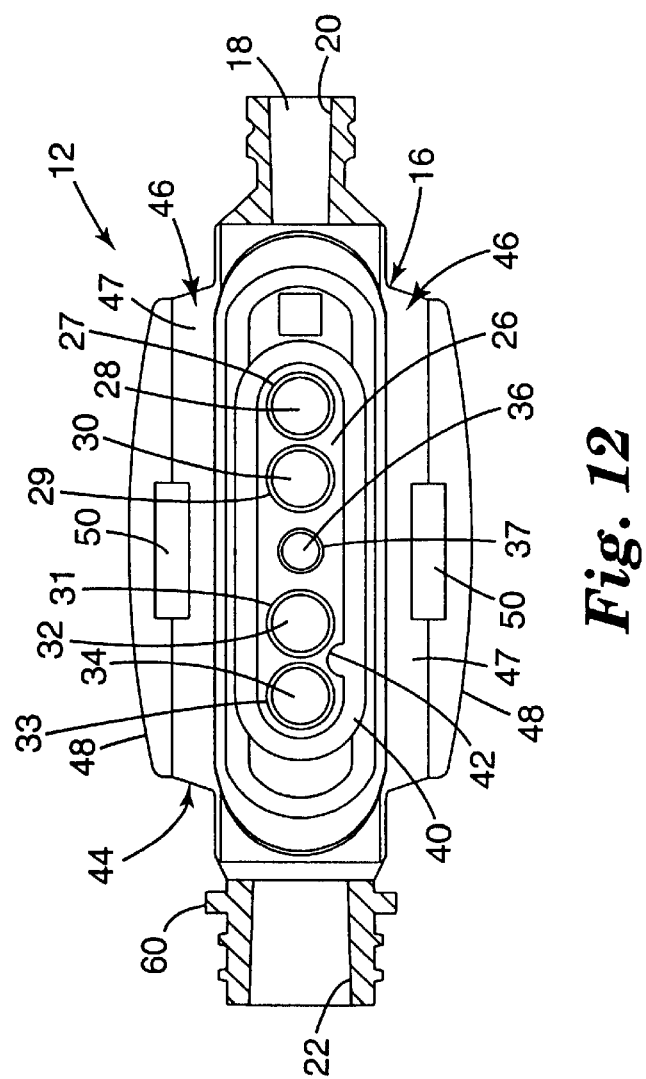
FIG. 12 is an enlarged elevational view in partial section of the measurement cassette shown in FIG. 11, looking toward a side of the cassette that faces the measuring device when the cassette and the device are coupled together.

Cassette 12 is shown in more detail in FIG. 12, and includes an elongated casing 16 having wall sections defining an elongated, internal, flow-through fluid chamber 18 that extends along the longitudinal axis of casing 16. Fluid chamber 18 includes a first portion 20 having a first or "inlet" port for admitting fluid into chamber 18, a second portion 22 having a second or "outlet" port for allowing fluid to exit fluid chamber 18 and a central portion located between portions 20, 22. (Although the description that follows refers to fluid flowing into chamber 18 through he first portion 20 and discharged from chamber 18 through second portion 22, it should be understood that the fluid may also flow if desired in an opposite direction through chamber 18 such that the fluid enters chamber 18 through the second port and exits through the first port).

An external side of casing 16 includes a central section with a generally oval-shaped recess 26. At least one sensor for determining one or more parameters of fluid in chamber 18 is carried by casing 16. In the embodiment shown, a series of four sensors is located between recess 26 and middle portion 24 of fluid chamber 18, and the sensors are placed in four cavities that are arranged in aligned, spaced-apart relationship along the longitudinal axis of casing 16. As depicted in FIG. 4, the sensors include a potassium sensor 28, a pH sensor 30, and carbon dioxide sensor 32 and an oxygen sensor 34 that are received in cavities 27, 29, 31, 33 respectively.

A hole in casing 16 is located between pH sensor 30 and carbon dioxide sensor 32. A thermocouple-receiving well 36 is fixed to casing 16 and extends over the hole. Well 36 has a hat-shaped configuration with a brim that is bonded by an adhesive to wall sections of casing 16 that face central portion 24 of fluid chamber 18. A suitable adhesive is an acrylic urethane adhesive such as "UV Cure" brand adhesive from Loctite Corporation. Well 36 is preferably made of a corrosion-resistant material having a thermal conductivity similar to metal, such as 0.004 inch (0.1 mm) thick titanium. Well 36 protrudes into central portion 24 of fluid chamber 18 to provide intimate thermal contact with fluid therein.

Casing 16 also includes a generally oval-shaped rim 40 that circumscribes recess 26 and extends outwardly in a direction away from the longitudinal axis of casing 16. As can be appreciated by reference to FIG. 12, the major axes of oval-shaped recess 26 and surrounding rim 40 coincide and extend across the center of sensors 28, 30, 32, 34 and well 36 and are also parallel with the longitudinal axes of casing 16 and fluid chamber 18.

A semi-cylindrical alignment key 42 is integrally connected to an inner wall of rim 40. Preferably, alignment key 42 is oriented such that a reference plane that is perpendicular to the longitudinal axis of casing 16 and extends equidistant between sensor 32 and sensor 34 also bisects key 42 along its central diametrical plane.

Cassette 12 further includes a first, male coupling 44 for detachably connecting casing 16 to measuring device 14. Coupling 44 has a convex, generally U-shaped configuration in directions perpendicular to the longitudinal axis of casing 16. Coupling 44 includes the aforementioned central section of casing 16 and opposed leg portions 46 that extend outwardly from casing 16 in a direction away from the direction of outward extension of rim 40. Each leg portion 46 includes a pair of support sections having a flat, coplanar outer surface 47 that are parallel to the outer side of respective leg portion 46. Preferably, outer surfaces 47 of opposed leg portions 46 converge as casing 16 is approached and extend along respective reference planes that are oriented at an angle in the range of about 28 degrees to about 32 degrees relative to each other. More preferably, outer surfaces 47 extend along respective reference planes that are oriented at an angle of about 30 degrees relative to each other.

A flange 48 is integrally connected to the outer end of each leg portion 46. Flanges 48 lie in a common reference plane that is parallel to the longitudinal axis of casing 16. Leg portions 46 are somewhat flexible and can be moved slightly toward each other under the influence of finger pressure, but also have sufficient memory to quickly and repeatedly return to their original, normal orientation once finger pressure is released.

An outer, central end region of each leg portion 46 is integrally connected to a wedge-shaped tab 50 that lies between the support sections. Tabs 50 extend away from each other and outwardly from respective leg portions 46 along respective reference planes that are oriented at an angle of about 80 degrees relative to each other. Additionally, a distal edge of each tab 50 extends in a reference plane that is oriented at an angle of 25 degrees relative to the direction of extension of flanges 48. The outermost edges of tabs 50 are spaced outwardly relative to adjacent regions of respective leg portions 46 and lie in a common reference plane that is between the longitudinal axis of casing 16 and the aforementioned reference plane containing flanges 48.

Figure 13:
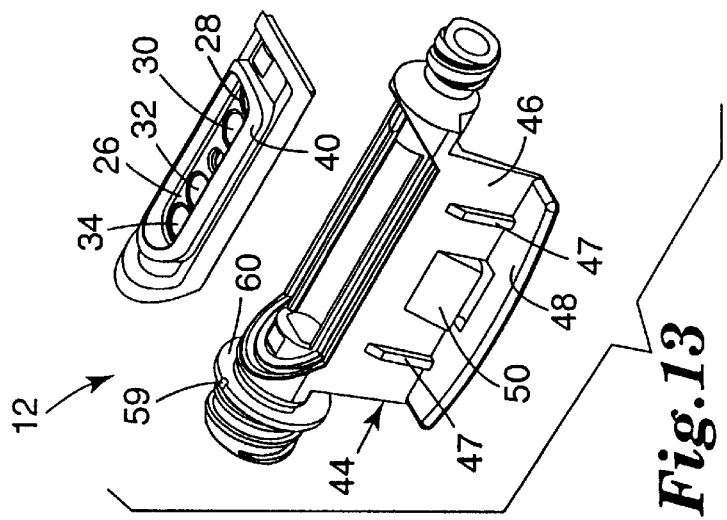
FIG. 13 is an exploded, perspective view of the cassette alone that is shown in FIG. 11, from a different view, illustrating a two-piece construction of the cassette for exemplary purposes.

Preferably, casing 16 is made of a relatively clear plastic material such as medical grade polycarbonate, and is constructed of two or more initially separate pieces that are injection-molded and then joined together. An example of a suitable two-piece construction is shown in FIG. 13. In FIG. 13, one piece of casing 16 includes recess 26 and rim 40, and carries sensors 28, 30, 32, 34 and the second piece includes leg portions 47, inlet and outlet ports and other elements as shown. The pieces may be connected together by ultrasonic welding, solvent welding or adhesive bonding. Of course, other constructions (such as an integral, one-piece construction or a three-piece construction) are also possible.

As illustrated in FIGS. 11–13 casing 16 has a first external threaded section that surrounds the inlet port of first portion 20. The first threaded section is preferably constructed to matingly connect to an internally threaded Luer-type connector when cassette 12 is in use for measuring parameters of fluid flowing through chamber 18. Connector 52 preferably has a ribbed portion for providing an interference-fit coupling to a section of flexible tubing that may direct fluid toward chamber 18.

A second external threaded section surrounds the outlet port of second fluid chamber portion 22. As shown in FIG. 11, fitting 56 has an internal threaded section that matingly receives the second threaded section. Fitting 56 optionally includes a rearwardly extending collar having a radially inwardly extending rib. Casing 16 has a circumscribing, radially outwardly extending rib 60 adjacent the second threaded section that functions as a stop and provides a physical interference to the rib in order to prevent detachment of fitting 56 under normal circumstances whenever fitting 56 is partially unthreaded from casing 16.

Measuring device 14 includes a two-part elongated housing 200. The two parts could be held by internal barbed connectors (for snap-together assembly) or by screws. Preferably, housing 200 is made of an impact-resistant plastic material such as a mixture of polycarbonate and acrylonitrile-butadiene-styrene ("ABS") polymer, and has a smooth outer surface for facilitating disinfection. Optionally, the inner surface of the housing 200 is coated with an electromagnet-compatible material.

Measuring device 14 includes a second, female coupling 202 that is optionally made of a metallic material such as anodized aluminum. Coupling 202 has a concave recess with a generally U-shaped configuration in directions perpendicular to the longitudinal axis of housing 200. The recess includes two flat, opposed sidewall sections 204 that are interconnected by a central bight section 206. Preferably, opposed sidewall sections 204 converge as bight section 206 is approached and extend along respective reference planes that are oriented at an angle in the range of about 28 degrees to about 32 degrees relative to each other. More preferably, sidewall sections 204 extend along respective reference planes that are oriented at an angle of about 30 degrees relative to each other. An outer edge portion of each sidewall section 204 has an elongated groove 208 that extends in a direction parallel to the longitudinal axis of housing 200.

The following examples are offered to aid in understanding of the present invention and are not to be construed as limiting the scope thereof. Unless otherwise indicated, all parts and percentages are by weight.

EXAMPLES

Examples 1–6 and 18–21 describe the preparation of a furyl-substituted coumarocryptand (FCCC). Examples 7–11 describe the preparation of a thiophene-substituted coumarocryptand (TCCC).

Examples 12–16 describe the preparation of a sensor that includes a derivative of FCCC. Example 17 describes results of testing performed on that sensor.

Examples 26 to 36 describe various steps in the preparation of 6,7-[2.2.2]-cryptando-3-carboethoxy-coumarin (VII). Example 37 describes hydrolysis of the ester moiety of this compound.

Example 1

Ethyl-(5-bromoethyl)-2-furoate

A. Route 1

The procedure of Tsuboi et al., *Bull. Chem. Soc. Japan*, 60, 1907–12 (1987), was used to oxidize ethyl sorbate by selenium dioxide to give a mixture of ethyl-t-methyl-2-furoate and ethyl-5-methyl-2-selenophenecarboxylate.

A mixture of 18 g ethyl sorbate, 26 g $SeO_2$ and 75 mL xylenes were heated under reflux for about two hours. After filtration, solvent was removed by distillation.

The residual oil was chromatographically separated on silica gel (using 4:1 heptane-ethyl acetate) to the two products. Yield of ethyl-5-methyl-2-furoate was 5.12 g. $H^1$ NMR ($CDCl_3$): d 1.38 (t, 3H, $CH_3$); d 2.40 (s, 3H, $CH_3$); d 4.38 (q, 2H, $CH_2$); d 6.11 (d, 1H, Ar—H); d 7.07 (d, 1H, Ar—H).

Following the procedure described by Vogel in *Textbook of Practical Organic Chemistry*, B. Furniss et al. (editors), 4th ed., Longman, London (1978), p. 402, 14.2 g of the above product was added to 150 mL chloroform with 16.4 g N-bromosuccinimide and 0.5 g peroxide benzoyl. This mixture was refluxed under nitrogen for about two hours, then cooled overnight.

The precipitated succinimide was filtered, and $CHCl_3$ was removed by means of a rotoevaporator. Yield of ethyl-(5- bromoethyl)-2-furoate was 15.5 g. $H^1$ NMR ($CDCl_3$): d 1.38 (t, 3H, $CH_3$); d 4.36 (t, 2H, $CH_2$); d 4.50 (s, 1H, $CH_2Br$); d 6.50 (d, 1H, Ar—H); d 7.12 (d, 1H, Ar—H).

B. Route 2

The procedure of Moore et al., OPPI Briefs, 17, 203 (1985) was used to oxidize 5-methyl-2-furfuraldehyde by sulfamic acid and sodium chlorite.

In 2 L of water were dissolved 50 g 5-methyl-2-furfuraldehyde and 44 g sulfamic acid. In a separate 500 mL of water was dissolved 41 g sodium chlorite and this second solution was added to the first. The combined solution was stirred overnight, extracted three times with 100 mL ethyl acetate, then reduced to give an oil which crystallized upon standing. Yield of 5-methyl-2-furoic acid was 27.5 g. $H^1$ NMR ($CDCl_3$): d 2.35 (s, 3H, $CH_3$); d 6.09 (d, 1H, Ar—H); d 7.08 (d, 1H, Ar—H).

To 500 mL of ethanol were added 22 g of the product from this procedure and a catalytic amount of $H_2SO_4$. After refluxing for two days, the solution was poured into 1L water and extracted with ethyl acetate. Ethyl acetate was removed using a rotoevaporator (i.e., "reduced"). The residue was taken up in 20 mL heptane, which was decanted from a small amount of brown solid that had formed at the bottom of the flask.

The heptane solution was reduced to give 14.6 g of a brown liquid. The yield of this reaction was improved by adding a small amount of 2,6-di-t-butyl-4-methylphenol as an antioxidant. The NMR spectrum was identical to the product obtained from $SeO_2$ oxidation of ethyl sorbate (i.e., ethyl-5-methyl-2-furoate).

Bromination with N-bromosuccinimiide, as described above, yielded ethyl(5-bromomethyl)-2-furoate.

Example 2

Ethyl-(5-cyanomethyl)-2-furoate

A. Route 1

To 20 mL of ethanol was added 15.5 g ethyl-(5-bromoniethyl)-2-furoate (from Example 1), to which was added a solution of 2.7 g NaCN in 10 mL of water. The combination was refluxed for approximately one hour, then cooled and poured into water, and the product was extracted into ethyl acetate.

Reduction of this solution gave 10.8 g of a brown liquid which was about 50% pure. $H^1$ NMR d 1.15 (t, 3H, $CH_3$); d 4.24 (q, 2H, $CH_2$); d 4.30 (s, 2H, $CH_2CN$); d 6.60 (d, 1H, Ar—H); d 7.26 (d, 1H, Ar—H).

B. Route 2

Alternatively, ethyl-(5-cyanomethyl)-2-furoate was prepared from commercially available ethyl (5-chloromethyl)-2-furoate (Aldrich Chemical Co., Milwaukee, Wis.) as follows:

To a 5 L three-necked round bottom flask equipped with mechanical stirrer under nitrogen containing 25.89 g KCN, 500 mL DMSO, and 200 mL THF was added, dropwise, 50 g ethyl-(5-cyanomethyl)-2-furoate in 500 mL THF over a four minute period. The mixture was stirred overnight at 23° C., then stirred with 2 L of 5° C. water and 1 L chloroform for 10 minutes. The aqueous phase was separated and twice extracted 500 mL portions of chloroform. The combined chloroform phases were washed with 1 L saturated aqueous NaCl solution, dried over 270 g sodium sulfate, filtered and evaporated in a rotary evaporator. The residue was flash filtered on a silica gel column, with desired product eluted using a 15:85 mixture of ethyl acetate:petroleum ether. Yield was 13.77 g, and characterization was by NMR as above.

Example 3

6,7-bis-(2'-chloroethoxy)-3-[2"-5"-carboethoxy)-furyl]coumarin

In 100 mL of ethanol were combined 10.83 g of crude ethyl-(5-cyanomethyl)-2-furoate (from Example 2, approximately 50% pure), 16.9 g 4,5-bis(2'-chloroethoxy)-2-hydroxy-benzaldehyde (prepared according to the procedure described in Example 4 of U.S. Pat. No. 5,474,743) and a catalytic amount of piperidine. The mixture was refluxed for approximately one hour, cooled, and treated with 20 mL concentrated HCl. After a few minutes, a precipitate formed. The slurry was cooled and 4.8 g of a solid was collected. $H^1$ NMR ($d_6$ DMSO): d 1.31 (t, 3H, $CH_3$); d 3.98 (m, 4H, $CH_2Cl$); d 4.32 (m, 4H, $CH_2$); d 4.42 (t, 2H, $CH_2$); d 7.22 (d+s, 2H, Ar—H); d 7.40 (d, 1H, Ar—H); d 7.65 (s, 1H, Ar—H); d 8.43 (s, 1H, Ar—H).

Example 4

6,7-bis-(2'-iodoethoxy)-3-[2"-(5"-carboethoxy)-furyl]coumarin

For three days, 4.3 g 6,7-bis-(2'-chloroethoxy)-3-[2"-5"-carboethoxy)furyl]coumarin (from Example 3) and 4.1 g NaI were refluxed in 100 mL methyl ethyl ketone. The solution was cooled and 4.3 g of a precipitate was collected, which was shown to be the corresponding iodinated coumarin. $H^1$ NMR ($d_6$ DMSO): d 1.31 (t, 3H, $CH_3$); d 3.50 (m, 4H, $CH_2I$); d 4.32 (m, 4H, $CH_2$); d 4.40 (t, 2H, $CH_2$); d 7.08 (s, 1H, Ar—H); d 7.18 (d, 1H Ar—H); d 7.34 (d, 1H, Ar—H); d 7.58 (s, 1H, Ar—H) d 8.38 (s, 1H, Ar—H).

Example 5

FCCC-Ester (6,7-[2.2.2]-cryptando-3-[2"-(5"-carboethoxy)furyl]coumarin)

For three days, 4.3 g 6,7-bis-(2'-iodoethoxy)-3-[2"-(5"-carboethoxy)furyl]coumarin (from Example 4), 2.12 g 1,4,10,13-tetraoxa-7,16-diazacyclooctadecane, and 4.3 g $Na_2CO_3$ were refluxed in 400 mL dry acetonitrile. Thereafter, no further increase in the amount of the desired product could be detected by HPLC.

The solution was reduced and the residue was chromatographically separated on neutral deactivated alumina. The diiodo starting material was first eluted with $CH_2Cl_2$. Next, the product was eluted with 5% ethanol in $CH_2Cl_2$. Finally, 5% acetic acid in ethanol was used to remove any FCCC-acid on the column. Alternatively, crude FCCC-ester can be recrystallized by dissolving in hot methanol and adding a 5:1 mixture of cyclohexane and ethyl acetate, from which solid FCCC-ester is obtained. In this procedure, column chromatography is not necessary.

The 5% ethanol fractions were combined and reduced on a rotoevaporator. The yield of FCCC-ester obtained was 3.4 g. $H^1$ NMR ($d_6$ DMSO): d 1.31 (t, 3H, $CH_3$); d 3.5–4.0(m, 24H, cryptand $CH_2$); d 4.32 (q, 2H, $OCH_2$); d 4.50 (t, 2H, CH2); d 4.60 (t, 2H, $CH_2$); d 7.16 (d, 1H, Ar—H); d 7.30 (s, 1H, Ar—H); d 7.42 (d, 1H, Ar—H); d 7.75 (s, 1H, Ar—H); d 8.50 (s, 1H, Ar—H).

Example 6

FCCC-Acid (6,7-[2.2.2]-cryptando-3-[2"-(5"-carboxy)furyl]coumarin)

FCCC-ester (from Example 5) was hydrolyzed by refluxing for about an hour in aqueous 2N HCl. Reaction progress was followed by HPLC. The acid product exhibited a retention time of 10.42 minutes versus 11.85 minutes for the ester starting material. Longer hydrolysis produced a third component (i.e., one other than the ester or acid). The acid was purified by column chromatography on deactivated neutral alumina using ethanol ("EtOH")to elute the unreacted ester, and EtOH/5% acetic acid to elute the acid product. The EtOH(5% acetic acid fractions were combined and reduced using a rotoevaporator, followed by vacuum pump. A pumpkin-colored solid was obtained.

Hydrolysis of the 4.3 g of FCCC-ester was performed in several batches. For example, 0.95 g of ester gave 0.5 g of pure FCCC-acid after chromatography.

Alternatively, ester hydrolysis was carried out according to the following procedure. A mixture of 5.6 g FCCC-ester (from Example 5) in 90 mL THF was stirred and mixed with 29 mL methanol. To this mixture was added a solution of 3.7 g lithium hydroxide monohydrate in 56 mL water. The resultant mixture was stirred at 23° C. for 30 minutes, then diluted with 84 mL 6N HCl, followed by an additional hour of stirring. Solvent was removed at 38° C. using a rotary evaporator for 20 minutes, and the residue was taken up in a solution of 120 mL methanol ("MeOH") and 120 mL THF, then solvent stripping was continued. After several repetitions of the MeOH/THF stripping, most of the residual water had been removed and a yellow solid was obtained. Drying overnight at 0.01 mm Hg gave 9.7 g FCCC-acid.

Example 7

Ethyl-(5-bromomethyl)-2-thiophenecarboxylate

A 25 g sample of 5-methyl-2-thiophenecarboxylic acid was esterified with ethanol as in Example 1B to yield 29.9 g ethyl-5-bromomethyl-2-thiophenecarboxylate. $H^1$ NMR ($CDCl_3$): d 1.35 (t, 3H, $CH_3$); d 2.36 (s, 3H, $CH_3$); d 4.33 (q, 2H, $CH_2$); d 6.02 (d, 1H, Ar—H); d 7.00 (d, 1H, Ar—H).

Bromination of this product with 27.56 g N-bromosuccinimide as in Example 1A gave 36.23 g ethyl-(5-bromomethyl)-2-thiophenecarboxylate as an orange liquid. $H^1$ NMR ($CDCl_3$): d 1.35 (t, 3H, $CH_3$); d 4.30 (t, 2H, $CH_2$); d 4.40 (s, 1H, $CH_2Br$); d 7.19 (d, 1H, Ar—H); d 7.70 (d, 1H, Ar—H).

Example 8

Ethyl-(5-cyanomethyl)-2-thiophenecarboxylate

A 36.23 g portion of ethyl-(5-bromomethyl)-2-thiophenecarboxylate (from Example 7) was reacted with NaCN as described in Example 2 to yield 26 g of ethyl-(5-cyanomethyl)-2-thiophenecarboxylate as a brown liquid. $H^1$ NMR d 1.23 (t, 3H $CH_3$); d 3.93 (s, 1H, $CH_2Br$); d 4.24 (q, 2H,; $CH_2$); d 6.98 (d, 1H, Ar—H); d 7.60 (d, 1H, Ar—H).

Example 9

6,7-bis-(2'-chloroethoxy)-3-[2"-(5"-carboethoxy)-thiophene]coumarin

A solution of 4.8 g ethyl-(5-cyanomethyl)-2-thiophenecarboxylate (from Example 8) in ethanol was treated with 6.5 g 4,5-bis-(2'-chloroethoxy)-2hydroxybenzaldehyde as described in Example 3 to yield 4.8 g of a yellow solid corresponding to the desired coumarin. $H^1$ NMR ($d_6$ DMSO): d 1.29 (t, 3H, $CH_3$); d 3.98 (m, 4H, $CH_2Cl$); d 4.30 (m, 4H, $CH_2$); d 4.40 (t, 2H, $CH_2$); d 7.20 (s, 1H, Ar—H); d 7.39 (s, 1H, Ar—H); d 7.78 (s+d, 2H, Ar—H); d 8.68 (s, 1H, Ar—H).

Example 10

6,7-bis-(2'-iodoethoxy)-3-[2"-(5"-carboethoxy)-thiophene]coumarin

A 2.44 g sample of 6,7-bis-(2'-chloroethoxy)-3-[2"-(5"-carboethoxy)thiophene]coumarin (from Example 9) was reacted with NaI as described in Example 4 to yield 2.0 g of a yellow solid corresponding to the desired iodocoumarin. $H^1$ NMR ($d_6$ DMSO): d 1.31 (t, 3H, $CH_3$); d 3.58 (m, 4H, $CH_2$); d 4.30 (t, 2H, $CH_2$); d 7.23 (s, 1H, Ar—H); d 7.40 (s, 1H, Ar—H); d 7.81 (s+d, 2H, Ar—H); d 8.73 (s, 1H, Ar—H).

Example 11

TCCC-Ester (6,7-[2.2.2]-cryptando-3-[2"-(5"-carboethoxy)thiophenyl]coumarin)

All of the iodocoumarin of Example 10 was heated with 1,4,10,13-tetraoxa-7,16-diazacyclooctadecane as described in Example 5. HPLC of the resulting mixture showed many products, with a sharp peak consistent with the desired product surrounded by a broad peak.

Purification of the crude product with column chromatography on activated alumina (eluted using 7% ethanol in $CH_2Cl_2$) gave one fraction corresponding mainly to the sharp peak. This fraction was reduced to give 0.17 g of the desired TCCC-Ester. $H^1$ NMR ($d_6$ DMSO): d 1.31 (t, 3H, $CH_3$); d 3.5–4.0 (m, 24H, cryptand $CH_2$); d 4.35 (q, 2H, $OCOCH_2$); d 4.39 (t, 2H, $CH_2$); d 4.50 (t, 2H, $CH_2$); d 7.39 (d, 1H, Ar—H); d 7.60 (s83 (d, 1H, Ar—H); d 8.81 (s, 1H, Ar—H).

Example 12

FCCC immobilized on azlactone-functionalized HPPE

A. Amine-functional HPPE membrane

Azlactone-functional hydrophilic porous polyethylene (HPPE) membrane (prepared according to the disclosure of U.S. Pat. No. 5,344,701, incorporated herein by reference) measuring 7.6 cm×7.6 cm was placed in 40 mL $CH_2Cl_2$ containing 6.5 g Jeffamine™ ED900 (bis(2-aminopropyl) polyethylene glycol 800, Fluka Chemical Corp., Ronkonkoma, N.Y.) and 15 drops 1,8-diazabicyclo[5.4.0] undec-7-ene and stirred for about 18 hours. The membrane was removed and washed four times with $CH_2Cl_2$, then air dried.

B. Dye coupling to membrane

About 200 mg of FCCC-acid (from Example 6) was dissolved in about 30 mL dimethylformamide in a widemouthed jar. To this was added 2 mL 1,3-disopropylcarbodiimide (DIC) and about 200 mg hydroxybenzotriazole hydrate (HOBt). The mixture was stirred on a rotary mixer for about 10 minutes. Thereafter, 1 mL N,N-dlisopropylethylamine ()IEA) and four sections of amine-functional membrane from the previous paragraph, each measuring 7.6 cm×7.6 cm, were added.

The above mixture was stirred on a rotary mixer overnight, after which time the membranes were removed and washed four times with dimethylformamide and four times with $CH_2Cl_2$ before being allowed to air dry.

Alternatively, partially hydrolyzed azlactone-functionalized HPPE membrane was added to 50 mL methylene chloride containing 10 mL DIC, 480 mg HOBt, and 1 mL DIEA. The flask was gently agitated on a rotary mixer for about six hours, after which time the membrane was removed and washed extensively with methylene chloride. Regeneration of azlactone functionality was confirmed by the presence of a peak at 1823 cm$^{-1}$ in the infrared spectrum Optionally, an additional acetylation step to remove residual amines can be performed by placing the membranes in 10 mL CH$_2$Cl$_2$ solution containing 10 mL acetic anhydride and 1 mL DIEA. However, no improvement in sensor performance could be detected following acetylation of the product.

Example 13

Immobilized FCCC Coated On HPPP

The method of Examples 17–19 of U.S. Pat. No. 5,474,743 was used to prepare an HPPP membrane on which was coated a polymer coupled to FCCC dye.

Carboxylated PVC ("PVC-COOH", Aldrich) was esterified with Jeffamine ED-900™, and the resulting amine-functional polymer was reacted with FCCC-acid (from Example 6). The dye-coupled PVC-COOH was solution coated onto HPPP.

The dried, coated HPPP web was used to prepare potassium sensors of the invention.

Example 14

FCCC Immobilized On Amine-Functional Cuprophan™ Membrane

A total of 8 sheets of Cuprophan cellulose infiltrated with glycerol (Akzo Nobel Chemicals; Chicago, Ill.), each 30.5 cm×30.5 cm×0.01 mm were washed twice in 500 mL deionized water (10 minutes) to remove the glycerol. Each sheet was stretched on a 23.5 cm×26 cm glass plate and dried at room temperature (approximately 21° C.).

A. Overcoat

An overcoat solution was prepared by adding 4.5 g dextran (MW 2,000,000) and 225 mL deionized water to a wide-mouth 500 mL bottle. The mixture was heated to 50° C. in an oven to dissolve the dextran. Then, 2.25 g Marasperse DBOS-4™ dispersing agent (Diashowa Chemicals, Inc.; Rothschild, Wis.) was added and the mixture was shaken. Thereafter, 4.5 g Monarch-700™ carbon black (Cabot Corp.; Waltham, Mass.) was added with swirling. The solution was sonicated 5 times (with a cycle time of 3 minutes) by means of a Model W-385 sonicator (Misonix Inc.; Farmingdale, N.Y.) in an ice water bath, with shaking between each cycle. A uniform aqueous dispersion of carbon-black was obtained. To the dispersion was added 4.5 g 50% (aq.) NaOH solution, and the dispersion was shaken for another minute. Subsequently, 6.75 g of a 50% ethylene glycol diglycidylether (EGDGE) solution in deionized water was added, followed by shaking for one minute. After aging for 10 minutes at room temperature without shaking, the resulting overcoat solution was sprayed evenly onto each sheet of Cuprophan™ membrane. A Model 8452A UV spectrophotometer (Hewlett-Packard Instruments Corp.; Palo Alto, Calif.) was used to monitor opacity of the sheets (approximately 3 absorbance units) at 464 nm. The sheets were dried for an hour on glass plates.

B. Crosslinking

In a 1 L beaker, a solution of 3.1 g of 50% NaOH solution in 354 mL deionized water was prepared. To this was added 86 g DMSO with mixing. Subsequently, 443 g of a 50% aqueous EGDGE solution was added and mixed.

Frames were placed on all eight plates and clamped so that the crosslinking solution could be poured on the sheets and retained. The solution was poured onto each plate (about 100 mL) to crosslink for 50–60 minutes. The plate was gently swirled three times in this period to ensure that fresh solution came in contact with the Cuprophan™ sheet. Thereafter, the Cuprophan™ membranes were cut along the frame and rinsed three times with 2000 mL deionized water.

C. HDA (1,6-Hexandediamine) reaction

Crosslinked Cuprophan™ membranes were immersed in a solution of 120 g 70% HDA in 2.0 L deionized water in a 4L beaker at room temperature for 105 minutes. Care was taken to remove trapped air bubbles by swirling the sheets with a glass rod. The sheets were removed from the beaker and rinsed five times with 2000 mL deionized water to wash off excess HDA, then soaked in deionized water. (At this stage, the sheets can be immediately used in the next step. Alternatively, the sheets can be stored overnight in deionized water/acid bath (1 mL 12 N HCl in 2 L deionized water).)

D. FCCC Coupling Reaction

A dye solution was prepared by dissolving 30 mg FCCC (from Example 6) in a 15.2 cm diameter petri dish containing 30 mL DMF with stirring for 10–15 minutes. Subsequently, 0.8 mL DIC and 190 mg HOBt were added and stirred for 15 minutes, after which 0.4 mL DIEA was added and stirring was continued for about five minutes. HDA-functionalized Cuprophan™ sheets were removed from the deionized water and cut into 10.2 cm×10.2 cm pieces and placed on a paper towel to blot off excess water. Two such pieces, one at a time, were immersed (while being kept flat) in the dye bath for 24 hours, after which the pieces were removed and washed twice with 250 ml portions of DMF and twice with 500 mL dilute aqueous HCL (pH 2–3.5) for about three minutes for each washing.

Alternatively, HDA-functionalized membrane was washed in 2.5% Na$_2$CO$_3$ for 30 minutes, followed by three rinsings in water and three more in acetone. In 35 mL acetone was dissolved 100 mg FCCC (from Example 6), followed by addition of 1 mL DIC, 50 mg HOBt, and 1 mL DIEA. This solution was mixed on a rotary mixer for 15 minutes, at which time the washed membranes were added. After three days, the membranes were removed and washed once with acetone and three times with water. The washed membranes were then added to 20 mL of an acetone solution containing 10 mL acetic anhydride and 1 mL DIEA and rotary-mixed for 20 minutes. The membranes were removed from this solution and washed once with acetone and three times with water.

Intensities can be measured on this bulk material in pH 7.34 N-(2-hydroxyethyl)piperazine-N'-ethanesulfonic acid (HEPES) buffer (Sigma Chemical Corp.; St. Louis, Mo.) at 8 mM K$^+$ on a S400 monitor (CDI/3M Health Care) modified with a 16-bit A/D converter and LabVIEW™ software (National Instruments; Austin, Tex.). Excellent intensity of 1.3×10$^5$ to 1.5×10$^5$ counts were obtained based on a standard gain configuration.

Example 15

Sensor-Cassette Assembly

A dye-coupled Cuprophan™ sheet (from Example 14) was laminated to a thin (0.175 mm) polycarbonate sheet (Bayer AG; Leverkusen, Germany) using a 2-part polyurethane adhesive such as Flexobond™ 430 (Bacon Industries, Inc.; Irvine, Calif.). On the polycarbonate side, a CW14™ pressure sensitive adhesive sheet (RSW Inc., Specialty Tape Div.; Racine, Wis.) was attached and the release-liner was removed. Discs were punched from the laminate using a hole-puncher and were placed on the pH and $AO_2$ channels of an S400 cassette (CDI/3M Health Care; Tustin, Calif.). These two channels were used with the appropriate optics as potassium detection channels on modified S400 monitors.

Example 16a

LED Testbed

Figure 10:
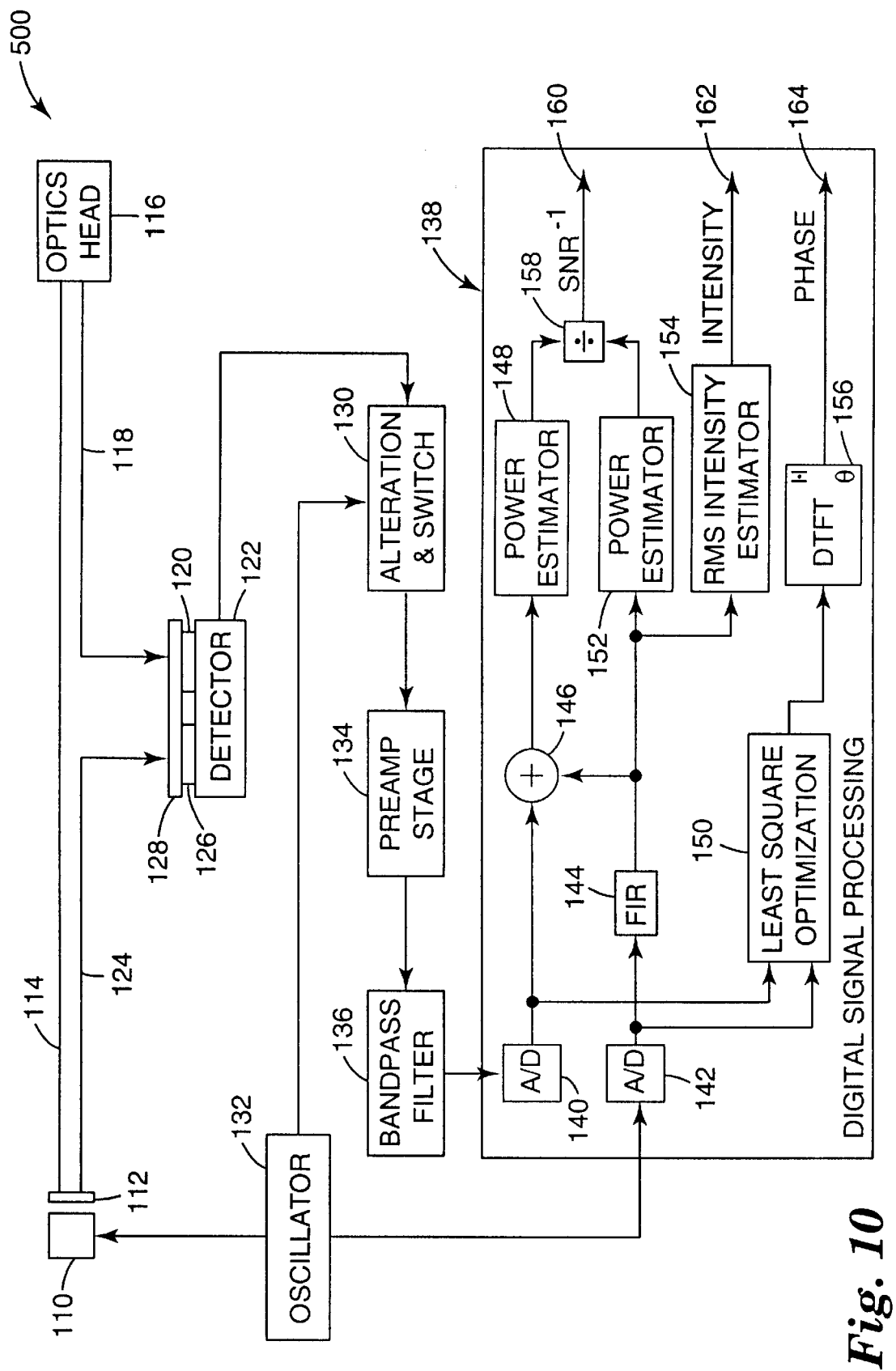
FIG. 10 shows a schematic diagram of a 30 KHz phase-modulation breadboard used to evaluate potassium response of model compounds and coumarocryptand ionophores of the invention.

FIG. 10 shows the schematic diagram 100 for an LED-based phase-modulation breadboard used to test the red-shifted $K^+$ sensor of the invention. This breadboard was designed to evaluate both amplitude and phase-modulation approaches to blood gas detection.

For the potassium sensor tests, GaN LEDs 110 from Nichia Chemical Industries, Tokushima, Japan, or Toyoda Gosei Co., Ltd (under the brand name Ledtronics™) were amplitude modulated at a 30 kHz carrier frequency, a burst duration of 0.2 seconds, a repetition rate of 5 sec, and an average output power of 2.5 mW. The light was focused, passed through a bandpass excitation filter 112 (390 nm±25 nm; %T=52%; out-of-band blocking =0.001%T; available from SpectroFilm; Woburn, Mass.), and refocused into a fiber optic cable 114. At the distal end of the cable was a CDI S400 optical head 116. A randomized fiber bundle 118 returned the modulated fluorescent return to a bandpass emission filter 120 (475±35 nm; %T=64%; out-of-band blocking =0.001%T) such as is available from SpectroFilm. The filtered optical signal was then focused onto the active region of an OPTO-8™ photomultiplier tube detector 122 or a S1337-33-BR™ photodiode detector (both available from Hamamatsu Corp.; Bridgewater, N.J.). A small fraction of the excitation fibers 124 were directly routed to the detector assembly and attenuated with a neutral density filter 126 to provide a reference optical signal from the LED.

Using a computer-controlled optical shutter 128, the photodetector alternately sampled the excitation signal and the fluorescent return signal. This provided optical referencing to correct for fluctuations in the LED output amplitude. In addition, an electronic switch 130 was used to alternately sample the detector photo current and a 30 kHz electrical reference signal from the frequency generator 132. The detector output was directed to a three-stage electronic circuit which converted the photocurrent from the photodiode detector to a voltage. The attenuation and switch stage 130 was used to attenuate a reference electrical signal from the LED drive oscillator 132 and switch between this attenuated reference signal and an unattenuated photosignal. The transimpedance preamplification stage 134 converted a photocurrent or the reference electrical signal to a voltage using an OPA627 operational amplifier circuit. The following stage 136 was a two-stage Delyiannis-style bandpass filter using two OPA627 operational amplifiers. This stage bandlimits the noise power while further amplifying the signal. The gain of the three-stage circuitry was $7.3 \times 10^8$ V/A (177 dB) and was bandlimited to 400 Hz with approximately 30 kHz center frequency.

The amplified photosignal or reference electrical signal were digitally sampled at 100 kHz and processed 138 using LabVIEW™ virtual instrument software using a least squares estimation of the phase, intensity, and signal-to-noise ratio (SNR). Under these sampling conditions the noise power was further band limited to less than 1 Hz, further increasing the SNR.

In operation, LabVIEW™ software alternately sampled the optical sensor signal, the optical referencing signal, and the electronic reference signal. The optical reference signal corrected for LED fluctuations, and the electronic referencing signal corrected for electronic drift associated with temperature, humidity, and radio frequency (RF) rectification.

Example 16b

Spectral Studies of FCCC and FCCC-based Sensors

Figure 1B:
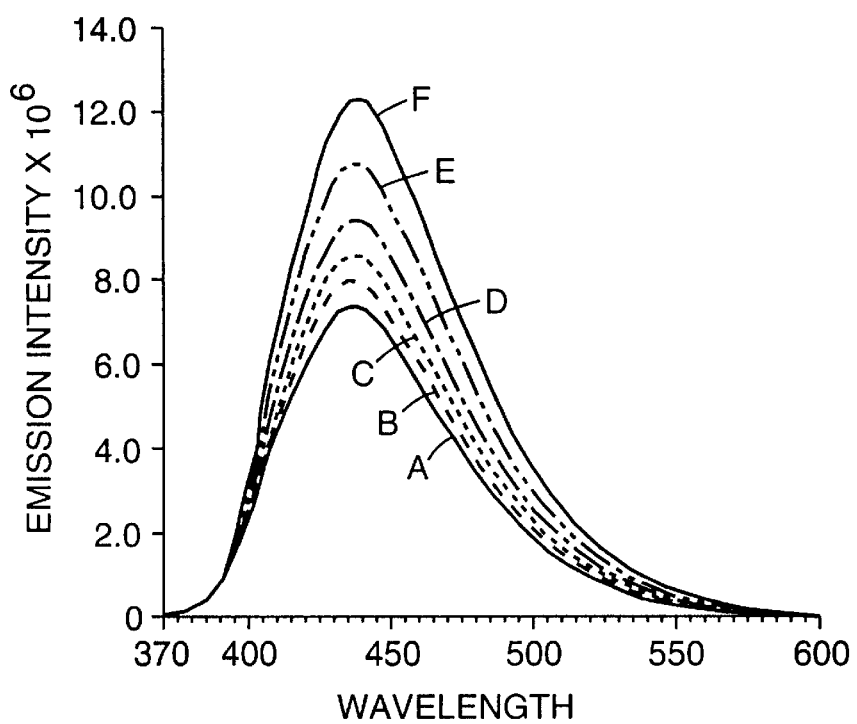
Figure 1C:
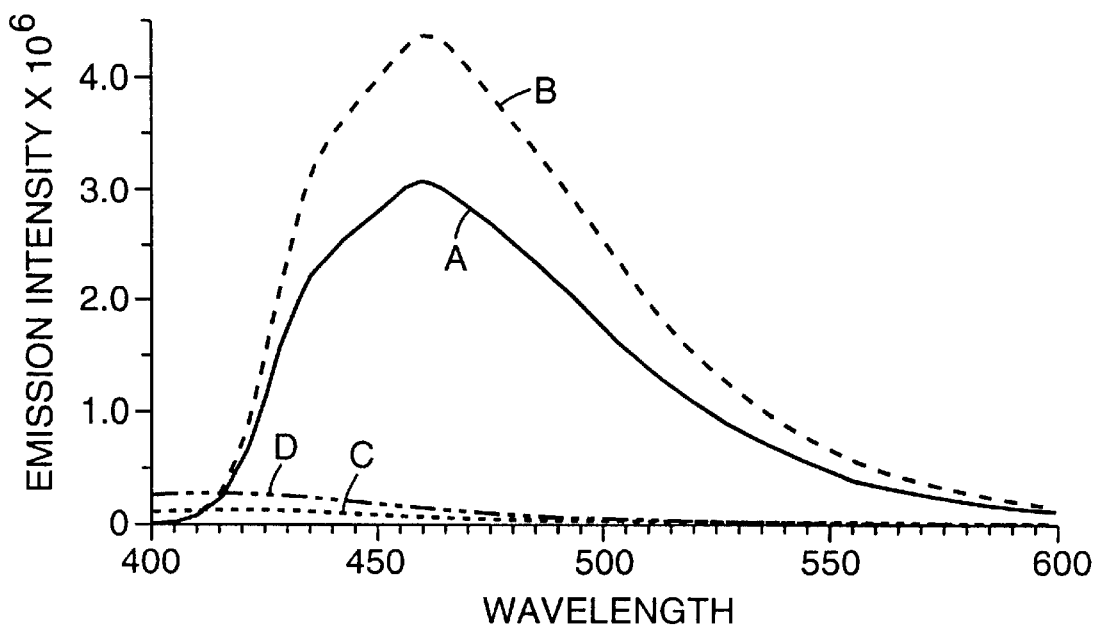

FIGS. 1a and 1b compare the potassium response of FCCC (Example 6) and 6,7-[2.2.2]-cryptandocoumarin-3-carboxylic acid ("CCC", U.S. Pat. No. 5,474,743, Example 11) in solution. Equimolar solutions (0.08 AUFS) were prepared in 100 mM HEPES buffer at pH 7.3. Emission spectra were measured at 392 nm and 354 nm, respectively, in FIGS. 1a and 1b, respectively, at potassium concentrations of 0.0, 1.0, 2.0, 3.9, 7.7, and 15 mM, labeled A, B, C, D, E, and F, respectively, in both FIGS. 1a and 1b. FIG. 1c compares the response of FCCC at 0 (A) and 15 (B) mM potassium ion concentration to that of CCC at 0 (C) and 15 (D) mM potassium ion concentration, using excitation at 392 nm. FIGS. 1a–1c show a significant improvement in response to a wide range of potassium ion concentrations for an ionophore of the present invention (FCCC) vs. a previously-prepared ionophore (CCC), and that response to excitation at a preferred wavelength (392 nm) is greatly enhanced.

When FCCC and CCC were excited at their respective absorption maxima (392 vs 354 nm), FCCC exhibited a slightly diminished potassium response (29% vs. 48% for CCC for an 8 mM $K^+$ challenge), consistent with the red-shifted emission maximum (460 nm vs 440 nm). "Potassium response," expressed in percent, refers to the percentage increase of emission intensity for a given potassium ion concentration over emission intensity in the absence of potassium ion. Importantly, FIG. 1c shows that when both samples were excited at 392 nm to mimic the filtered output of a GaN blue LED or flash lamp, the FCCC fluorescent return was 14 times that for CCC (i.e., curve "B" vs. curve "D"). The red shifting and increased efficiency for FCCC substantially improved the performance of a lamp-based potassium sensing system. It also provided enough additional signal so that FCCC was able support potassium sensing with a pulsed GaN blue LED and a photodiode detector, whereas CCC was not. Importantly, the fluorescence lifetimes of FCCC and CCC were found to be function of potassium concentration, which may allow for phase-modulation based $K^+$ sensing.

Figure 2:
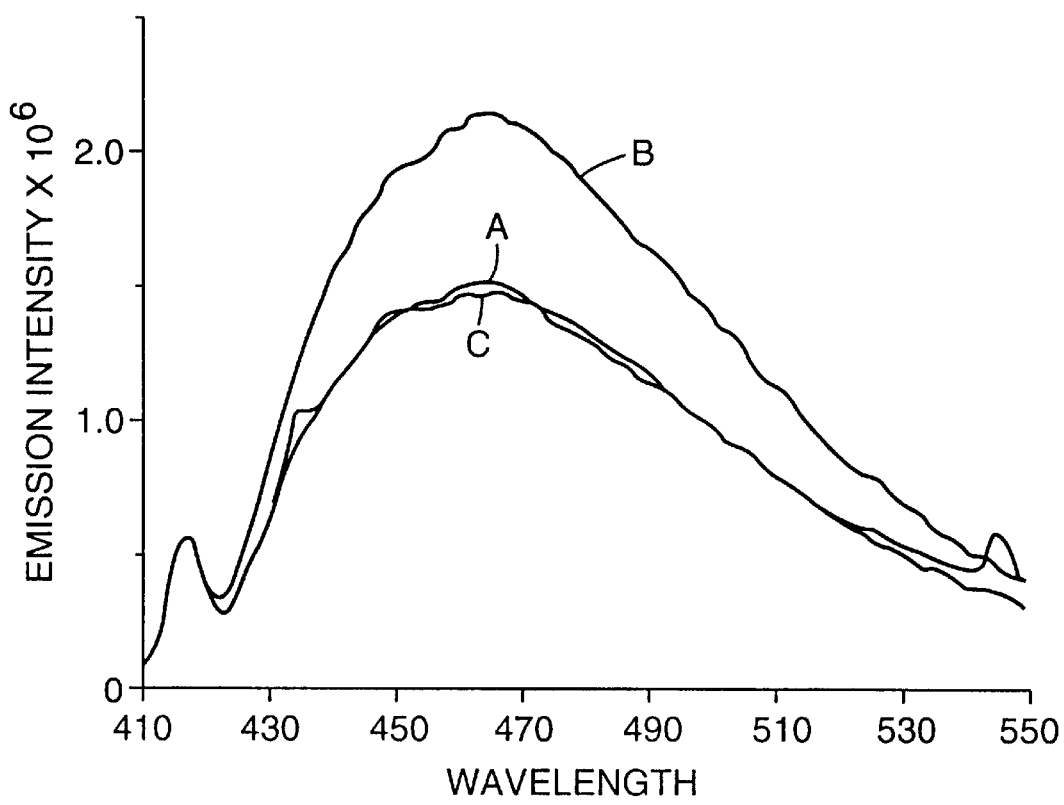
FIG. 2 shows a graphical representation of the fluorescence emission response of a coumarocryptand ionophore of the invention subjected to successive challenge of 0, 8, and 0 mM $K^+$ concentrations, respectively.

FIG. 2 shows the potassium response of FCCC indicator on HDA functional Cuprophan (Example 14d). In FIG. 2, curve A represents initial 0 mM $K^+$ concentration, curve B represents emission intentsity at 390 nm excitation for 8 mM potassium ion concentration after 2 minutes exposure, and curve C represents response to 0 mM potassium ion concentration immediately after exposure for curve B. The FCCC-HDA-Cuprophan sensor showed a large (31%), rapid (<2 min.), and reversible response to potassium ions. The potassium response observed in solution is fully retained upon immobilization. The choice of polymer support is very important. FCCC-ED900-PVC sensors (Example 13) show very little potassium response (6%). FCCC-azlactone-HPPE-based sensors (Example 12) exhibit a rapid (<1 minute), reversible response but a diminished potassium response (15%) relative to solution (29%).

Figure 3:
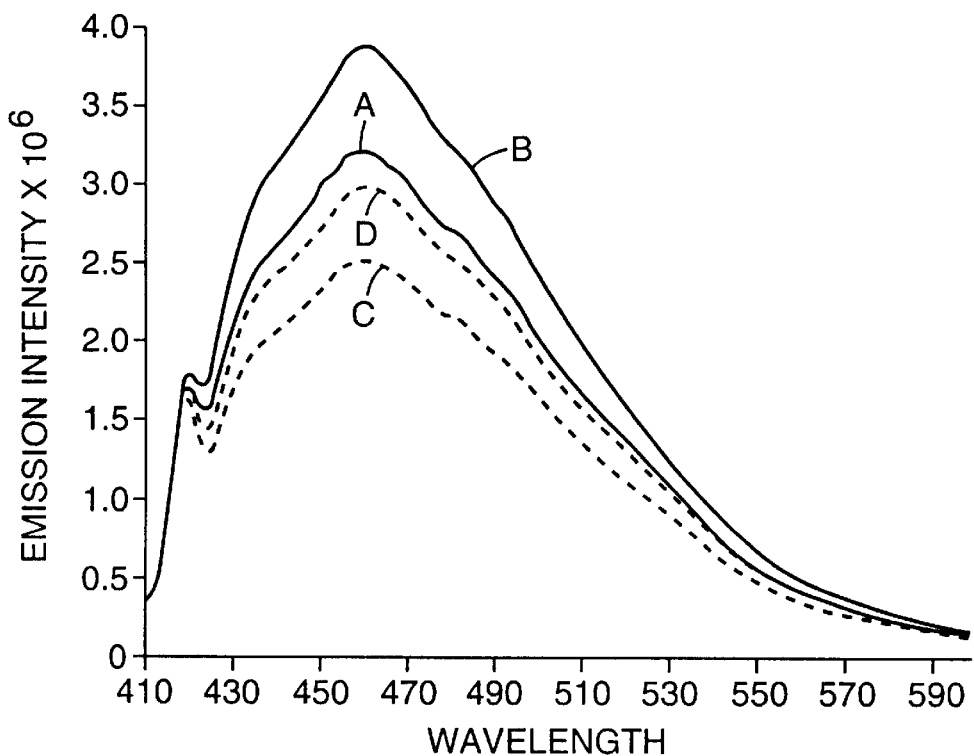
FIG. 3 shows a graphical representation of the effect of irradiation on potassium sensors of the invention.

Photodegradation of FCCC-based sensors is slow and monatomic, as shown in FIG. 3 for FCCC-azlactone/HPPE sensors (Example 12). Response at 390 mm excitation light is shown before irradiation at 0 mM (curve A) and 16 mM (curve B) potassium ion concentration. The sensor membrane was immersed in HEPES buffer and continuously irradiated at 390 nm in a SPEX Fluorolog™ Series spectrofluorimeter (SPEX Industries, Inc., Edison, N.J.) using 1 mm excitation slit widths for one hour. Response at 390 mm excitation light is shown after irradiation, also at 0 mM (curve C) and 16 mM (curve D) potassium ion concentration. The degradation rate has been observed to be predictable on repeated measurement.

FCCC sensors retain their potassium response and spectral characteristics after autoclave sterilization for 2 hours at 120° C. in pH 7.4 HEPES buffer.

Figure 4B:
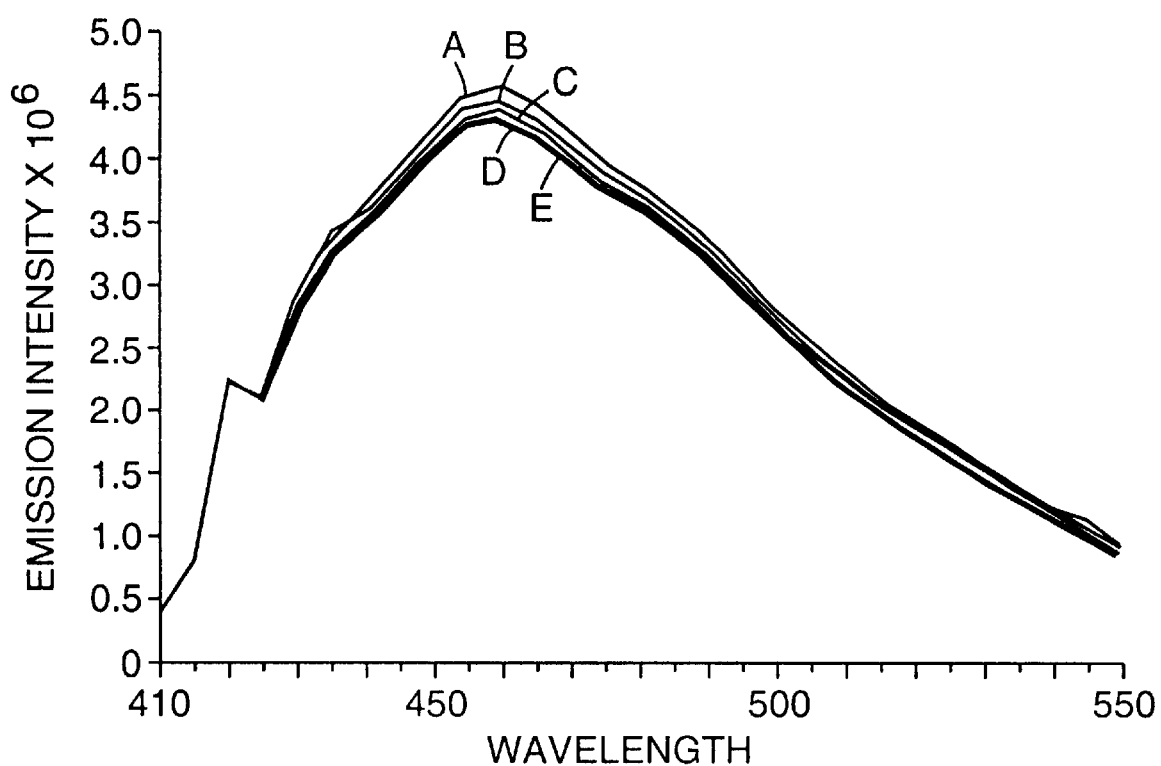

FIGS. 4a and 4b compare the pH-dependent response of CCC- (FIG. 4a) and FCCC- (FIG. 4b) azlactone/HPPE sensors, both prepared according to the method described in Example 12, above. The sensors were mounted on an S400 flowthrough cassette (CDI/3M Health Care) using Type 924 transfer tape adhesive (3M Company) and were hydrated overnight. A solution of HEPES buffer (100 mM, 0 mM potassium) was titrated to pH 3.76 using HCL (1M) and circulated over the sensors using a peristaltic pump. The solution was then titrated to each successive pH using NaOH (1M) and irradiated at 370 nm (CCC sensor) or 390 nm (FCCC sensor). In both FIG. 4a and 4b, curves representing pH are labeled as follows: A=pH 6.98; B=pH 7.18; C=pH 7.4; D=pH 7.62, and E=pH 7.83. An emission spectrum was recorded after equilibration at each pH (3 minutes). Both sensors exhibit a pKa=5.8. However, the pH dependence of the emission intensity, that is, the change in intensity from lowest to hightest pH, is much smaller for the FCCC sensor (6%) vs the CCC sensor (33%) over the physiological pH range of approximately 7.0–7.8.

Figure 5:
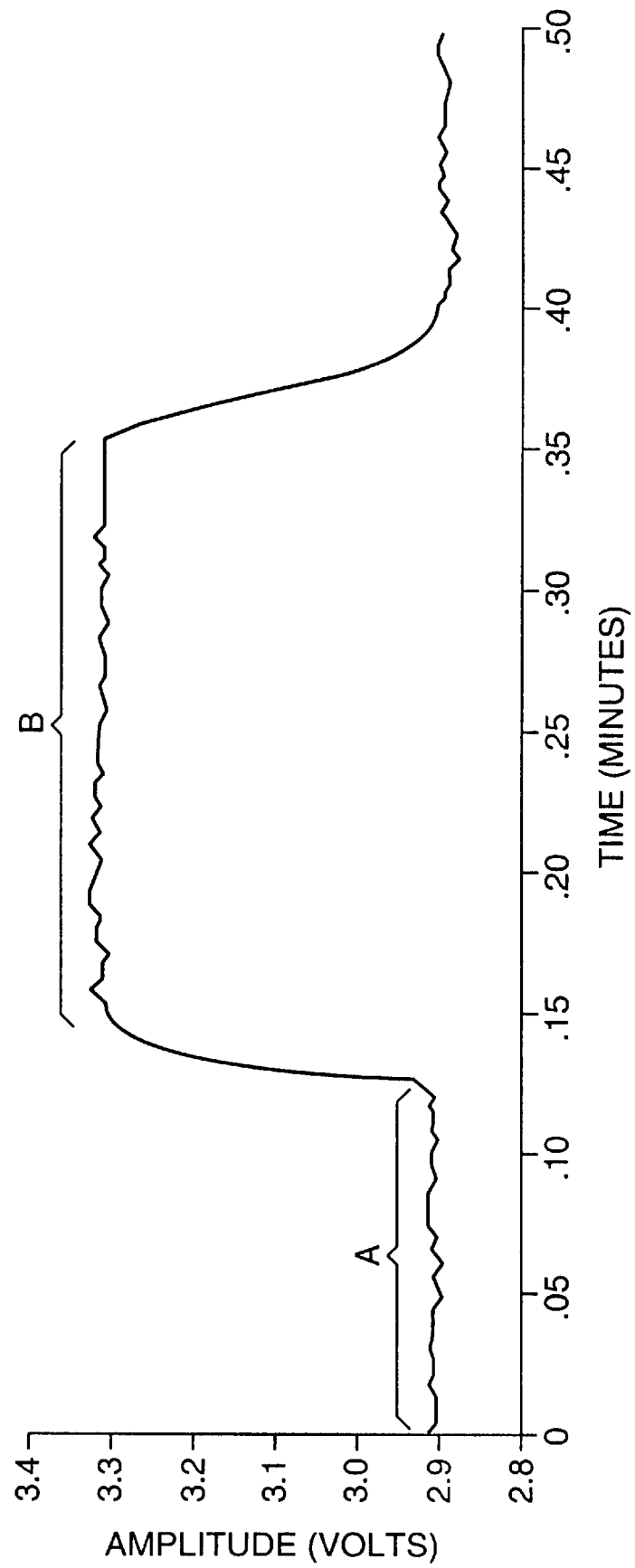
FIG. 5 shows a graphical representation of the response of a potassium-sensing device of the invention cycled between 0 and 16 mM $K^+$ in HEPES buffer.

FIG. 5 shows data from FCCC-azlactone/HPPE membranes incorporated into an S400 flow-through cassette and measured on a phase modulation LED breadboard, as shown schematically in FIG. 10. The cassette was hydrated overnight, after which the sensor was cycled between 0 and 16 mM $K^+$ in HEPES buffer (100 mM, pH 7.4). The sensor was exposed to 0.2 sec bursts of 30 kHz amplitude modulated light from an optically filtered (390 nm) LED (Nichia Chemical Industries). The portion of the response curve at "A" corresponds to 0 mM potassium ion concentration, while at "B," potassium ion concentration was 16 mM. The difference in amplitude, approximately 400 mV, and the rapid change in output voltage (approximately 0.025 sec) showed that useful potassium ion detection could be obtained with ionophores of the invention used in commercially-available sensors modified to take advantage of shorter wavelength light sources.

Light level measurements indicated greater than 20 nW of fluorescent return harvested at the detector. 20 nW was a sufficient optical return to support high signal-to-noise ratios when combined with pulse integration methods. Using an OPA-627 op-amp with a 10 kHz bandwidth (10 Mohm feedback and 1.4 pF capacitor) and a gain of 5 $\mu$W, the 20 nW fluorescent return provided a 100 mV electrical signal, at a noise floor of 100 $\mu$V per pulse. This gave a noise floor of 0.1% per pulse. Further improvements were made by averaging multiple pulses. This approach was used in the design of a compact glass fiber GaN LED optics module. Solid state light sources and detectors were mounted in a compact module. An on-board A/D converter provided a digitized output signal which could be directed to any host monitor. The module mated directly with the flow-through sensor cassette, e.g., FIG. 11.

Example 16c

Studies of Red-shifting Substituents

More than 80 coumarocryptand derivatives were modeled to support the conclusion that the compounds represented by Formula A will support red-shifted $K^+$ sensing.

We find no evidence for $K^+$ dependent spectral shifts which would be expected if a $K^+$ dependent charge transfer mechanism were operative. Instead, we find evidence for a potassium dependent vibronic coupling mechanism.

Experimental data for various EDO-, MDO- and DMO-type coumarin-derivatives are shown in Table 16d. Fluorescence lifetime data for dimethoxy (DMO), methylenedioxy (MDO), and ethylenedioxy (EDO) coumarin model compounds were obtained in deoxygenated methyl alcohol using a Photochemical Research Associates (PRA) System 3000 fluorescence lifetime instrument. Fluorescent decays were measured using time-correlated single photon counting techniques referenced to a standard scatter solution and analyzed by global minimization.

TABLE 16d

Fluorescence Lifetime Studies

| | | Experimental | | Derived | | |
|---|---|---|---|---|---|---|
| Cmpd | | $\Phi$ | $\tau$ nsec | $k_f \times 10^8$ sec$^{-1}$ | $k_{nr} \times 10^8$ sec$^{-1}$ | $k_f/k_{nr}$ |
| 1 | MDO | 0.25 | 2.00 | 1.26 | 3.74 | 0.34 |
| 1 | DMO | 0.27 | 2.11 | 1.28 | 3.46 | 0.37 |
| 1 | EDO | 0.05 | 0.51 | 1.06 | 18.6 | 0.06 |
| 2 | MDO | 0.55 | 6.46 | 0.85 | 0.70 | 1.20 |
| 2 | DMO | 0.50 | 6.89 | 0.72 | 0.73 | 0.99 |
| 2 | EDO | 0.28 | 4.22 | 0.66 | 1.72 | 0.38 |
| 3 | MDO | 0.84 | 5.82 | 1.44 | 0.28 | 5.10 |
| 3 | DMO | 0.79 | 6.24 | 1.26 | 0.34 | 3.73 |
| 3 | EDO | 0.24 | 2.27 | 1.05 | 3.36 | 0.31 |
| 4C | MDO | 0.10 | 2.06 | 0.51 | 4.35 | 0.12 |
| 4C | DMO | 0.06 | 1.33 | 0.46 | 7.06 | 0.07 |
| 4C | EDO | 0.05 | 1.28 | 0.38 | 7.44 | 0.05 |

In the table: $\phi$ is the quantum yield; $\tau$ is the relaxation time; $k_f$ is the rate constant for fluorescence decay; and $k_{nr}$ is the rate constant for non-radiative decay. The rate constants are derived by solving equations (4) and (5):

$$\tau = 1/(k_f + k_{nr}) \qquad (4)$$

$$\phi = k_f/(k_f + k_{nr}) \qquad (5)$$

The fluorescence quantum yield of 6,7-ethylenedioxy (EDO) coumarin model compounds is always smaller than that of corresponding 6,7-methylenedioxy (MDO) or 6,7-dimethoxy (DMO) derivatives. Importantly, the EDO-type compounds can support an out-of-plane puckering vibration, while this vibration is suppressed in the MDO-type and DMO-type coumarins. Fluorescence lifetime studies, reported in Table 16d, show that such out-of-plane puckering in compounds 1, 2, and 3 leads to an increase in the non-radiative rate constant, $k_{nr}$ and does not substantially change the radiative, or fluorescence, rate constant, $k_f$. This puckering may contribute to mixing of close-lying $n\pi^*$ and $\pi\pi^*$ states. Comparative compound 4C, with an emission maximum of 535 nm, exhibits a large $k_{nr}$ for all analogs, presumably because of direct mixing of the $\pi\pi^*$ states with the ground state.

Figure 6A:
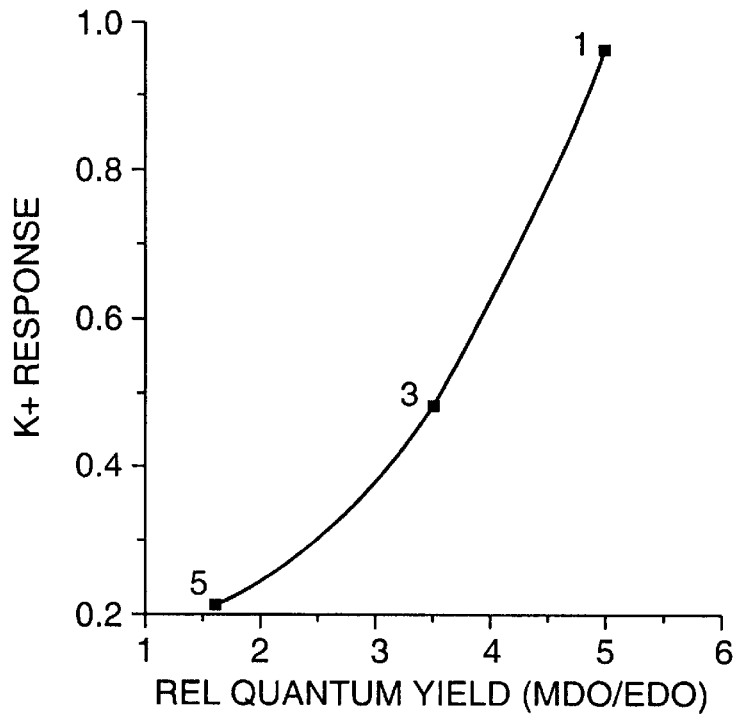
FIGS. 6a and 6b shows a graphical representation of a correlation between $K^+$ response of certain substituted coumarocryptands and the relative quantum yield of similarly substituted model compounds MDO and EDO (FIG. 6a) and model compounds DMO and EDO (FIG. 6b)
Figure 6B:
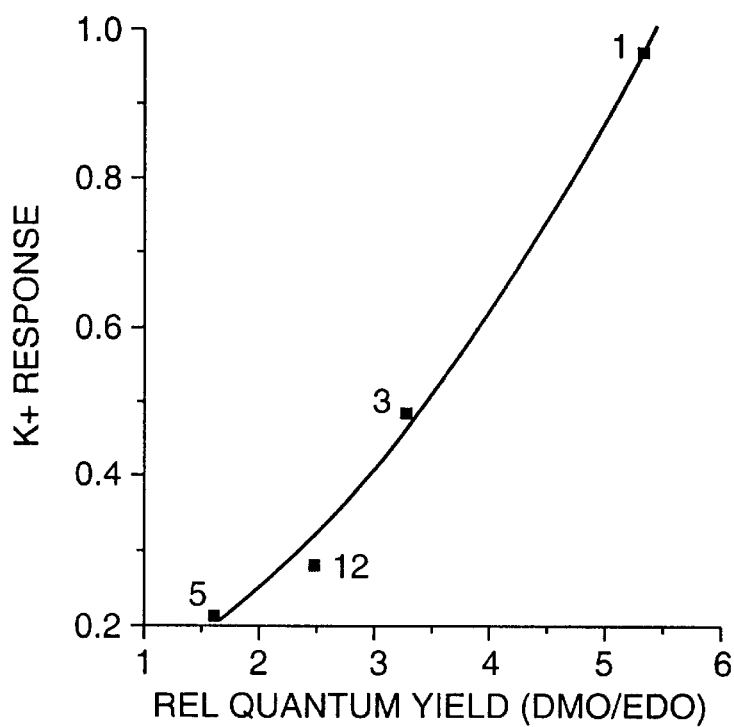

Data shown in Table 16e confirm the observation that both DMO- and MDO-type model compounds can be useful to predict the response of coumarocryptands of the invention to potassium ion (e.g., suppression of out-of-plane puckering). In particular, there is a strong correlation between the potassium response of several coumarocryptand derivatives and the MDO/EDO quantum yield ratio for corresponding model compounds, as shown in FIGS. 6a and 6b. "K+ response" means the percentage increase of emission intensity for a given potassium ion concentration (8 mM) over emission intensity in the absence of potassium ion. In FIGS. 6a and 6b, data points labeled "1", "3", "5", and "12" correspond to the ratio of the measured quantum yields of MDO- (FIG. 6a) and DMO-type (FIG. 6b) compounds 1, 3, 5, and 12, to the measured quantum yields of the corresponding EDO-type compounds, respectively, of Table 16c, plotted against the response of similarly-substituted coumarocryptands in the presence and absence of 8 mM potassium ion concentration.

This suggests that K+ binding to the cryptand oxygens suppresses the out-of-plane puckering vibration responsible for non-radiative decay in the same way that MDO- and DMO-type compounds suppress this puckering vibration. Importantly, the rates of radiative ($k_f$) and non-radiative ($k_{nr}$) relaxation must be competitive to have a working potassium sensor. If the chromophore is too rigid, $k_{nr}$ will be too small, and the quantum yield, $\phi$, will remain high. If $k_{nr}$ is too large, K+ dependent modulation will be washed out and the fluorescence quantum yield will remain low. Experimental and theoretical studies indicate that red-shifted coumarocryptands derivatives of the present invention make good candidates for potassium sensing. Data presented in Table 16d show that both amplitude and lifetime measurements can be used for quantitative measurement of, e.g., potassium ion.

TABLE 16e

| # | Structure | $\Phi_{MDO}/\Phi_{EDO}$ | $\Phi_{DMO}/\Phi_{EDO}$ | $\lambda_{em}$, nm | K+ response* |
|---|---|---|---|---|---|
| 1 | [structure with CH3] | 5.0 | 5.40 | 420 | 0.95 |
| 2 | [structure with CF3] | 1.96 | 1.79 | 470 | — |
| 3 | [structure with OCH2CH3 ester] | 3.50 | 3.30 | 438 | 0.48 |
| 4 | [structure with OCH2CH3 ester] | 2.0 | 1.25 | 535 | — |
| 5 | [structure with benzimidazole] | 1.60 | 1.60 | 479 | 0.21 |
| 12 | [structure with benzoyl] | — | 2.5 | 470 | 0.28 |

*K+ response was measured for the corresponding cryptand derivative, at 0 and 8 nM K+ conc.

Without wishing to be bound by theory, a proposed mechanism of non-radiative relaxation of coumarins can be employed. In the proposed mechanism, the coumarin is initially photoexcited from the $S_0$ ground state into an $S_1(\pi\pi^*)$ excited state. The change in the $\pi$ electron density causes the position of all the nuclei to change from the ground state nuclear configuration to a less energetic excited state nuclear configuration. For planar aromatic compounds such as the coumarins, the $S_1(\pi\pi^*)$ state relaxes through a molecular distortion that is mainly confined to the plane of the aromatic ring system.

Once the $S_1(\pi\pi^*)$ excited state has relaxed, it becomes nearly isoenergetic with the orthogonal $S_2(n\pi^*)$ excited state. Out-of-plane vibrations will mix these two states, modifying their potential energy surfaces and, under the right circumstances, enhancing the radiationless transition from the $S_1(\pi\pi^*)$ state to the ground $S_0$ state.

Figure 7C:
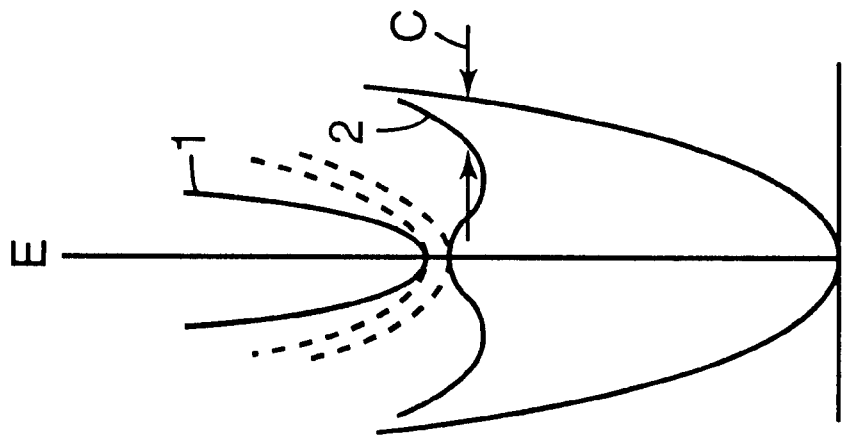
FIG. 7 illustrates potential energy diagrams showing the effect of weak, strong, and very strong vibronic coupling on barrier width for radiationless transition in molecules.
Figure 7B:
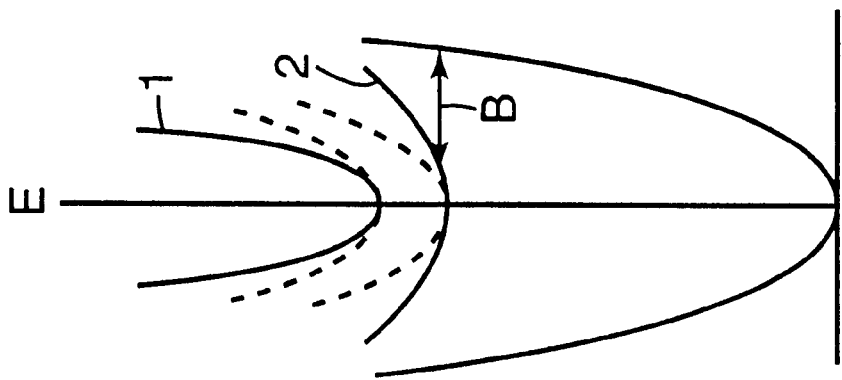
Figure 7A:
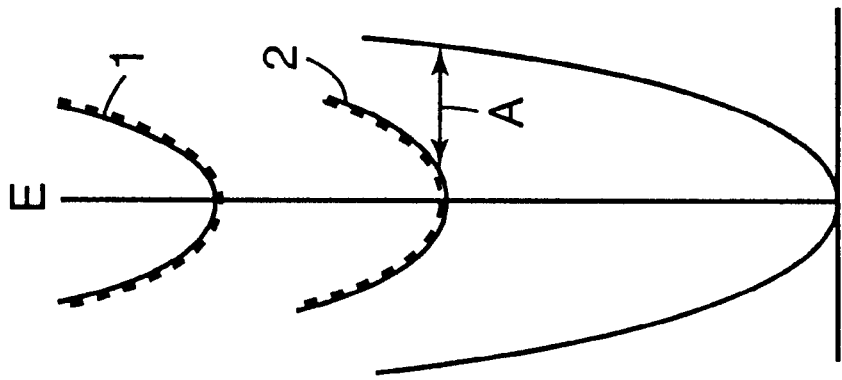

The orbital energetics for such an excited state process are shown in FIG. 7. In FIG. 7, scheme 7A represents weak coupling, scheme 7B represents strong coupling, and scheme 7C represents very strong coupling, where "coupling" refers to non-totally-symmetric vibronic coupling of $S_1(\pi\pi^*)$ (curve 2) and $S_2(n\pi^*)$ (curve 1) states. Unmixed states are shown with dashed lines and vibronically coupled states are shown with solid lines. The barrier width for radiationless transitions are indicated by arrows A, B, and C, respectively. Clearly, when the $S_2(n\pi^*)$ orbital is substantially higher in energy or is absent, vibronic coupling is not favored (scheme A). In this case, the fluorescence quantum yield remains high and potassium response is not observed. If $S_2(n\pi^*)$ and $S_1(\pi\pi^*)$ are very strongly coupled (scheme C), radiationless decay dominates. In this case, fluorescence quantum yield is very low and independent of $K^+$ binding. In between these two extremes vibronic coupling is modest and the non-radiative decay rate becomes $K^+$ sensitive (scheme B).

Finally, as the energy gap between the initial $S_1(\pi\pi^*)$ and final $S_0$ states of the radiationless transition decreases, the energy accepting ability of the out-of-plane puckering mode diminishes. Also, in-plane modes more effectively couple the $S_1(\pi\pi^*)$ and $S_0$ states directly, without the need for a nearby $S_2(n\pi^*)$ state. Thus, the $K^+$ response will become less pronounced as the $S_1(n\pi^*)$-$S_0$ electronic energy gap decreases; i.e., as the fluorescence wavelength increases.

Figure 8:
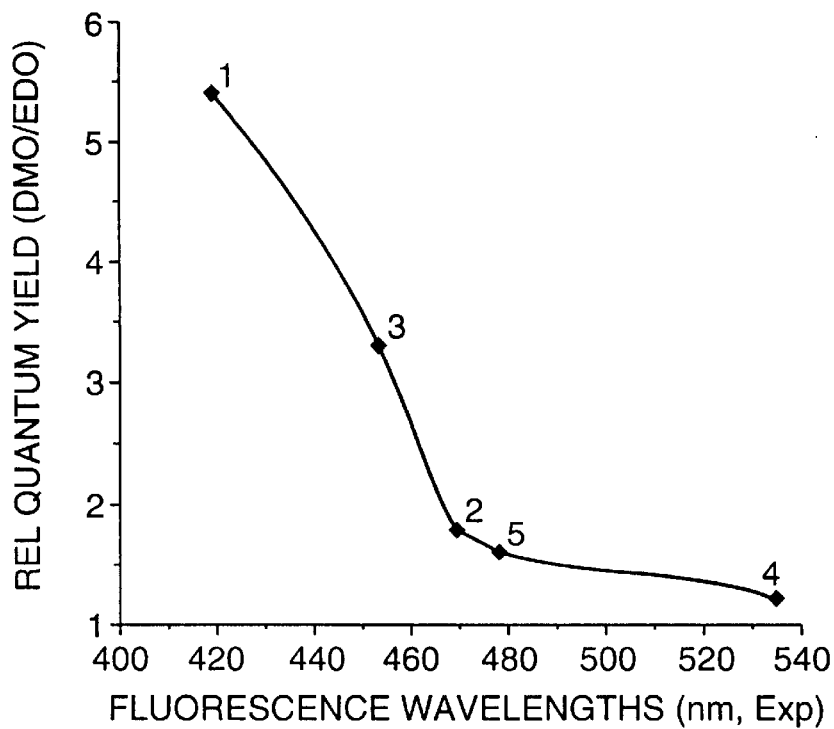
FIG. 8 shows a graphical representation of the correlation between experimental fluorescence emission maxima and emission ratios for substituted model compounds DMO and EDO.

This is shown experimentally for coumarocryptands of the invention in FIG. 8, the data-point numbers corresponding to the coumarin substitution patterns indicated in Table 16c. Data point "1" corresponds to the experimentally-obtained relative quantum yield $\phi$ for a DMO-type coumarin compound and an EDO-type coumarin compound, plotted against experimentally-obtained fluorescence emission maxima of correspondingly-substituted coumarocryptands of the invention. As the wavelength of the fluorescence emission maxima increases, potassium response (as seen from the $\phi_{DMO}/\phi_{EDO}$ ratio) declines. When the fluorescence wavelength exceeds 470 nm, potassium response becomes too small to be useful in commercial-type sensors.

Molecular modeling was used to screen for suitable sensors. Good potassium response was obtained when the ionophore exhibits (1) close-lying $S_2(n\pi^*)$ and $S_1(\pi\pi^*)$ excited states, such as those found with aromatic carbonyls, nitroaromatics, and N-heterocyclic systems; (2) a flexible out-of-plane vibrational mode involving linking the cryptand heteroatoms and heterocyclic heteroatoms; and (3) a fluorescence maximum at <480 nm.

Potential candidates can be screened using ground state molecular orbital calculations to predict the absorbance wavelength and excited state molecular orbital calculations to predict the fluorescence wavelength. Importantly, a majority of red-shifted coumarin derivatives do not satisfy the above criteria and do not make good potassium indicators.

Calculated emission and absorption wavelengths, Stokes shifts, and $K^+$ response (as defined previously) for EDO-type coumarin derivatives having various substitution patterns are shown in Table 16c. In the Table, $y_1$ and $y_2$ correspond to predicted absorption wavelengths and Stokes shifts, respectively, derived from calculated values according to equations (1) and (2), below. From FIG. 6(b) and FIG. 8, a simple empirical formula can be derived to correlate the observed "$K^+$ response" with observed emission wavelength, $\lambda_{em}$, of coumarin compounds:

$$K^+ \text{ response} = \exp^{0.0258(420-\lambda_{cm})} \tag{3}$$

Formula (3) was used to calculate $K^+$ response for coumarin derivatives as shown in Table 16c.

TABLE 16c

Calculated $K^+$ response for various coumarin-derivatives

| # | Structure | $\lambda_{abs}$ pred. (nm) $y_1$ | Stokes shift pred. (nm) $y_2$ | $\lambda_{em}$ (nm) ($y_1 + y_2$) | Calculated $K^+$ response |
|---|---|---|---|---|---|
| 1 | [structure with CH₃] | 346 | 76 | 422 | 0.95 |
| 2 | [structure with CF₃] | 354 | 107 | 461 | 0.35 |

TABLE 16c-continued

Calculated K⁺ response for various coumarin-derivatives

| # | Structure | $\lambda_{abs}$ pred. (nm) $y_1$ | Stokes shift pred. (nm)$y_2$ | $\lambda_{em}$ (nm) ($y_1 + y_2$) | Calculated K⁺ response |
|---|---|---|---|---|---|
| 3 | 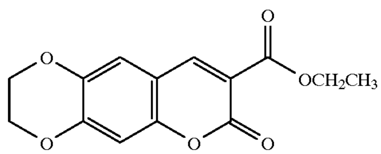 | 359 | 95 | 454 | 0.42 |
| C4 | 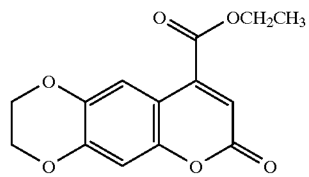 | 365 | 165 | 530 | 0.06 |
| 5 | 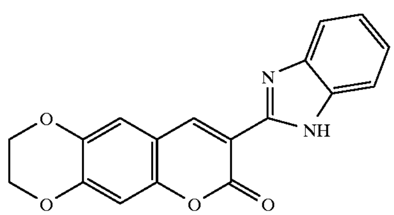 | 386 | 85 | 471 | 0.27 |
| 6 | 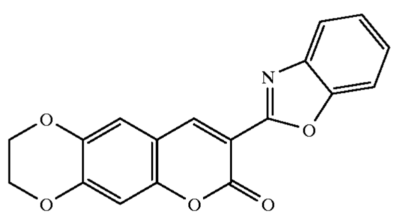 | 390 | 83 | 473 | 0.25 |
| 7 | 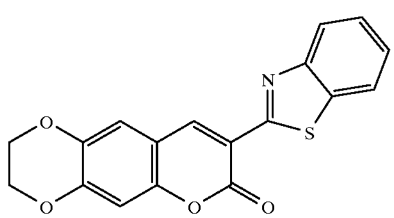 | 386 | 99 | 485 | 0.19 |
| 8 | 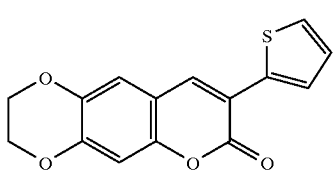 | 392 | 80 | 472 | 0.26 |
| 9 | 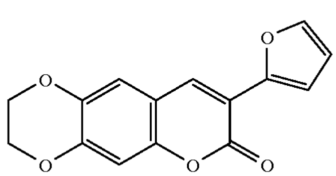 | 403 | 65 | 468 | 0.29 |

TABLE 16c-continued

Calculated K⁺ response for various coumarin-derivatives

| # | Structure | $\lambda_{abs}$ pred. (nm) $y_1$ | Stokes shift pred. (nm) $y_2$ | $\lambda_{em}$ (nm) ($y_1 + y_2$) | Calculated K⁺ response |
|---|---|---|---|---|---|
| 10 | 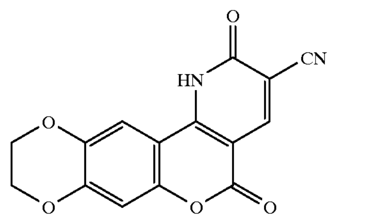 | 367 | 96 | 463 | 0.33 |
| 11 | 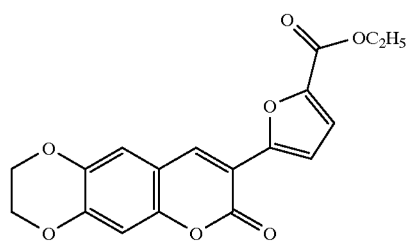 | 401 | 63 | 464 | 0.32 |
| 12 | 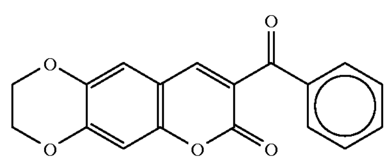 | 366 | 87 | 453 | 0.43 |
| 13 | 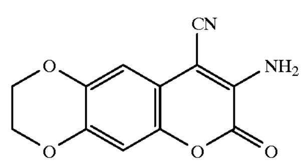 | 382 | 64 | 446 | 0.51 |
| C14 | 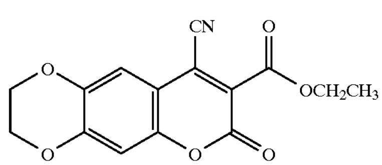 | 371 | 130 | 501 | 0.12 |
| 15 | 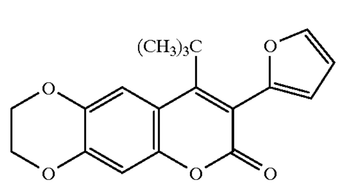 | 399 | 79 | 478 | 0.22 |
| 16 | 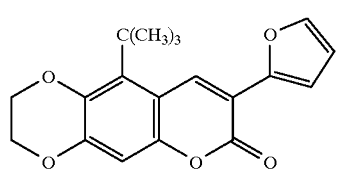 | 400 | 63 | 463 | 0.33 |

TABLE 16c-continued

Calculated K⁺ response for various coumarin-derivatives

| # | Structure | $\lambda_{abs}$ pred. (nm) $y_1$ | Stokes shift pred. (nm)$y_2$ | $\lambda_{em}$ (nm) ($y_1 + y_2$) | Calculated K⁺ response |
|---|---|---|---|---|---|
| 17 | 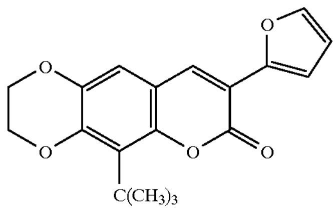 | 397 | 62 | 459 | 0.37 |
| 18 | 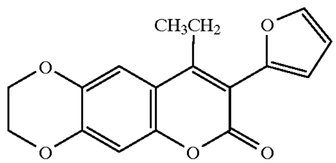 | 401 | 77 | 478 | 0.22 |
| 19 | 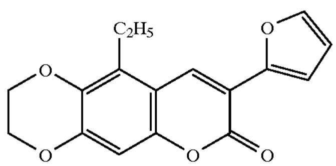 | 399 | 63 | 462 | 0.34 |
| 20 | 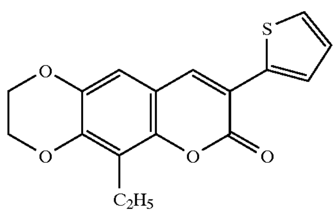 | 398 | 62 | 460 | 0.36 |
| 21 | 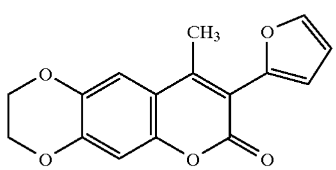 | 384 | 70 | 454 | 0.42 |
| 22 | 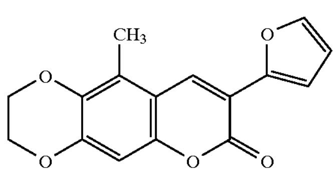 | 383 | 62 | 445 | 0.52 |
| 23 | 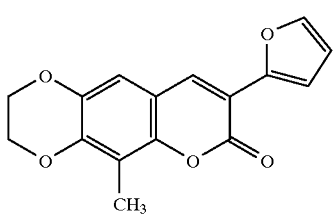 | 383 | 61 | 444 | 0.54 |

TABLE 16c-continued

Calculated K⁺ response for various coumarin-derivatives

| # | Structure | $\lambda_{abs}$ pred. (nm) $y_1$ | Stokes shift pred. (nm) $y_2$ | $\lambda_{em}$ (nm) ($y_1 + y_2$) | Calculated K⁺ response |
|---|---|---|---|---|---|
| 24 | 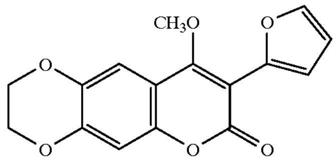 | 388 | 74 | 462 | 0.34 |
| 25 | 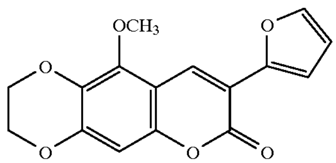 | 380 | 78 | 460 | 0.36 |
| 26 | 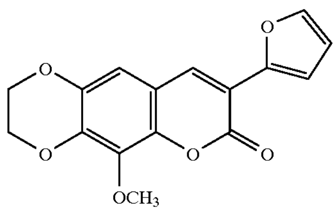 | 382 | 75 | 457 | 0.38 |
| 27 | 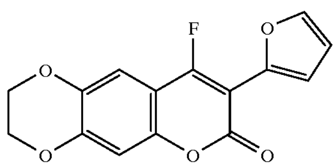 | 408 | 78 | 486 | 0.18 |
| 28 | 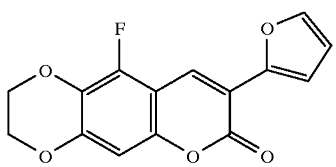 | 402 | 78 | 480 | 0.21 |
| 29 | 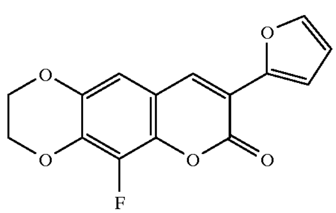 | 400 | 76 | 476 | 0.24 |
| 30 | 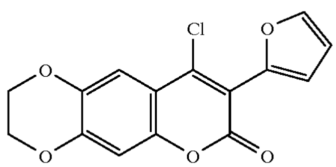 | 410 | 67 | 477 | 0.23 |

TABLE 16c-continued

Calculated K⁺ response for various coumarin-derivatives

| # | Structure | $\lambda_{abs}$ pred. (nm) $y_1$ | Stokes shift pred. (nm)$y_2$ | $\lambda_{em}$ (nm) ($y_1 + y_2$) | Calculated K⁺ response |
|---|---|---|---|---|---|
| 31 | 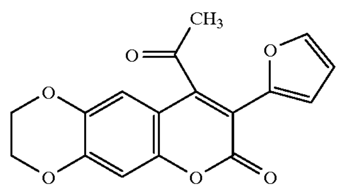 | 423 | 89 | 512 | 0.09 |
| 32 | 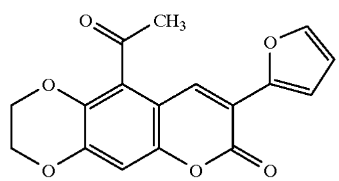 | 405 | 67 | 472 | 0.26 |
| 33 | 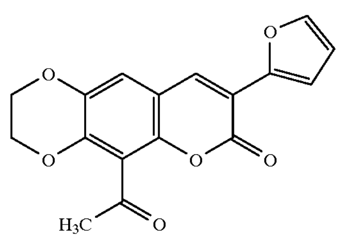 | 400 | 65 | 465 | 0.31 |
| 34 | 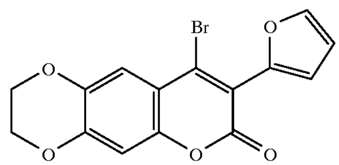 | 409 | 57 | 466 | 0.31 |
| C35 | 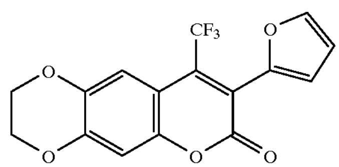 | 420 | 86 | 506 | 0.11 |
| 36 | 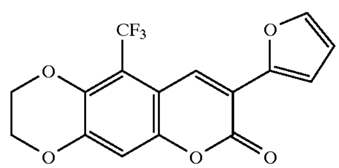 | 410 | 66 | 476 | 0.24 |
| 37 | 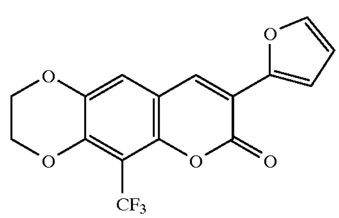 | 401 | 67 | 468 | 0.29 |

TABLE 16c-continued

Calculated K+ response for various coumarin-derivatives

| # | Structure | λ_abs pred. (nm) y_1 | Stokes shift pred. (nm) y_2 | λ_em (nm) (y_1 + y_2) | Calculated K+ response |
|---|---|---|---|---|---|
| C38 | 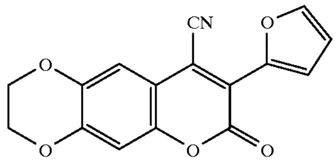 | 428 | 80 | 508 | 0.10 |
| 39 | 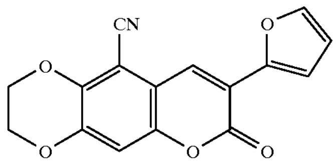 | 419 | 69 | 488 | 0.17 |
| 40 | 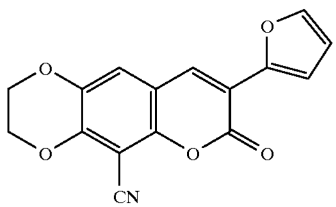 | 402 | 64 | 466 | 0.31 |
| 41 | 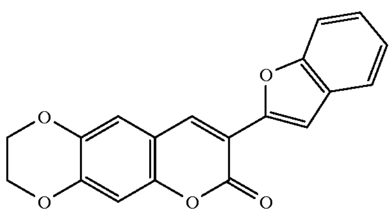 | 406 | 75 | 481 | 0.21 |
| 42 | 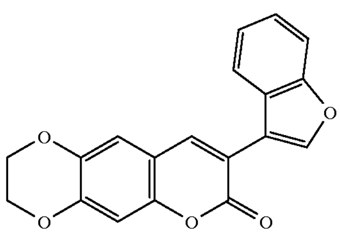 | 376 | 61 | 437 | 0.64 |
| 43 | 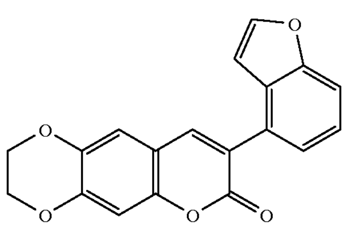 | 379 | 67 | 446 | 0.51 |
| 44 | 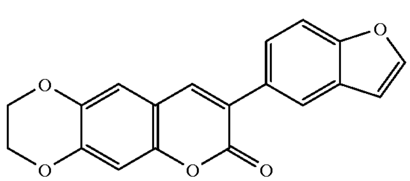 | 368 | 63 | 431 | 0.75 |

TABLE 16c-continued
Calculated K+ response for various coumarin-derivatives
| # | Structure | $\lambda_{abs}$ pred. (nm) $y_1$ | Stokes shift pred. (nm) $y_2$ | $\lambda_{em}$ (nm) ($y_1 + y_2$) | Calculated K+ response |
|---|---|---|---|---|---|
| 45 | 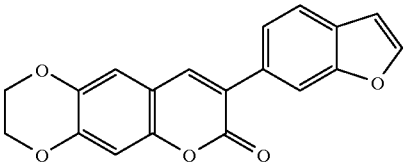 | 378 | 67 | 445 | 0.52 |
| 46 | 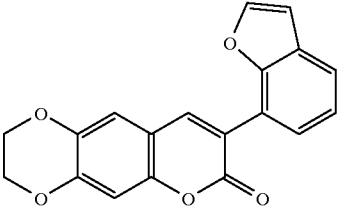 | 372 | 69 | 441 | 0.58 |
| C47 | 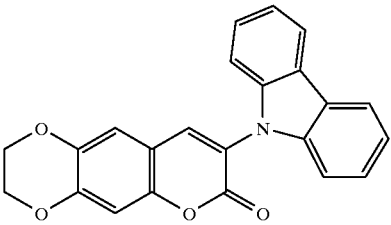 | 400 | 165 | 565 | 0.02 |
| 48 | 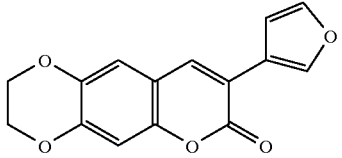 | 371 | 58 | 429 | 0.79 |
| 49 | 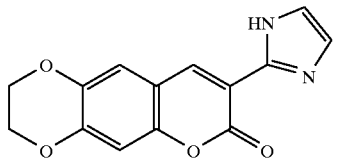 | 393 | 71 | 464 | 0.32 |
| 50 | 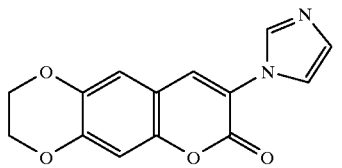 | 382 | 63 | 445 | 0.52 |
| 51 | 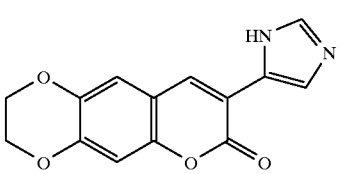 | 399 | 65 | 464 | 0.32 |

TABLE 16c-continued

Calculated K⁺ response for various coumarin-derivatives

| # | Structure | $\lambda_{abs}$ pred. (nm) $y_1$ | Stokes shift pred. (nm)$y_2$ | $\lambda_{em}$ (nm) ($y_1 + y_2$) | Calculated K⁺ response |
|---|---|---|---|---|---|
| 52 | 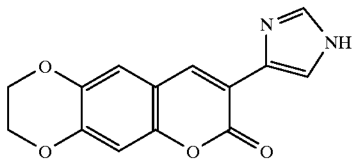 | 376 | 65 | 441 | 0.58 |
| 53 | 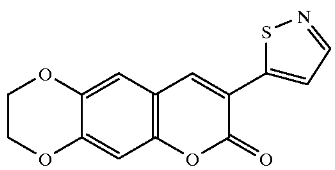 | 372 | 60 | 432 | 0.73 |
| 54 | 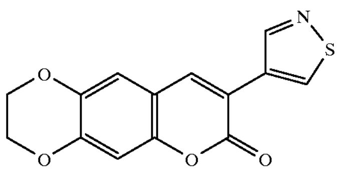 | 362 | 61 | 423 | 0.93 |
| 55 | 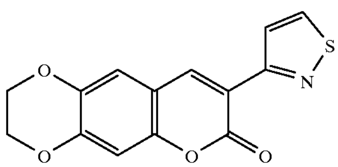 | 367 | 67 | 434 | 0.70 |
| 56 | 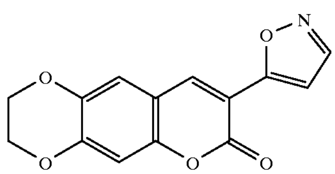 | 378 | 67 | 445 | 0.52 |
| 57 | 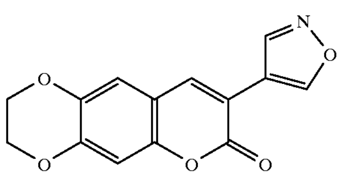 | 368 | 61 | 429 | 0.79 |
| 58 | 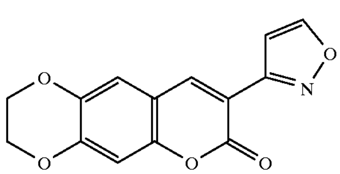 | 359 | 69 | 428 | 0.81 |
| 59 | 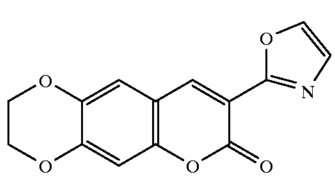 | 391 | 60 | 451 | 0.45 |

TABLE 16c-continued

Calculated K+ response for various coumarin-derivatives

| # | Structure | $\lambda_{abs}$ pred. (nm) $y_1$ | Stokes shift pred. (nm) $y_2$ | $\lambda_{em}$ (nm) ($y_1 + y_2$) | Calculated K+ response |
|---|---|---|---|---|---|
| 60 | 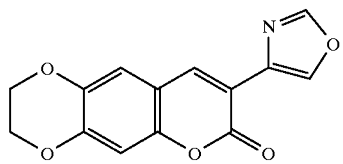 | 373 | 58 | 431 | 0.75 |
| 61 | 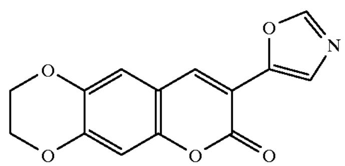 | 395 | 62 | 457 | 0.38 |
| 62 | 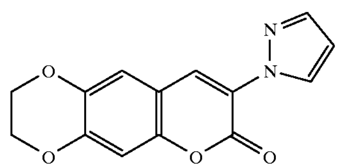 | 383 | 67 | 450 | 0.46 |
| 63 | 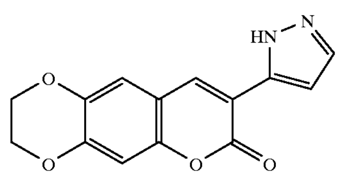 | 376 | 65 | 441 | 0.58 |
| 64 | 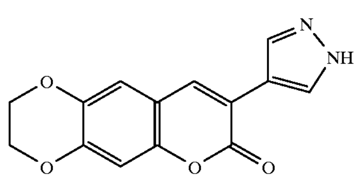 | 367 | 62 | 429 | 0.79 |
| 65 | 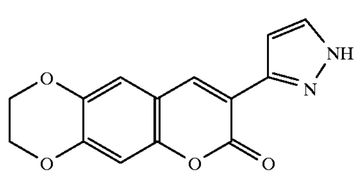 | 361 | 64 | 425 | 0.88 |
| 66 | 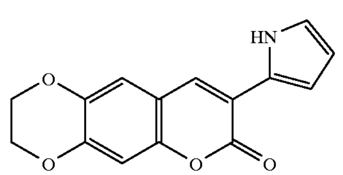 | 392 | 65 | 457 | 0.38 |
| 67 | 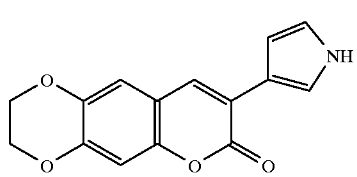 | 374 | 62 | 436 | 0.66 |

TABLE 16c-continued

Calculated K⁺ response for various coumarin-derivatives

| # | Structure | $\lambda_{abs}$ pred. (nm) $y_1$ | Stokes shift pred. (nm) $y_2$ | $\lambda_{em}$ (nm) ($y_1 + y_2$) | Calculated K⁺ response |
|---|---|---|---|---|---|
| 68 | 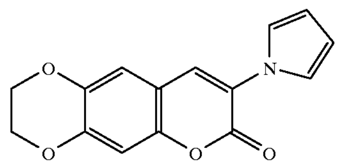 | 379 | 58 | 437 | 0.64 |
| 69 | 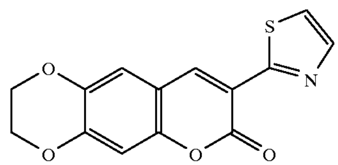 | 379 | 92 | 471 | 0.27 |
| 70 | 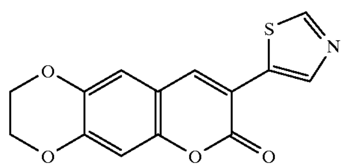 | 377 | 66 | 443 | 0.55 |
| 71 | 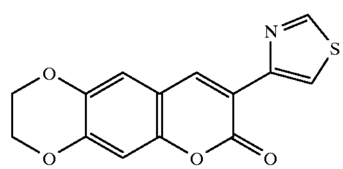 | 366 | 70 | 436 | 0.66 |
| 72 | 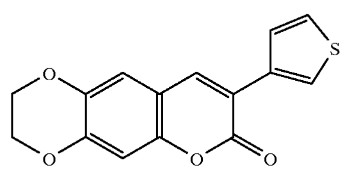 | 364 | 58 | 422 | 0.95 |
| 73 | 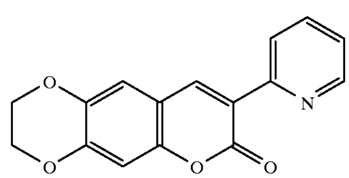 | 365 | 72 | 437 | 0.64 |
| 74 | 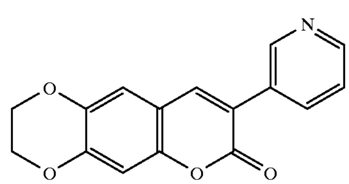 | 361 | 69 | 430 | 0.77 |
| 75 | 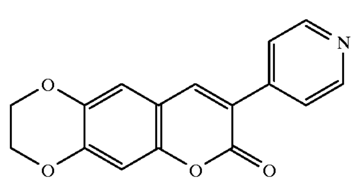 | 359 | 71 | 430 | 0.77 |

TABLE 16c-continued

Calculated K⁺ response for various coumarin-derivatives

| # | Structure | $\lambda_{abs}$ pred. (nm) $y_1$ | Stokes shift pred. (nm) $y_2$ | $\lambda_{em}$ (nm) ($y_1 + y_2$) | Calculated K⁺ response |
|---|---|---|---|---|---|
| 76 | 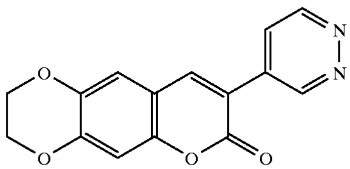 | 359 | 85 | 444 | 0.54 |
| 77 | 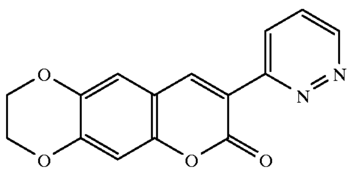 | 361 | 63 | 424 | 0.90 |
| 78 | 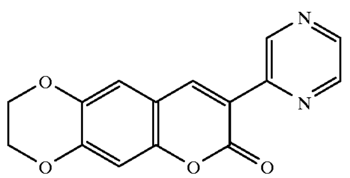 | 367 | 73 | 440 | 0.60 |
| 79 | 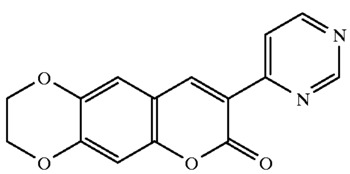 | 363 | 76 | 439 | 0.61 |
| 80 | 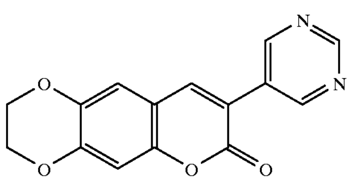 | 361 | 78 | 439 | 0.61 |
| 81 | 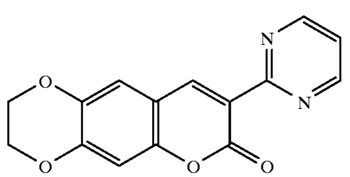 | 361 | 84 | 445 | 0.52 |
| 82 | 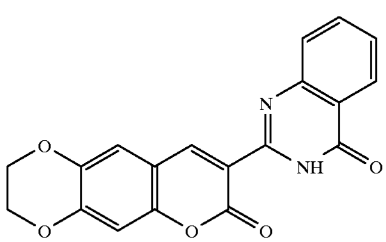 | 391 | 133 | 524 | 0.07 |

TABLE 16c-continued

Calculated K⁺ response for various coumarin-derivatives

| # | Structure | $\lambda_{abs}$ pred. (nm) $y_1$ | Stokes shift pred. (nm)$y_2$ | $\lambda_{em}$ (nm) ($y_1 + y_2$) | Calculated K⁺ response |
|---|---|---|---|---|---|
| 83 | 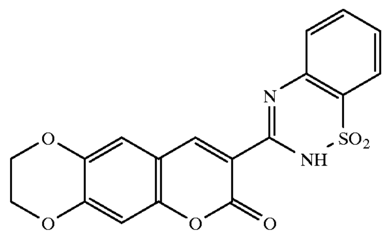 | 396 | 134 | 530 | 0.06 |
| 84 | 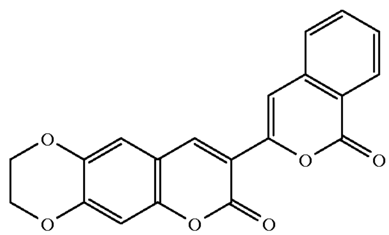 | 404 | 66 | 470 | 0.28 |
| 85 | 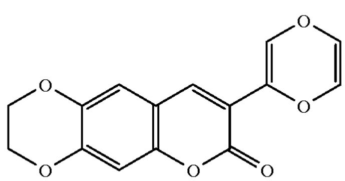 | 393 | 182 | 575 | 0.02 |
| 86 | 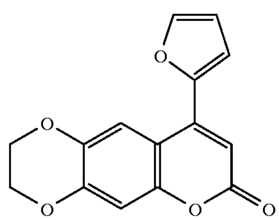 | 353 | 94 | 447 | 0.50 |
| 87 | 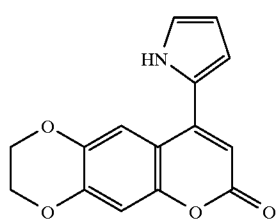 | 359 | 77 | 436 | 0.66 |
| 88 | 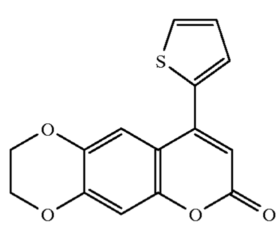 | 343 | 98 | 441 | 0.58 |

Initial molecular structures were constructed by using commercial molecular building software EDITOR (CAChe Scientific, Beaverton, Oreg.). Conformations of the $S_0$ ground state were determined by using two software packages: MM2 (CAChe Scientific) and MOPAC6.0 (using the PM3 parameter). Conformations of the $S_1(\pi\pi^*)$ excited state were determined by using MOPAC6.0(using the PM3 parameter) with restrict Hartree-Fock (RHF) open-shell configuration interaction calculations (CI). As part of geometry optimization, two type CI calculations were carried out: (a) small CI calculations (CI=2) using only the HOMO and LUMO (with MOPAC parameter MICROS=4 (or 3)) and (b) large CI calculations (10>CI>2) using all micro states with CI expansion coefficient in the $S_1(\pi\pi^*)$ state larger than 0.05 (MOPAC parameter MICROS=5 to 25 to ensure inclusion of all microstates).

The maximum absorption and fluorescence wavelengths for various molecules were determined by using either ZINDO, MOPAC6.0 (using the PM3 parameter), or LAN-LPAC with ground state and excited state molecular conformations, respectively, as input geometries. All results from ZINDO were obtained by using a configuration interaction (CI) window of 26 (13 occupied and 13 unoccupied orbitals). In MOPAC calculations, the energies of various excited states were determined using CI calculations employing 51 determental wavefunctions. These wavefunctions included 1 ground state configuration and 50 single excitations (from the 5 highest occupied molecular orbitals to the 5 lowest unoccupied molecular orbitals). Stokes shifts for each molecule can be determined from these calculations.

It was necessary to calibrate calculated absorption and fluorescence wavelengths to experimentally measured wavelengths for the class of molecules being studied. Typically, linear correlations exist between calculated and experimental wavelengths. From these established correlations and modeling results, absorption wavelengths, Stokes shifts, fluorescence wavelengths, and K$^+$ response for some novel derivatives could be predicted.

Figure 9A:
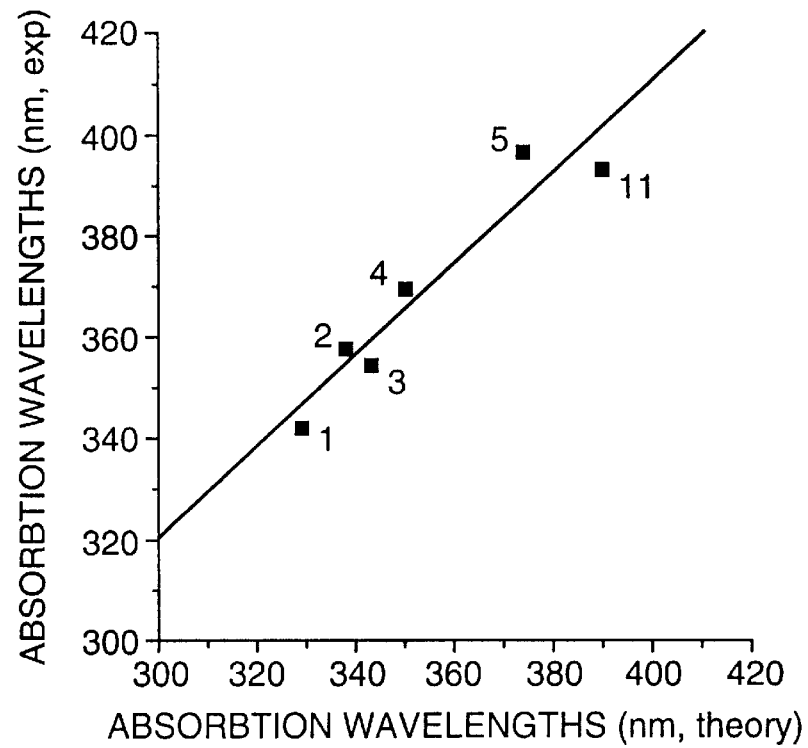
FIG. 9a shows a graphical representation of the correlation between calculated and measured absorption wavelengths of EDO-type model compounds.

Three combinations of modeling tools were used to calculate absorbance maxima: $\lambda_{abs}$ (PM3, ZINDO), $\lambda_{abs}$ (PM3, LANLPAC), and $\lambda_{abs}$ (MM2, ZINDO). Among results from these three methods, $\lambda_{abs}$ (MM2, ZINDO) gave the highest linear correlation with experimental data, as shown in FIG. 9a.

Absorption wavelengths calculated by this method for EDO-type compounds are plotted against experimentally-obtained absorption wavelenghts for coumarocryptands of the invention bearing identical substitution patterns in the presence of 8 mM potassium ion. Data point numbers in FIG. 9a correspond to chemical structures and substitution patterns shown in Table 16c. Once the theoretical absorption wavelenghts $x_i$ were calculated, they were converted into predicted absorption wavelengths $y_i$, reported in Table 16c, according to formula (1):

$$y_1 = 50.761 + 0.89757 x_1 \quad (1)$$

Three combinations of modeling tools were used to calculate emission maxima: $\lambda_{em}$ (PM3, CI=2, ZINDO), $\lambda_{em}$ (PM3, CI=2, LANLPAC), and $\lambda_{em}$ (PM3, CI>2, LANLPAC). Among results from these three methods, (PM3, CI>2, LANLPAC) gave the highest linear correlation with experimental data.

Figure 9B:
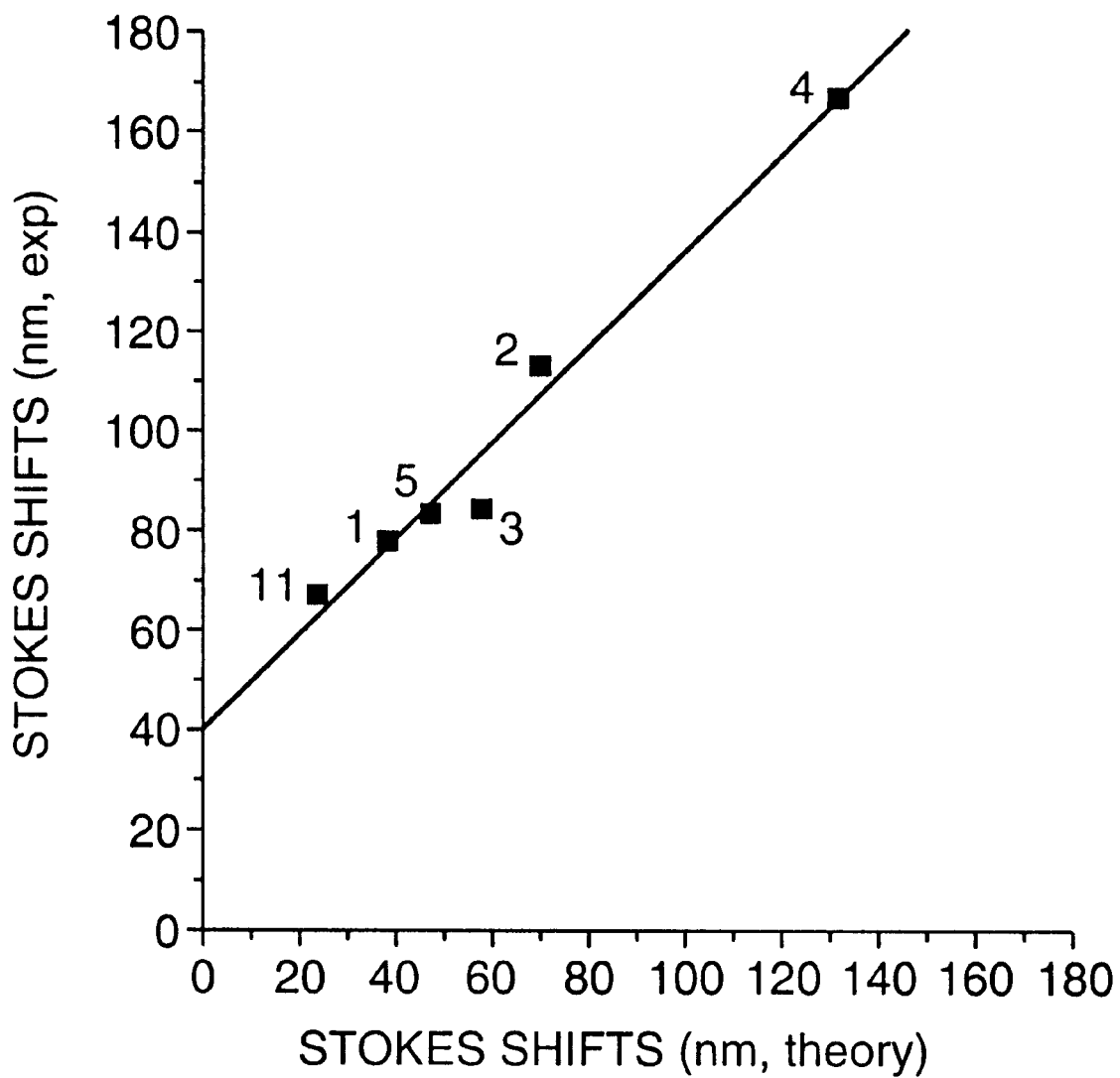
FIG. 9b shows a graphical representation of the correlation between calculated and measured Stokes shifts of EDO-type model compounds.

As shown in FIG. 9b, there exists a linear correlation between the theoretical Stokes shift for EDO-type model compounds $\{\Delta\lambda = \lambda_{em}(PM3, CI>2, LANLPAC) - \lambda_{abs}(PM3, LANLPAC)\}$ and the experimental Stokes shift for similarly-substituted coumarocryptand ionophores of the invention. Calculated values of Stokes shifts $x_2$ were converted into predicted values $y_2$ according to formula (2), and the predicted values are reported in Table 16c:

$$y_2 = 40.431 + 0.94421 x_2 \quad (2)$$

With reference to FIGS. 9a and 9b, it is clear that FCCC-ester (data point 11) offers the unique combination of a red-shifted absorbance and a small Stokes shift, such that the potassium response might remain substantial.

Based on the correlations established according to FIGS. 9a and 9b and formulas (1), (2), and (3), it is possible to screen for potential indicator candidates. Table 16c shows the structures of several EDO-type coumarin derivatives which we modeled and shows the theoretical (calculated) absorbance and emission maxima of the indicators.

Several conclusions can be drawn from the data of Table 16c:

(1) Five membered heterocycles at position 3 of the coumarin ring joined at a position alpha to the heteroatom provide the desired red-shift while maintaining K$^+$ response. The modeled five-membered heterocycles joined at a position beta to the hetereoatom do not;

(2) Electron-withdrawing substituents at the 4-position of 3-substituted coumarins significantly decrease K$^+$ response, relative to their unsubstituted analog or to 3-substituted coumarins with electron-donating substituents at the 4 position; and (3) Electron-withdrawing substituents at the 5 or 8 position of 3-substituted coumarins exhibit much less of an effect on K$^+$ response than do electron-withdrawing substituents at the 4-position.

Using similar methods, it may be possible to identify other classes of aromatic carbonyls, nitroaromatics and N-heterocyclic systems that have the close-lying $n\pi^*$ and $\pi\pi^*$ excited states necessary to support ionophore-based sensing.

Example 17

Clinical Trial of Potassium Sensor

Potassium sensor membranes were installed in a sensor cassette as described in Example 15, and the cassette was attached to a CDI/3M Health Care Model S400™ Clinical Monitor to be used to measure [K$^+$] in the blood of heart surgery patients. The membranes were aged for 11 months in pH 7.32 HEPES buffer prior to installation. A flash lamp was used to illuminate the sensor, and results were obtained through a 16-bit A/D converter, using LabVIEW™ software.

In these experimental trials, [K$^+$] was monitored in six heart by-pass surgical procedures relative to a Model 865 clinical blood-gas analyzer (B GA) (Ciba Corning Diagnostics Corp.; Medfield, Mass.) using either a two-point HEPES buffer syringe calibration or one standard [K$^+$] buffer and one blood point calibration. Potassium ion was monitored on channels 1 and 2 of a S400™ Monitor. In all cases, a constant offset of −1.8 mM K$^+$ concentration was observed.

Five or six data points were measured for each procedure. In Table 17a, the data points are designated M-N where M is the procedure and N is the data point.

The two-point HEPES buffer syringe calibration was carried out at [K$^+$] of 3 and 8 mM, pH 7.3, [Na$^+$] concentration of 139 mM, and blood temperature as shown. Data presented in Table 17a for this method are not adjusted for the −1.8 mM offset. For data with syringe and blood calibration, the syringe buffer point was constant at 9.8 mM (adjusted for 1.8 mM offset) and the blood point was between 3.6 and 4.4 mM K$^+$, depending on the clinical trial. Data presented in Table 17a for this method have been adjusted for the −1.8 mM offset.

TABLE 17a

| Clinical Trial (M-N) | Temp, (° C.) | K+, BGA (mM) | Two-point HEPES buffer calibration (mM K+) | | Syringe buffer plus blood point calibration (mM K+) | |
|---|---|---|---|---|---|---|
| | | | Ch. 1 | Ch. 2 | Ch. 1 | Ch. 2 |
| 1-1 | 25.4 | 4.1 | 3.5 | 3.2 | 4.8 | 4.6 |
| 1-2 | 18.5 | 4.0 | 2.7 | 2.6 | 4.0 | 4.0 |
| 1-3 | 19.6 | 4.5 | 2.9 | 2.8 | 4.3 | 4.2 |
| 1-4 | 18.4 | 3.6 | 2.0 | 2.0 | 3.3 | 3.3 |
| 1-5 | 28.0 | 4.2 | 2.2 | 2.1 | 3.3 | 3.3 |
| 2-1 | 24.8 | 3.3 | 2.2 | 2.1 | 3.8 | 3.8 |
| 2-2 | 18.7 | 4.4 | 2.5 | 2.5 | 4.4 | 4.4 |
| 2-3 | 18.9 | 3.1 | 1.5 | 1.5 | 3.2 | 3.3 |
| 2-4 | 27.6 | 2.7 | 1.2 | 1.2 | 2.6 | 2.7 |
| 2-5 | 34.3 | 3.9 | 2.0 | 2.3 | 3.5 | 3.8 |
| 3-1 | 28.0 | 6.0 | 4.2 | 4.2 | 5.8 | 5.8 |
| 3-2 | 19.9 | 4.3 | 2.6 | 2.4 | 4.3 | 4.3 |
| 3-3 | 18.6 | 3.1 | 1.5 | 1.4 | 3.0 | 3.1 |
| 3-4 | 18.4 | 2.4 | 0.4 | 0.6 | 1.5 | 2.0 |
| 3-5 | 24.2 | 2.4 | 0.3 | 0.6 | 1.3 | 2.0 |
| 3-6 | 30.6 | 3.1 | 0.7 | 1.2 | 1.8 | 2.6 |
| 4-1 | 23.9 | 3.9 | 2.2 | 2.4 | 4.0 | 4.0 |
| 4-2 | 18.8 | 3.6 | 1.8 | 1.9 | 3.6 | 3.6 |
| 4-3 | 19.8 | 3.5 | 1.6 | 1.7 | 3.4 | 3.3 |
| 4-4 | 18.6 | 2.8 | 0.8 | 1.0 | 2.4 | 2.5 |
| 4-5 | 24.9 | 2.7 | 0.7 | 0.9 | 2.1 | 2.2 |
| 4-6 | 32.0 | 4.1 | 1.9 | 2.1 | 3.4 | 3.5 |
| 5-1 | 15.9 | 4.1 | 2.1 | 2.3 | 4.3 | 4.3 |
| 5-2 | 18.0 | 3.8 | 1.7 | 1.9 | 3.8 | 3.8 |
| 5-3 | 18.8 | 3.3 | 1.3 | 1.6 | 3.3 | 3.4 |
| 5-4 | 27.5 | 4.2 | 2.1 | 2.3 | 4.0 | 4.0 |
| 5-5 | 34.4 | 3.3 | 1.3 | 1.5 | 2.9 | 3.0 |
| 6-1 | 27.1 | 3.8 | 1.7 | 1.9 | 4.0 | 3.9 |
| 6-2 | 25.7 | 4.0 | 1.7 | 1.9 | 4.0 | 4.0 |
| 6-3 | 26.9 | 4.3 | 2.0 | 2.1 | 4.3 | 4.2 |
| 6-4 | 32.7 | 4.4 | 2.1 | 2.0 | 4.2 | 3.9 |
| 6-5 | 36.9 | 4.9 | 2.9 | 2.6 | 4.7 | 4.3 |

The data from Table 17a show that, for potassium concentrations measured using the two-point HEPES buffer, 6 of the 64 potassium sample measurements fall outside of an error range of ±0.5 mM (relative to the BGA measurement) and 14 samples fall outside of the range of ±0.3 mM K+ concentration. For potassium concentrations measured using a single syringe buffer and a blood point, 10 of the 64 potassium sample measurements fall outside of an error range of ±0.5 mM and 21 samples fall outside of the range of ±0.3 mM [K+].

Data in Table 17a indicate that the potassium sensors of the invention showed adequate intensities and slopes after storage at 23° C. for 11 months at pH 7.32, over a blood pH range of 7.2–7.5, a temperature range of 18–36° C., and a [K+] range of 2.3–6.0 mM.

Example 18

6,7-[2.2.1]-cryptando-3-[2"-(5"-carboethoxy)furyl] coumarin (2.2.1-FCCC-ester)

A solution of 1.2 g 6,7-bis(2-iodoethoxy)-3-[2"-(5"-carboethoxy)furyl]coumarin (from Example 4), 0.4197 g 1,4,10-trioxa-7,13-diazacylopentadecane, and 1.019 g $Na_2CO_3$ in 160 mL acetonitrile was stirred and refluxed under nitrogen for 36 days. The cooled mixture was filtered and the solvent removed in vacuo, and the residue was triturated with three 100 mL portions hot hexane, three 100 mL portions hot ethyl acetate, then taken up in 100 mL chloroform and filtered. Removal of solvent gave a solid that was recrystallized from a mixture of 15 mL and 7 mL of an 85:15 (v/v) solution of cyclo-hexane/ethyl acetate. The resulting solid was dried at 0.1 mm Hg to give 0.49 g of the desired cryptand.

Example 19

6,7-[2.2.1]-cryptando-3-[2"-(5"-carboxy)furyl] coumarin (2.2.1-FCCC-acid)

The FCCC-ester of Example 18 was stirred with 7.8 mL THF to which was added 2.7 mL methanol. To this mixture was added a solution of 0.36 g lithium hydroxide monohydrate in 5.4 mL water. After stirring at 23° C. for 30 minutes, 8.1 mL aqueous 6N HCl was added, and stirring continued for 60 minutes. Solvent was stripped at 38° C. for 20 minutes via rotoevaporator, and the residue was repeatedly taken up in 25 mL methanol and 25 mL THF and stripped to remove water. Several days of drying the residue at 0.2 mm Hg gave 0.97 g of the desired acid (84.8 rel wt % by $H^1$ MMR).

Example 20

6,7-[2.1.1]-cryptando-3-[2"-(5"-carboethoxy)furyl] coumarin (2.1.1-FCCC-ester)

A solution of 1.2 g 6,7-bis(2-iodoethoxy)-3-[2"-(5"-carboethoxy)-furyl]coumarin (from Example 4), 0.3350 g 1,7-diaza-12-crown-4 (Acros Organics; Pittsburgh, Pa.), 1.019 g $Na_2CO_3$ in 160 mL acetonitrile was stirred and refluxed under nitrogen for 36 days. The cooled mixture was filtered and the solvent removed in vacuo, and the residue was triturated with three 100 mL portions of hot hexane, three 100 mL portions of hot ethyl acetate, then taken up in 100 mL chloroform and filtered. Removal of solvent gave a solid that was recrystallized from a mixture of 15 mL methyl alcohol and 7 mL of an 85:15 (v/v) solution of cyclohexane/ethyl acetate. The resulting solid was dried at 0.1 mm Hg to give 0.43 g of the desired cryptand.

Example 21

6,7-[2.1.1]-cryptando-3-[2"-(5"-carboxy)furyl] coumarin (2.1.1-FCCC-acid)

The FCCC-ester of Example 20 was stirred with 6.9 mL THF to which was added 2.5 mL methyl alcohol. To this mixture was added a solution of 0.342 g lithium hydroxide monohydrate in 5.0 mL water. After stirring at 23° C. for 30 minutes, 7.7 mL aqueous 6N HCl was added, and stirring continued for 60 minutes. Solvent was stripped at 38° C. for 20 minutes via rotoevaporator, and the residue was repeatedly taken up in 25 mL methyl alcohol and 25 mL THF and stripped to remove water. Several days of drying the residue at 0.2 mm Hg gave 0.97 g of the desired acid (64.5 rel wt % by $H^1$ NMR).

Example 22

2-Furfurylrhodanine

A solution of 68.4 g rhodanine, 128.35 g sodium acetate and 43 mL (49.8 g) 2-furaldehyde in 340 mL glacial acetic acid was heated to boiling for 30 minutes with occasional swirling. The solution was cooled slightly and poured into 2.6 L water. The resulting solid was collected and rinsed successively with 1.4 L water, 500 mL ethyl alcohol and 200 mL diethyl ether. Recrystallization from acetone gave 97.4 g 2-furfurylrhodanine.

Example 23

3-α-Furyl-3-thioketopropanoic acid

A solution of 34.0 g 2-furfrylrhodanine (Example 22) in 150 mL 15% (by weight) aqueous NaOH solution was

Example 24

3-α-Furyl-3-oximinopropanoic acid

A solution of 18.0 g hydroxylamine hydrochloride in 16 mL water was prepared by heating until all solids were dissolved, after which a solution of 22.0 g sodium ethoxide in 187 mL ethyl alcohol was added. The resulting salt precipitate was filtered off, and the filtrate was added to 20.0 g 3-α-furyl-3-thioketopropanoic acid (Example 23). The resulting solution was boiled for 30 minutes on a hot water bath, then cooled on ice and mixed with 60 mL 5% (wt.) aq. sodium hydroxide solution. The mixture was filtered, cooled, and acidified with 56 nL 10% (wt.) aq. HCl. The product was extracted into diethyl ether (5×10 mL) and the solution was dried over magnesium sulfate. Evaporation of solvent gave the desired oxime as an orange solid.

Example 25

2-Furfurylacetonitrile

A mixture of 3-α-furyl-3-oximinopropanoic acid (Example 24) in acetic anhydride (mixed in a ratio of 1 g:4.83 mL, respectively) was heated on a hot water bath under reflux for 30 minutes. Steam distillation of the resulting mixture gave an azeotrope of the desired nitrile and water at 90–100° C. The yellow azeotrope was extracted with diethyl ether and the residual aqueous phase was neutralized with saturated aq. sodium carbonate, then extracted again with diethyl ether. The combined ether solutions were dried over magnesium sulfate. Vacuum distillation of residues after removal of ether gave the desired nitrile at 105–115° C.

Example 26

1,2-bis-(2'-chloroethoxy)benzene

A solution of 6 g (0.03 mol) of 1,2-bis-(2'-hydroxyethoxy)benzene (prepared according to the procedure of Landini and Montanari) in 400 ml of toluene and 6 ml of pyridine was heated under nitrogen to 40° C. Excess thionyl chloride (9.2 ml, 0.13 mol) was added, with stirring, over a period of 25 minutes. The reaction mixture was heated to the boiling point (about 110° C.) and maintained at reflux for 3 hours. The solution was cooled to room temperature before being decanted and saved. The residue was broken up, dissolved in water, and extracted with toluene. The toluene solutions were combined and washed first with 2N HCl, then with a saturated sodium bicarbonate solution. The dried solution was evaporated in vacuo to give 4.5 g (64%) of crude product which was distilled by kugelrohr at aspirator pressure to give 4.43 g of an analytically pure sample, m.p. 55°–56.5° C. Spectroscopic analysis confirmed that the product was 1,2-bis-(2'-chloroethoxy)benzene.

Example 27

1,2-bis-(2'-chloroethoxy)benzaldehyde

This procedure is a modification of a method used in the synthesis of mesitaldehyde as described in *Org. Synth. Coll.*, vol. V, 49–51 (1973) and *Chem. Ber.*, 96, 308–13 (1963).

A solution of 25 g (0.11 mol) of the product of Example 26 in 60 ml of methylene chloride was cooled to 0° C. A total of 20 ml (0.18 mol) of titanium tetrachloride (Aldrich Chem. Corp.; Milwaukee, Wis.) was added by syringe over 30 minutes, under nitrogen, with stirring while the solution was maintained at the 0° C. reaction temperature. A solution of 13.5 g (0.117 mol) of 1,1-dichloromethyl methyl ether (Aldrich) in 10 ml of methylene chloride was added over 15 minutes at 0° C. Stirring at 0° C. was continued for 5 minutes. The solution was warmed for 20 minutes on a water bath until the solution reached room temperature. It was then refluxed for 15 minutes. After the solution had cooled, it was poured over crushed ice. After shaking the mixture in a separatory funnel, the methylene chloride layer was separated, and the aqueous layer was extracted with two 100 ml portions of chloroform. The chlorocarbon solutions were combined and washed extensively with first water, then a brine solution. The organic layer was dried and evaporated in vacuo to give 24.5 g of the aldehyde (87%) as an acrid, saffron-yellow solid with a m.p. 49°–51° C. Spectro-scopic analysis confirmed that the product was 1,2-bis-(2'-chloroethoxy)benzaldehyde.

Example 28

3,4-bis-(2'-chloroethoxy)phenol

This compound was initially prepared by Baeyer-Villiger oxidation of the benzaldehyde from Example 27 to the formate ester using 3-chloroperoxybenozoic acid or magnesium monoperoxyphthalate, followed by acid-catalyzed hydrolysis. However, upon scale up, this method led to catastrophic loss of product through decomposition. Therefore, an alternative to the Baeyer-Villiger method was used.

In a two-liter flask equipped with an overhead stirrer and a cooling bath was placed 162 g (0.616 mol) of the product of Example 27 and 1.5 liters of chilled (10° C.) methanol. To this solution was added 48 g of a 33% (by wt.) sulfuric acid solution which had been pre-cooled.

To 125 ml of methanol was added 94 g (0.83 mol) of a 30% (by wt.) hydrogen peroxide solution and this mixture was added over five minutes, with stirring and continued cooling, to the above solution. The resultant solution became turbid but, after two hours of stirring, it clarified.

The solution was decanted away from a brown oil (11 g, discarded) that had formed on the bottom of the reaction flask. The decanted solution was stirred overnight at room temperature. Methanol was stripped from the reaction mixture before 400 ml chloroform and 100 ml water were added to the crude product. This mixture was agitated.

After the layers separated, the aqueous layer was further extracted with chloroform. The chloroform layers were combined and washed with water to a neutral pH. The organic layer was then extracted with a solution of 30 g (0.75 mol) NaOH in 400 ml water followed by a second 200 ml portion of a similarly prepared NaOH solution. The aqueous extracts were combined, acidified with 200 ml 6N HCl, and extracted with 400 ml fresh chloroform. The chloroform layer was dried over sodium sulfate and passed through a 5 cm×5 cm plug of silica. On removal of the solvent, 84 g (54%) of a slightly brown solid was obtained. Proton NMR confirmed the structure of the product.

Example 29

4,5-bis-(2'-chloroethoxy)-2-hydroxybenzaldehyde

This key intermediate was prepared by the method which was used to introduce the aldehyde functionality to 1,2-bis-(2'-chloroethoxy)benzene in Example 27.

In 60 ml of methylene chloride, 12.4 g (49.4 mmol) of the crude phenol from Example 28 was treated with 16.3 ml (148 mmol) of titanium tetrachloride followed by 4.5 ml (50 mmol) of 1,1-dichloromethyl methyl ether to give 5.2 g (37%) of the key intermediate. This product was sublimed at oil pump vacuum to give 4.35 g of cream-white crystals having a m.p. of 102°–102.5° C. Spectroscopic analysis confirmed that the product was the key intermediate.

Example 30

6,7-bis-(2'-chloroethoxy)-3-carboethoxycoumarin
First method)

This method is a standard Knoevenagel condensation on the 2-hydroxybenzaldehyde of Example 29 and is based on the methods of Balaiah et al., *Proc. Indian Acad Sci.,* 16A, 68–82 (1942) (*Chem. Abs.,* 37, 1429 (1943)); Borsche et al., *Chem. Ber.,* 85, 198–202 (1952); Fukui et al., *Bull. Chem. Soc. Japan,* 35, 1321–23 (1962).

To 6.03 g (37.6 mmol) diethyl malonate (Aldrich) was added and thoroughly mixed 10 g (36 mmol) of the product of Example 29. This mixture was heated, under nitrogen, on a steam bath. After dissolution, two drops of piperidine were added. Heating was continued for 30 minutes. The solution was then cooled and diluted with ethanol until a slurry resulted. After filtration and air drying, 11.5 g (85%) of a tan powder were obtained. It had a m.p. of 102°–103.5° C. The Proton NMR spectrum was identical to that obtained for the product of Example 31.

Example 31

6,7-bis-(2'-chloroethoxy)-3-carboethoxycoumarin
(Second method)

This method, based on Bissel, *Synthesis,* 846–48 (1982), proved to be erratic and, when successful, gave a low yield. Its one advantage is that it provides Compound V directly from the phenol of Example 28, thus resulting in one less step.

A 0.9 g (4 mmol) portion of the phenol from Example 28 was mixed with 0.9 ml (5 mmol) diethyl ethoxymethylene malonate (Aldrich). To this solution was added 5 ml of a 1 M $ZnCl_2$ solution in ether (Aldrich) along with 40 ml methylene chloride. The solution was refluxed for 24 hours under nitrogen, freed of solvent by distillation under vacuum on a rotary evaporator at aspirator pressure, and quenched with water. This mixture was extracted with chloroform. Chromatography on a short column of alumina, using methylene chloride as the eluting solvent, gave 0.33 g (24%) of the product. Proton NMR showed that the product was 6,7-bis-(2'-chloroethoxy)-3-carboethoxycoumarin.

Example 32

6,7-bis-(2'-iodoethoxy)-3-carboethoxycoumarin
(First method)

This follows the procedure described in Example 3 of U.S. Pat. No. 5,162,525 for the corresponding 4-methyl derivative.

A 0.75 g (2.0 mmol) portion of the bis-chloroethoxycoumarin from Example 30 and 0.9 g (6 mmol) of sodium iodide were dissolved in 25 ml acetone. The solution was refluxed under nitrogen for 2 days. Thereafter, an additional 0.45 g sodium iodide was added. The solution was refluxed for another 24 hours. (It was later discovered that using methyl ethyl ketone in place of acetone shortens the total reaction time to approximately 24 hours.) A final 0.45 g of sodium iodide was added. Reflux was maintained for an additional 6 days. Acetone was added as needed to maintain the original reaction volume. The solution was cooled and evaporated in vacuo. The residue was extracted with a mixture of methylene chloride and chloroform. The chlorocarbon solution containing the product was washed with 10% sodium thiosulfate (to reduce to iodide any iodine that had formed), dried over sodium sulfate, and evaporated to dryness on a rotary evaporator. The residue was crystallized from ethanol to give 0.92 g (82%) of a light yellow powder having a m.p. of 164°–166° C. The proton NMR spectrum of the product was in agreement with that of the product of Example 34.

Example 33

4,5-bis-(2'-iodoethoxy)-2-hydroxybenzaldehyde

This Example provides one of two alternate routes to the bisiodoethoxycoumarin derivative in Example 34 (IV).

In 20 ml acetone were dissolved 2.21 g (14.7 mmol) sodium iodide and 1.37 g (4.91 mmol) of the product of Example 29. The solution was refluxed for four days. Thereafter, 10 ml acetone and a second portion of sodium iodide (0.73 g, 2.6 mmol) were added, and the solution was refluxed another 24 hours. The solution was cooled and filtered. Solvent was removed on a rotary evaporator, and the residue was dissolved in chloroform. After the chloroform solution was washed with water and dried with sodium sulfate, solvent was removed to give 2.05 g (89%) of product. Proton NMR confirmed the structure of the product.

Example 34

6,7-bis-(2'-iodoethoxy)-3-carboethoxycoumarin
(Second method)

To 1.73 g (10.8 mmol) of the bis-iodoethoxy-hydroxybenzaldehyde from Example 33 was added diethyl malonate, 2.1 g (4.6 mmol), and this mixture was heated on a steam bath. When the mixture had become homogeneous, two drops of piperidine were added. After the mixture had cooled, a precipitate formed. The solution was diluted with a few milliliters of ethanol and reheated to boiling on the steam bath. After the solution had cooled, it was filtered and the precipitate product retained. The product was a solid with a m.p. of 162°–165° C. Proton NMR confirmed the structure of the product.

Example 35

6,7-[2.2.2]-cryptando-3-carboethoxycoumarin

The method described in Example 4 of U.S. Pat. No. 5,162,525 for the corresponding 4-methyl derivative was used to prepare this coumarocryptand.

A 1.0 g (1.8 mmol) sample of bis-iodoethoxy-coumarin (from Example 32 or Example 34) and 0.47 g (1.8 mmol) of 1,4,10,13-tetraoxa-7,16-diazacycloctadecane (i.e., 4,13-diaza-18-crown-6) were separately dissolved in 50 ml portions of dry acetonitrile. The combined solutions (100 ml total) were refluxed under nitrogen for six days in the presence of 5 equivalents (0.94 g) anhydrous sodium carbonate. During the reaction, the coarse sodium carbonate was converted to an extremely fine powder. The cooled reaction mixture was filtered and the solution was evaporated to dryness in vacuo. The residue was dissolved in methylene chloride, and the solution was filtered. Evaporation of the methylene chloride using the rotary evaporator at aspirator pressure, followed by oil pump pressure, gave a yellow foam (>100% of the calculated yield). The crude product was purified by chromatography on deactivated neutral alumina first using methylene chloride to elute unreacted starting materials, followed by a 1–5% ethanol/methylene chloride mixture to elute the product. About 50% of calculated amount of the product was recovered, consisting essentially of the desired product (VI). LRMS FAB (triethanolamine) calculated m/e for $C_{28}H_{40}N_2O_{10}$ was 564.27, whereas the observed m/e was 587, [VIII(Na)]+; free [VII]+ was not observed. UV (phosphate buffered saline) $I_{max}$=374 nm, 312 nm. Fluorescence (phosphate buffered saline) showed $I_{ex}$=371 nm and $I_{em}$=453 nm.

The structure of a similarly prepared sample that was further purified by additional chromatography was confirmed by proton NMR.

Example 36

Hydrolysis of coumarocryptand of Example 35

A 0.25 g sample of the product of Example 35 was dissolved in 25 ml 2N HCl and heated on a steam bath for 30 minutes. Small amounts of methanol were added as needed to promote dissolution. Volatile components of the reaction (i.e., water, excess HCl, alcohols) were evaporated first on the rotary evaporator at aspirator vacuum, then quiescently at oil pump vacuum, to give the 3-carboxycryptandocoumarin hydrochloride salt, a pumpkin-yellow solid. Proton NMR confirmed the desired product.

Examples 37–39 describe the preparation of another coumarocryptand.

Example 37

6,7-bis-(2'-chloroethoxy)-3-(1'-oxo-4'-carboethoxybutyl)coumarin

Using the method described in Example 30, a solution of 2.12 g (7.60 mmol) of the product of Example 29 and 1.76 g (7.64 mmol) of diethyl 3-oxopimelate (Aldrich) in 100 ml ethanol was heated on a steam bath. About 20 drops of piperidine were added. The mixture was refluxed for thirty minutes and cooled to room temperature. The precipitate that formed was isolated by filtration and dried to yield 3.53 g (96%) of product. The structure of the product was confirmed by proton NMR.

Example 38

6,7-bis-(2'-iodoethoxy)-3-(1'-oxo-4'-carboethoxybutyl)coumarin

Using the method described in Example 32, a solution of 3.5 g (7.5 mmol) of the product of Example 12 and 3.4 g (23 mmol) anhydrous sodium iodide in 300 ml methyl ethyl ketone was heated to reflux under nitrogen for 48 hours. The mixture was cooled to room temperature, and the solvent was removed by rotary evaporation in vacuo. The residue was treated with about 20 ml water. The solid that remained was isolated by filtration and dissolved in toluene. The toluene was removed by rotary evaporator at reduced pressure to scavenge any residual water. The product was dried under high vacuum to afford 4.5 g (95%) of the desired product. Proton NMR was used to confirm the structure of the product.

Example 39

6,7-[2.2.2]-cryptando-3-(1'-oxo-4'-carboethoxybutyl)coumarin

The method described in Example 35 was adapted as follows: In a 250 ml flask equipped with a magnetic stirrer, reflux condenser, and a nitrogen purge source was placed 0.79 g (1.3 mmol) of the product of Example 38 dissolved in dry acetonitrile (45 ml, dried over silica gel and 0.4 nm molecular sieves, and distilled from calcium hydride). One equivalent (0.33 g) of 4,13-diaza-18-crown-6 was dissolved in a second portion (20 ml) of dry acetonitrile, and this solution was added to the first solution. The reaction mixture was heated to 70° C. before 0.62 g (5.8 mmol) sodium carbonate was added. The solution was refluxed under nitrogen for 7 days. Thereafter, 60 ml chloroform was added, and the solution was filtered.

After solvent was stripped, approximately 1 g of a yellow tacky oil was obtained. To the oil were added 60 ml chloroform and 20 ml brine, and this combination was mixed. The organic layer was separated and dried over sodium sulfate. Stripping the solvent gave 0.85 g of oily product. This was purified first by flash chromatography through a 2 cm×6 cm column of aluminum oxide powder (using 70 ml methylene chloride as the eluting solvent) to leave 0.65 g of product. This material was then carefully passed through a second column of aluminum oxide using a 1:2 mixture of methylene chloride/hexanes to give 370 mg (46%) of essentially pure product, a sticky yellow powder.

Proton NMR and IR spectroscopy was used to confirm the structure of the product. UV spectroscopy (phosphate-buffered saline) results: $l_{max}$382 nm, 317 nm.

Example 40

Comparison of Photostabilities of Coumarin Derivatives

The following model compounds were used to assess the effect on relative photostability of changes in functionality at the 3- and 4-position in coumarins.

Solutions of compounds VIII, IX, X, and XI in ethanol were prepared with absorbances in the range $0.05 \leq A_{max} \leq 0.1$, and each was continuously irradiated in a SPEX Fluorolog 2™ Series spectrofluorimeter (SPEX Industries, Inc.; Edison, N.J.) at maximum source slit widths (30 nm band pass) at $l_{max}$ for an hour. Measured luminance of the excitation source at the sample ranged from 30 to 50 mW/cm². The intensity of fluorescence was monitored throughout the duration of the irradiations at the emission maximum for each.

The data, normalized to X, are shown below in Table 40a. (The photostability of compounds VIII, IX, and X were measured in one experiment and that of compound XI in another, but the results are combined into a single Table for ease of comparison.)

The difference in the intensities at time zero reflects the relative fluorescence efficiencies of the derivatives. The 3-carboethoxy derivative (VIII) combines superior photostability with a slightly improved fluorescence efficiency over the 4-methyl derivative (IX) or carboxymethyl derivative (XI).

TABLE 40a

| | Intensity of Coumarins VII–XI | | | |
|---|---|---|---|---|
| Time (sec) | VIII | IX | X | XI |
| 0 | 6.94 | 6.15 | 1.00 | 8.97 |
| 120 | 6.95 | 5.99 | 1.00 | 8.90 |
| 240 | 6.94 | 5.82 | 1.00 | 8.74 |
| 360 | 6.93 | 5.78 | 1.00 | 8.60 |

TABLE 40a-continued

| | Intensity of Coumarins VII–XI | | | |
|---|---|---|---|---|
| Time (sec) | VIII | IX | X | XI |
| 480 | 6.93 | 5.68 | 1.00 | 8.47 |
| 600 | 6.91 | 5.57 | 1.00 | 8.34 |
| 720 | 6.91 | 5.52 | 1.00 | 8.22 |
| 840 | 6.90 | 5.45 | 1.00 | 8.10 |
| 960 | 6.90 | 5.39 | 1.00 | 7.98 |
| 1080 | 6.89 | 5.28 | 1.00 | 7.86 |
| 1200 | 6.88 | 5.21 | 1.00 | 7.76 |
| 1320 | 6.87 | 5.12 | 1.00 | 7.62 |
| 1440 | 6.87 | 5.04 | 1.00 | 7.52 |
| 1560 | 6.86 | 4.97 | 1.00 | 7.42 |
| 1680 | 6.85 | 4.89 | 1.00 | 7.31 |
| 1800 | 6.84 | 4.81 | 1.00 | 7.19 |
| 1920 | 6.84 | 4.74 | 1.00 | 7.09 |
| 2040 | 6.83 | 4.65 | 0.99 | 6.99 |
| 2160 | 6.82 | 4.55 | 1.00 | 6.89 |
| 2280 | 6.81 | 4.46 | 0.99 | 6.79 |
| 2400 | 6.81 | 4.37 | 0.99 | 6.68 |
| 2520 | 6.80 | 4.27 | 0.99 | 6.59 |
| 2640 | 6.79 | 4.22 | 1.00 | 6.50 |
| 2760 | 6.78 | 4.12 | 0.99 | 6.39 |
| 2880 | 6.77 | 4.05 | 0.99 | 6.29 |
| 3000 | 6.77 | 3.98 | 1.00 | 6.20 |
| 3120 | 6.76 | 3.92 | 0.99 | 6.11 |
| 3240 | 6.75 | 3.85 | 0.99 | 6.01 |
| 3360 | 6.74 | 3.76 | 0.99 | 5.92 |
| 3480 | 6.73 | 3.70 | 0.99 | 5.83 |
| 3600 | 6.72 | 3.64 | 0.99 | 5.74 |

Example 41

Response of Coumarocryptand of Example 35 to Changes in [K$^+$] at Physiological Concentrations An approximately $10^{-5}$ M solution of the product of Example 35 ($A_{372nm}$=0.1) was prepared with sodium-only phosphate-buffered saline (20° C., pH=7.36, [Na$^+$]=134 mM, [K$^+$]=0 mM, [Cl$^-$]=64 mM). Aliquots (36 μl) of phosphate-buffered saline having [K$^+$]=0.2 M were added to 3 ml of solution in a cuvette to change [K$^+$] in 2.4 mM steps from 0 to 12 mM. At each step, the fluorescence emission intensity was measured from 400 to 600 nm at an excitation wavelength of 270 nm.

The data were normalized to the intensity at [K$^+$]=0 mM and I=445 nm. The normalized data, shown in Table 41a, demonstrate the regular increase in fluorescence intensity with increasing [K$^+$]. Increasing the [Na$^+$] to 145 mM changed the fluorescence only slightly. Similar results were obtained for the product of Example 39.

TABLE 41a

| | Intensity with Increasing [K$^+$] | | | |
|---|---|---|---|---|
| λ | 0 mM | 2.4 mM | 4.8 mM | 9.6 mM |
| 400 | 0.059 | 0.061 | 0.060 | 0.060 |
| 410 | 0.227 | 0.229 | 0.238 | 0.238 |
| 425 | 0.659 | 0.692 | 0.707 | 0.725 |
| 430 | 0.779 | 0.826 | 0.861 | 0.892 |
| 445 | 1.000 | 1.086 | 1.135 | 1.177 |
| 450 | 0.996 | 1.088 | 1.144 | 1.196 |
| 460 | 0.966 | 1.057 | 1.102 | 1.186 |
| 470 | 0.839 | 0.918 | 0.971 | 1.033 |
| 480 | 0.701 | 0.778 | 0.809 | 0.859 |
| 490 | 0.552 | 0.616 | 0.648 | 0.684 |
| 500 | 0.423 | 0.472 | 0.506 | 0.531 |
| 510 | 0.331 | 0.363 | 0.392 | 0.411 |
| 520 | 0.248 | 0.273 | 0.293 | 0.305 |

TABLE 41a-continued

| | Intensity with Increasing [K$^+$] | | | |
|---|---|---|---|---|
| λ | 0 mM | 2.4 mM | 4.8 mM | 9.6 mM |
| 530 | 0.183 | 0.200 | 0.220 | 0.230 |
| 540 | 0.138 | 0.152 | 0.155 | 0.166 |
| 550 | 0.096 | 0.110 | 0.121 | 0.129 |
| 560 | 0.070 | 0.080 | 0.087 | 0.090 |
| 570 | 0.054 | 0.058 | 0.063 | 0.065 |
| 580 | 0.038 | 0.044 | 0.048 | 0.050 |
| 590 | 0.028 | 0.030 | 0.037 | 0.037 |
| 600 | 0.021 | 0.024 | 0.028 | 0.027 |

Example 42

Functionalization of a Coatable Polymer with Molecular Tethers

In one liter of tetrahydrofuran (THF) at room temperature was dissolved 20 g poly(vinylchloride)-carboxylated (PVC-COOH) polymer, 1.8% COOH, (Aldrich). To this was rapidly added 75 ml of a solution of 4.9 g (3 equivalents) dicyclohexylcarbodiimide (DCC) (Aldrich) in THF. After the mixture was stirred in a capped flask at room temperature for 30 to 60 minutes, 72 g (10 equivalents) Jeffamine ED-900™ bis(2-aminopropyl)polyethylene glycol 800 (available from Fluka Chemical Corp.; Ronkonkoma, N.Y.) was rapidly added to the activated polymer solution to provide a cloudy solution/suspension. This was stirred, at room temperature, for 18 hours. The solution was concentrated to approximately 300 ml on a rotary evaporator (60° C.) and slowly added to a rapidly stirred container of water (approximately 18 liters). (A low shear movement, i.e., swirling, of the water is necessary to avoid small particulates and to provide a polymer precipitate that can be readily filtered and purified.)

The polymer was removed from the water and filtered using a plastic mesh sheet, then suspended in about 500 ml methanol and again filtered. The polymer was suspended in methanol and filtered two additional times to reduce the residual water and remove reaction byproducts before being dried under vacuum.

The polymer was redissolved in about one liter THF at room temperature and filtered, first through a polypropylene filter cloth and then through a polyethylene Buchner funnel (350–600 ml) containing a thick (3 to 4 cm) pad of Celite™ 545 (Fisher Scientific; Pittsburgh, Pa.) diatomaceous earth on a poly(propylene) filter cloth. The clear filtrate was collected and concentrated to 200 ml on a rotary evaporator at 60° C.

Reprecipitation of the polymer solution in water and filtration of the polymer was conducted as described above. Fine chopping of the polymer in water (using a blender) was performed as a final step prior to vacuum drying.

An infrared spectrum of the functionalized polymer film was acquired to confirm the reaction (i.e., the disappearance of the 1720 cm$^{-1}$ absorbance characteristic of the COOH group). Gel permeation chromatography of the polymer showed that the molecular weight was essentially unchanged from that of the PVC-COOH starting material (i.e., 160,000 to 220,000 depending on the PVC-COOH lot).

The procedure of Sarin et al., *Anal. Biochem.*, 117, 147 (1981) was adapted as follows to determine the concentration of available primary amine (from the bis(2-aminopropyl)poly(ethylene glycol)). To a 20 mg sample of dry polymer in a test tube was added (a) 0.40 ml of a solution of phenol and KCN in pyridine and (b) 0.10 ml of a solution of ninhydrin in ethanol (both of which were prepared as described in the reference). A test blank was similarly prepared. Both test tubes were heated at 100° C. for approximately ten minutes. Both were cooled in a cold water bath before 2 ml tetrahydrofuran (THF) was added to each. After the contents of the tubes were transferred to separate 25 ml volumetric flasks, they were diluted to 25 ml with THF. UV spectroscopy ($l_{abs}$=604 nm), with an extinction coefficient of $1.2 \times 10^4$ $M^{-1}cm^{-1}$, was used to determine ninhydrin concentration. From this, the concentration of available amine was determined to be 0.2 mmol/g of polymer.

Example 43

Attachment of Compound VII to Coatable Polymer

A 200 mg sample of the PVC/bis(2-aminopropyl)-poly(ethylene glycol) from Example 42 was dissolved in 10 ml dimethylformamide (DMF). A second solution of 50 mg (approximately 90 mmol) of hydrolyzed VII in 2 ml DMF was also prepared. To the second solution were added 42 ml (0.27 mmol) diisopropylcarbodiimide (Aldrich) and 40 mg (0.27 mmol) hydroxybenzylthiazole (Aldrich), and this mixture was stirred for about 20 minutes before being added to the first solution. (The flask holding the second solution was washed with 1 ml DMF to ensure complete transfer.) To the combined mixture was added 50 ml (0.27 mmol) dfisopropylethylamine (Aldrich). This was allowed to stir, under nitrogen atmosphere and in darkness, overnight.

The volume of solvent was reduced by rotary evaporation at 40° C. The concentrated solution was added slowly, with stirring, to 200 ml water. A flocculent precipitate was collected by pouring the aqueous suspension over an 80-mesh screen. The precipitate was washed four times with water and three times with methanol. After the precipitate was chopped into finer pieces with a razor blade, it was washed three more times in methanol. The functionalized polymer was dried in vacuo.

The method of Kaiser et al., *Anal. Biochem.*, 34, 595 (1970) using ninhydrin as reagent indicated greater than 95% of the amine groups of the tethered bis(2-aminopropyl) poly(ethylene glycol) had been consumed, presumably via coupling with VII.

Example 44

Coating of Functionalized Polymer on a Porous Membrane

A 2% (w/w) solution of the functionalized polymer from Example 43 in a 90/10 (v/v) mixture of THF and water was extrusion coated onto a roll (27.9 cm wide, 79 mm thick) of hydrophilic porous polypropylene (see WO 92/07899) using a six inch-wide slot-fed knife die. (The HPPP web had a maximum pore size of 1.3 mm and a porosity of 77%.) The web speed was 3 m/min, and the solution delivery rate was 67 ml/min.

The coated web was passed through an air floatation oven (15.6° C.) to evaporate solvent. The resultant dry coating weight was about 2.5 g/m$^2$.

Exposure to 0 and 8 mM K$^+$ solutions and calculation of the percent response suggested that an asymmetric functionalized polymer coating had been distributed throughout the internal pore surface area of the HPPP web with a predominance of material added to the side of the membrane that contacted the die.

Example 45

Testing of Coated Membrane

Circular disks were punched from the coated HPPP membrane of Example 44. These were used to test the reversibility, pH-dependence, and stability (both in buffer and in blood) of the sensing composite.

Reversibility

The reversibility of the sensor to changes in potassium ion concentration was determined by measuring sensor fluorescence intensity using a CDI™ S400 monitor (CDI/3M Health Care; Tustin, Calif.) which provided an excitation source at 395 nm and detected fluorescence at wavelengths greater than 440 nm. Potassium ion concentration was varied by rapidly circulating a 50 mM N-(2-hyl)piperazine-N-(ethanesulfonic hydroxyethyl)piperazine-N'-(ethanesulfonic acid) buffer (Sigma Chemical Corp.; St. Louis, Mo.), hereinafter designated as HEPES, containing approximately 138 mM NaCl, to which was added sufficient KCl to make the [+]2, 4, 6, or 8 mM. Fluorescence intensity was measured after eight minutes of equilibration, although actual sensor response time (to changes in the analyte K$^+$ concentration) was rapid (i.e., about 30 to 120 seconds). Results of these measurements are given in Table 45a.

TABLE 45a

| | | Fluorescence Intensity | | |
|---|---|---|---|---|
| Time (min) | [K$^+$] | Disk 1 | Disk 2 | Disk 3 |
| 0 | 2 | 724 | 700 | 676 |
| 8 | 4 | 748 | 720 | 695 |
| 16 | 6 | 762 | 734 | 711 |
| 24 | 8 | 770 | 743 | 720 |
| 32 | 6 | 763 | 736 | 712 |
| 40 | 4 | 748 | 722 | 698 |
| 48 | 2 | 722 | 700 | 678 |

Table 45a shows that sensors prepared as in Example 44 are reversible with respect to changes in potassium ion concentration which exceed those normally observed during bypass surgery (i.e., 3 to 6 mM).

pH-Dependence

Change in sensor fluorescence intensity as a function of pH of the aforementioned HEPES buffer at K$^+$ concentrations of 2, 4, and 6 mM were measured with a CDI™ S400 monitor. The results of these measurements are given in Table 45b.

TABLE 45b

| | Sensor Intensity at Various [K$^+$] | | |
|---|---|---|---|
| pH | 2 mM | 4 mM | 6 mM |
| 7.07 | 356 | 373 | 398 |
| 7.34 | 346 | 366 | 391 |
| 748 | 339 | 366 | 386 |
| 7.69 | 334 | 363 | 385 |
| 7.90 | 326 | 353 | 380 |

Table 45b shows that sensors prepared as in Example 44 exhibit small changes in response (to changing [K$^+$]) with changing pH, especially in the physiological pH range. More particularly, change in fluorescence intensity of the sensor at physiological pH range (i.e., about 7.3 to 7.5) and at physiological potassium ion concentrations (i.e., about 4 mM) constitutes about 2% of the total fluorescence change observed from pH=7.07 to pH=7.90. This compares with a pH dependence of about 6% or more for the same coumarocryptand bound to non-PVC matrices and an even larger dependence for the non-immobilized coumaro-cryptand in an aqueous buffered solution of the same pH range.

Stability

Stability of the sensing composite was measured both in a buffer solution and in blood.

A. Buffer

A 50 mM solution of HEPES containing 138 mM NaCl, as measured by an AVL 9120™ sodium/potassium analyzer (AVL Scientific Corp.; Roswell, Ga.), was maintained at a constant temperature of 24° C. in a Lauda™ RC 20 thermostated water bath (Lauda Dr. R. Wobser GmbH & Co. KG; Germany) and circulated through a sensor loop by means of a model 13400 peristaltic pump (Sarns/3M Health Care; Ann Arbor, Mich.). The pH of the solution, which ranged from 7 to 8, was monitored with an Orion™ pH meter (Orion Research; Cambridge, Mass.). Osmolality of the solution, which ranged from 285 to 305 mOsm, was measured on an Advanced Wide-Range Osmometer 3W2™ (Advanced Instrument Inc.; Needham Heights, Mass.). The [$K^+$] of the buffer solutions was determined with an IL 643™ flame photometer (Instrumental Laboratories; Lexington, Mass.).

Two sets of [$K^+$] "step" experiments were performed (both at room temperature). First, [$K^+$] was alternated between 0 and 8 mM. A sensing composite as described in Example 44 was allowed to equilibrate with the 0 mM KCl solution before being exposed to the 8 mM solution, whereupon the sensing composite was allowed to equilibrate for 5 to 10 minutes at the new [$K^+$] (although complete equilibration was quite rapid). This process was repeated five times over a period of five hours. The fluorescence intensity of both solutions (i.e., approximately 488 counts for the 0 mM solution and approximately 567 counts for the 8 mM solution as measured on a CDI™ S400 monitor) remained virtually unchanged over the length of the experiment.

The second "step" experiment involved [$K^+$] of 3 and 7 mM which is the concentration range normally encountered in bypass operations, as measured by an IL 643™ flame photometer. A sensing composite was allowed to equilibrate with the 3 mM KCl solution before being exposed to the 7 mM solution, whereupon the sensing composite was allowed to equilibrate for several minutes at the new [K+] (even though complete equilibration occurred within about 90 seconds). This process was repeated five times over a period of about three and one-half hours. The fluorescence intensity for both solutions (i.e., approximately 647 counts for the 3 mM solution and approximately 677 counts for the 7 mM solution as measured on a CDI™ S400 monitor) remained virtually unchanged over the length of the experiment.

B. Blood

Bovine blood was adjusted to a [$Na^+$] of 138 mM and an osmolality of 300 mOsm, as described in the previous section. Potassium ion concentrations of approximately 3 and 9 mM were obtained by addition of KCl, as described previously. Blood pH was maintained at about 7.34±0.02, as measured by an ABL-4™ blood gas analyzer (Radiometer A/S; Copenhagen, Denmark), by continuous sparging with a gas composition of 2.8% $CO_2$, 5.5% $O_2$, 91.7% $N_2$. The blood solutions were stored in a thermostated water bath and, after being introduced into the testing loop, circulated by means of a peristaltic pump. (See previous section.) The sensors were secured to CDI™ S400 cassettes and CDI™ Model 6730 Quik-cell blood gas monitoring units, ⅜ in. size (CDI/3M Health Care).

To alternate the two [$K^+$] solutions, initial sensor intensities were obtained with the 3 mM solution, and the test loop was emptied before the 9 mM solution was introduced directly. When this process was reversed, the test loop was rinsed with a wash solution of blood with [$K^+$]=3 mM to prevent contamination of the 3 mM test solution. (This washing process caused the sensor to be exposed to air between blood solution changes, which resulted in an increase in the sensor response time. It was found that hydrating the sensor in a HEPES buffer solution containing 8 mM $K^+$ and a small amount of a surfactant such as Triton™ X-100 or Tween™ 80 (both available from Aldrich), preferably the latter due to its approval for internal drug applications, produced stable sensor intensities.)

Without using an intermediate wash bath between blood solution changes, the response time (95%) when going from a [$K^+$] of 3 to 9 mm was about 40 seconds and about 65 seconds when going from 9 to 3 mM.

The sensors displayed good stability over a period of about five hours. The intensity produced by the 9 mM solution decreased slightly (i.e., approximately 5 counts) over the course of the testing, but this was believed to be due to dilution of this solution by the 3 mM solution with which it was alternated.

Various modifications and alterations of this invention will be apparent to those skilled in the art without departing from the scope and spirit of this invention, and it should be understood that this invention is not limited to the illustrative embodiments set forth herein.

What is claimed is:

1. A fluorescent ionophoric compound, comprising:
   a complexing moiety for selective binding of an ion; and
   a fluorescing moiety that contains close-lying $n\pi^*$ and $\pi\pi^*$ excited states, wherein the compound has a wavelength of maximum absorbance of at least about 350 nm;
   wherein the ionophoric compound has the general formula;

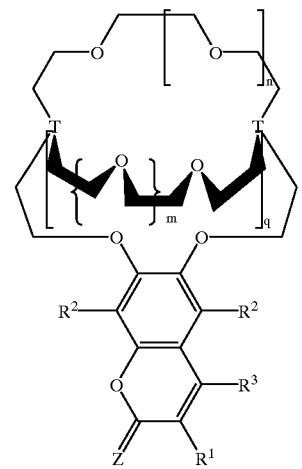

wherein;
   T is O or N, with the proviso that when T is O, q is 0 and n is 0 to 2, and when
   T is N, q is 1 and m and n are independently 0 or 1;
   each $R^2$ independently is selected from the group consisting of: hydrogen, halogen, a $C_1$–$C_{10}$ alkyl, a $C_1$–$C_{10}$ alkoxy, a $C_2$–$C_{10}$ alkenyl, a $C_1$–$C_{10}$ alkylamino, a $C_1$–$C_{10}$ dialkylamino, and a group having the formula $(CH_2X)_aE$ in which X is O, NH, or a single bond, E is a tonal group that includes active hydrogen, and a is a whole number from 1 to 10;

$R^3$ is selected from the group consisting of: hydrogen, a $C_1$–$C_{10}$ aryl, a $C_5$–$C_8$ cycloalkyl, a $C_6$–$C_{10}$ aryl, a heterocyclic group comprising at least one O, N, or S atom, a $C_2$–$C_{10}$ alkenyl, and a group having the formula $(CH_2X)_bE$ in which X and E are defined above and b is a whole number from 0 to 10;

$R^1$ is a substituted heterocyclic or aromatic moiety and

Z is O or $NR^5$, where $R^5$ is hydrogen or a hydrocarbyl-containing group.

2. The compound of claim 1, wherein:

$R^1$ in a substituted heterocyclic moiety having the general formula:

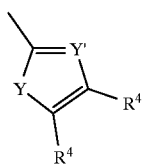

wherein

Y and Y' independently are O, S, $N_x$, or $CH_y$ where x is 0 or 1 and y is 1 or 2, with the proviso that at least one of Y and Y' must be O, S, or $NH_x$, and each $R^4$ group is independently selected from the group consisting of hydrogen, halogen, a hydrocarbyl-containing group, a hetero-acyclic group, a heterodic group, or a group having the formula $(CH_2X)_cE$ in which X is O, NH, or a single bond, E is a functional group that includes active hydrogen, and c is a whole number from 0 to 100, or both $R^4$ groups together with the carbon atoms to which they are attached form a 5- or 6-membered ring which optionally can have one or more further $R^4$ groups attached.

3. The compound of claim 1, wherein:

$R^1$ is a substituted heterocyclic moiety having the general formula:

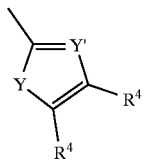

wherein

Y and Y' independently are O, S, $NH_x$, or $CH_y$ where x is 0 or 1 y is 1 or 2, with the proviso that at least one of Y and Y' must be O, S, or $NH_x$, and each $R^4$ group is independently selected from the group consisting of hydrogen, halogen, a $C_1$–$C_{20}$ alkyl, a $C_1$–$C_{20}$ alkoxy, a $C_3$–$C_{18}$ cycloalkyl, a $C_6$–$C_{18}$ aryl, a $C_6$–$C_{18}$ aryloxy, a $C_6$–$C_{18}$ hydroxyaryl, a $C_6$–$C_{18}$ arylcarboxy, a $C_6$–$C_{18}$ carboxyaryl, a $C_2$–$C_{18}$ alkenyl, a $C_1$–$C_{20}$ hydrocarbylamino, a $C_6$–$C_{18}$ arylamino, a $C_6$–$C_{18}$ aminoaryl, $C_2$–$C_{20}$ di(hydrocarbyl)amino, a heterocyclic group having at least three ring atoms, carboxamide (—C(O)$NR^1R^2$), or a group having the formula $(CH_2X)_cE$ in which X is O, $NH_x$, or a single bond, E is a functional group that includes active hydrogen and c is a whole number from 0 to 25, or both $R^4$ groups together with the carbon atoms to which they are attached form a 5- or 6-membered ring which optionally can have one or more further $R^4$ groups attached.

4. The compound of claim 1, wherein the compound has a wavelength of maximum absorbance of at least about 390 nm and a wavelength of maximum emission of no more than about 480 nm.

5. The compound of claim 1, wherein the compound is selective for $K^+$ and is attached to a substrate to form a cation-sensing structure, the structure being provided on a cassette having a fluid chamber and being in ion communication with $K^+$ ions in fluids that are contained in the fluid chamber.

6. The compound of claim 1, wherein the compound is incorporated into an ion sensor attached to a cassette having a flow passage, wherein the ion sensor is capable of withstanding autoclave sterilization.

7. The compound of claim 1, wherein the compound is incorporated into an ion sensor attached to a cassette assembly comprising: a first flow-through cassette casing having an inlet and an outlet and an opening covered with an ion-permeable membrane; and a second ion sensing cassette body.

8. The compound of claim 1, wherein the compound is incorporated into an ion sensor attached to a cassette having a flow passage, wherein the sensor is disposed inside the flow passage of the cassette.

9. The compound of claim 1, wherein m and n are both 1, Z is 0, and T is N.

10. The compound of claim 1, wherein the wavelengths of maximum absorbance and emission are at least about 20 nm apart.

11. A cation-sensing composite structure, comprising:

a substrate; and the fluorescent ionophoric compound of claim 1.

12. The sensing composite structure of claim 11, wherein the substrate comprises a polymer selected from the group consisting of: polyvinylchloride, copolymers and terpolymers of vinylchloride, copolymers of styrene and at least one of maleic acid and maleic anhydride, copolymers of alkyl vinyl ether and at least one of maleic acid and maleic anhydride, polymers and copolymers of vinyldimethyl aziactone, and copolymers of one of acrylate esters, methacrylate esters, acrylamides, and methacrylamides with one of acrylic acid and methacrylic acid.

13. A method of detecting the presence of a cation, comprising the steps of:

a) contacting the sensing composite structure of claim 11 with a cation-containing medium and allowing or providing a means for the cations to diffuse to the sensing composite structure to form an equilibrium complex with the fluorescent ionophoric compound of the sensing composite, wherein the ionophoric compound complex, when exposed to light of a wavelength range centered around $\lambda_1$, is capable of emitting light of a wavelength range centered around $\lambda_2$, wherein $\lambda_2$ is at least 10 nm greater than $\lambda_1$, $\lambda_1$ is at least about 380 nm, and $\lambda_2$ is no more than about 500 nm; and b) interrogating the complex with light of a wavelength range centered around $\lambda_1$ for a time sufficient for the complex to emit visible light of wavelength $\lambda_2$ which is collected and detected.

14. The method of claim 13, further comprising the step:

c) correlating the emitted light with the concentration of the cations to determine the cation concentration in the cation-containing medium.

15. The method of claim 14, wherein the cation is $K^+$.

16. The method of claim 13, wherein the interrogating light of a wavelength range centered around $\lambda_1$ is introduced by, and the emitted light of a wavelength range centered around $\lambda_2$ is transported to the detector by, at least one optical fiber.

17. The method of claim 13, wherein the cation is a metal ion.

18. A cation sensing composite structure, comprising:
a substrate; and
the fluorescent ionophoric compound of claim 1, wherein the compound is covalently bound to the substrate through at least one $R^1$ or $R^2$ or $R^3$ group by means of one of a bond and a multifunctional linking moiety, a first functionality of the linking moiety being complementary to a functionality of the $R^1$ or $R^2$ or $R^3$ group and a second functionality of the linking moiety being complementary to a functional group on the substrate.

19. The sensing composite structure of claim 18, wherein the functionalities of the linking moiety independently are an amine, amide, ester, oxirane, olefin; urea, silanol, carbamate, isocyanate, thioisocyanate, sulfonamide, sulfonyl chloride, sulfonic acid, carboxylic acid, carboxyl, chlorotriazine, hydrazine, hydrazide, or aldehyde.

20. The sensing composite structure of claim 18, wherein the linking moiety comprises a chain including 5 to 125 atoms selected from the group consisting of carbon, oxygen, nitrogen and sulfur.

21. The sensing composite structure of claim 18, wherein the substrate comprises a polymeric material.

22. The sensing composite structure of claim 21, wherein the polymeric material is coated on a membrane.

23. The sensing composite structure of claim 18, wherein the substrate is selected from the group consisting of hydrophilic porous polypropylene and hexanediamine functionalized cellulose.

24. The sensing composite structure of claim 23, wherein the substrate is substantially planar in shape.

25. The sensing composite structure of claim 18, wherein the substrate possesses a net negative charge.

26. The sensing composite structure of claim 18, wherein the composite structure comprises a powder that is adhered to a surface that is substantially planar.

27. A fluorescent ionophoric compound having the general formula:

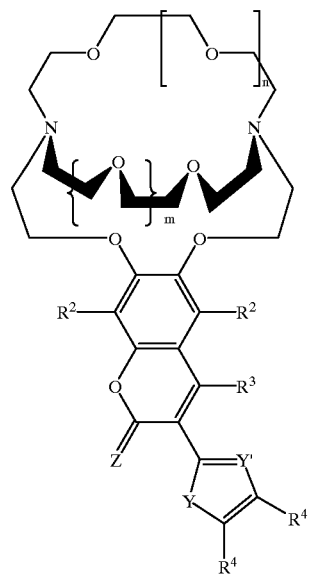

wherein m and n are independently 0 or 1;

Z is O or NH;

Y and Y' independently are O, S, $NH_x$, or $CH_y$ where x is 0 or 1 and y is 1 or 2, with the proviso that at least one of Y and Y' must be O, S, or $NH_x$, each $R^2$ independently is a sterically non-interferring group;

$R^3$ is a non-electron withdrawing group; and each $R^4$ group is independently hydrogen, halogen, a hydrocarbyl-containing group, a hetero-acyclic group, a heterocyclic group, or a group having the formula $(CH_2X)_cE$ in which X is O, NH, or a single bond, E is a functional group that includes active hydrogen, and c is a whole number from 0 to 100, or both $R^4$ groups together with the carbon atoms to which they are attached form a 5- or 6-membered ring which optionally can have one or more further $R^4$ groups attached, wherein the compound has a wavelength of maximum absorbance of at least about 380 nm a wavelength of maximum emission of no more than about 500 nm.

28. The compound of claim 27, wherein m and n are both 1 and Z is 0.

29. A fluorescent ionophoric compound, comprising a complexing moiety for selective binding of an ion; and a fluorescing moiety that contains close-lying $n\pi^*$ and $\pi\pi^*$ excited states, wherein the compound has a wavelength of maximum absorbance of at lest about 350 nm, the ionophoric compound having the formula:

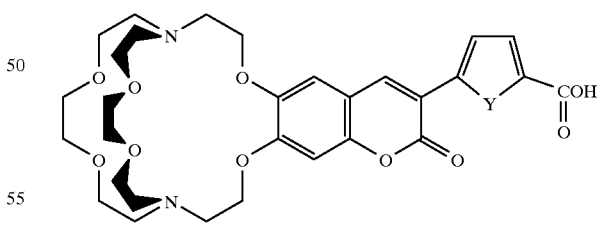

wherein Y is O, S, NH.

* * * * *

UNITED STATES PATENT AND TRADEMARK OFFICE
CERTIFICATE OF CORRECTION

PATENT NO. : 5,958,782
DATED : September 28, 1999
INVENTOR(S) : James G. Bentsen, Shih-Hung Chow, Elisa M. Cross, Kurt J. Halverson, John E. Trend, Cary A. Kipke, Masao Yafuso, and Sanjay L. Patil It is certified that error appears in the above-identified patent and that said Letters Patent is hereby corrected as shown below:

Title page,
OTHER PUBLICATIONS, "V. Mikes *Collect. Czech. Chem. Commun.* 1979." should read -- V. Mikes *Collect. Czech. Chem. Commun.* 1979, 44, 508-518. --

OTHER PUBLICATIONS, "S.L. Shapiro et al. *Springer Ser. Chem. Phys.* 1980." should read -- S.L. Shapiro et al. *Springer Ser. Chem. Phys.* 1980, 14, 237-241. --

Column 3,
Line 65, "diaklamino" should read -- dialkylamino --

Column 7,
Line 45, "nitrites" should read -- nitriles --

Column 13,
Lines 21-22, "1coumarocryptands" should read -- coumarocryptands --

Column 20,
Line 56, "lonophores" should read -- Ionophores --

Column 21,
Line 59, "aned" should read -- and --

Column 22,
Line 17, "he" should read -- the --

Column 25,
Line 32, "N-bromosuccinimiide" should read -- N-bromosuccinimide --
Lines 38-39, "ethyl-(5-bromoniethyl)-2-furoate" should read -- ethyl-(5-bromomethyl)-2-furoate --

Column 27,
Lines 61-62, "4,5-bis-(2'-chloroethoxy)-2hydroxybenzaldehyde" should read -- 4,5-bis-(2'-chloroethoxy)-2-hydroxybenzaldehyde --

Column 28,
Lines 56-57, "N,N-dlisoproplethylamine()IEA)" should read -- N,N-diisopropylethylamine (DIEA) --

Column 29,
Line 4, "spectrum" should read -- spectrum. --

UNITED STATES PATENT AND TRADEMARK OFFICE
CERTIFICATE OF CORRECTION

PATENT NO.    : 5,958,782
DATED         : September 28, 1999
INVENTOR(S)   : James G. Bentsen, Shih-Hung Chow, Elisa M. Cross, Kurt J. Halverson, John E. Trend, Cary A. Kipke, Masao Yafuso, and Sanjay L. Patil It is certified that error appears in the above-identified patent and that said Letters Patent is hereby corrected as shown below:

Column 63,
Line 42, "absortption" should read -- absorption --

Column 64,
Line 48, "(B GA)" should read -- (BGA) --

Column 66,
Line 14, "MMR" should read -- NMR --

Column 67,
Line 20, "nL" should read -- mL --

Column 71,
Line 9, "(VI)" should read -- (VII) --
Line 13, "$I_{max} = 374$ nm" should read -- $l_{max} = 374$ nm --
Line 14, "$I_{ex} = 371$ nm and $I_{cm} = 453$ nm" should read -- $l_{ex} = 371$ nm and $l_{cm} = 453$ nm --

Column 72,
Line 60, before "TABLE 40a" insert

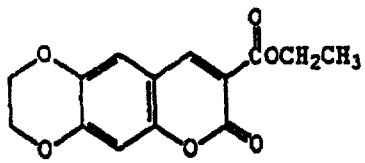

VIII

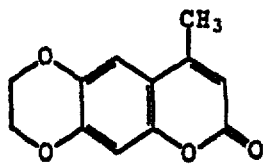

IX

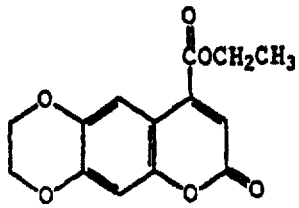

X

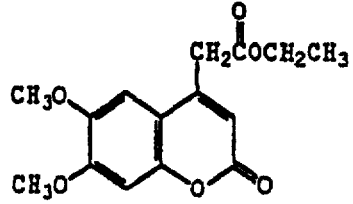

XI

UNITED STATES PATENT AND TRADEMARK OFFICE
CERTIFICATE OF CORRECTION

PATENT NO. : 5,958,782
DATED : September 28, 1999
INVENTOR(S) : James G. Bentsen, Shih-Hung Chow, Elisa M. Cross, Kurt J. Halverson, John E. Trend, Cary A. Kipke, Masao Yafuso, and Sanjay L. Patil It is certified that error appears in the above-identified patent and that said Letters Patent is hereby corrected as shown below:

Column 75,
Line 28, "dfisopropylethylamine" should read -- diisopropylethylamine --

Column 76,
Line 21, "[+]" should read -- [$K^+$] --

Column 79,
Line 4, "tonal" should read -- functional --
Line 33, "heterodic" should read -- heterocyclic --

Signed and Sealed this

Fifth Day of February, 2002

*Attest:*

*Attesting Officer*

JAMES E. ROGAN
*Director of the United States Patent and Trademark Office*